United States Patent
Bent et al.

(10) Patent No.: US 11,884,962 B2
(45) Date of Patent: *Jan. 30, 2024

(54) FUNCTIONALIZED GEL BEADS

(71) Applicant: 10X GENOMICS, INC., Pleasanton, CA (US)

(72) Inventors: Zachary Bent, Pleasanton, CA (US); Elliott Meer, Pleasanton, CA (US); Daniel Riordan, San Francisco, CA (US); Paul Ryvkin, San Jose, CA (US); Niranjan Srinivas, Pleasanton, CA (US); Jessica Terry, Pleasanton, CA (US); Alex Gagnon, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 342 days.

This patent is subject to a terminal disclaimer.

(21) Appl. No.: 17/095,578

(22) Filed: Nov. 11, 2020

(65) Prior Publication Data

US 2021/0277444 A1 Sep. 9, 2021

Related U.S. Application Data

(63) Continuation of application No. 16/680,343, filed on Nov. 11, 2019, now Pat. No. 10,876,147, which is a continuation of application No. 16/230,936, filed on Dec. 21, 2018, now Pat. No. 10,745,742, which is a continuation of application No. PCT/US2018/061391, filed on Nov. 15, 2018.

(60) Provisional application No. 62/629,561, filed on Feb. 12, 2018, provisional application No. 62/586,784, filed on Nov. 15, 2017.

(51) Int. Cl.
| | | |
|---|---|---|
| *C12Q 1/6806* | (2018.01) | |
| *C12Q 1/6811* | (2018.01) | |
| *C12Q 1/6834* | (2018.01) | |
| *C40B 20/04* | (2006.01) | |
| *C40B 50/16* | (2006.01) | |
| *C40B 50/18* | (2006.01) | |
| *G06K 19/06* | (2006.01) | |

(52) U.S. Cl.
CPC .......... *C12Q 1/6806* (2013.01); *C12Q 1/6811* (2013.01); *C12Q 1/6834* (2013.01); *C40B 20/04* (2013.01); *C40B 50/16* (2013.01); *C40B 50/18* (2013.01); *G06K 19/06093* (2013.01)

(58) Field of Classification Search
CPC .. C12Q 1/6806; C12Q 1/6811; C12Q 1/6834; C12Q 2521/319; C12Q 2525/113; C12Q 2525/125; C12Q 2563/149; C40B 20/04; C40B 50/16; C40B 50/18; G06K 19/06093

See application file for complete search history.

(56) References Cited

U.S. PATENT DOCUMENTS

| | | | |
|---|---|---|---|
| 2,797,149 | A | 6/1957 | Skeggs |
| 3,047,367 | A | 7/1962 | Kessler |
| 3,479,141 | A | 11/1969 | William et al. |
| 4,124,638 | A | 11/1978 | Hansen |
| 4,253,846 | A | 3/1981 | Smythe et al. |
| 4,582,802 | A | 4/1986 | Zimmerman et al. |
| 5,137,829 | A | 8/1992 | Nag et al. |
| 5,149,625 | A | 9/1992 | Church et al. |
| 5,185,099 | A | 2/1993 | Delpuech et al. |
| 5,202,231 | A | 4/1993 | Drmanac et al. |
| 5,270,183 | A | 12/1993 | Corbett et al. |
| 5,413,924 | A | 5/1995 | Kosak et al. |
| 5,418,149 | A | 5/1995 | Gelfand et al. |
| 5,436,130 | A | 7/1995 | Mathies et al. |
| 5,478,893 | A | 12/1995 | Ghosh et al. |
| 5,489,523 | A | 2/1996 | Mathur |
| 5,512,131 | A | 4/1996 | Kumar et al. |
| 5,558,071 | A | 9/1996 | Ward et al. |
| 5,585,069 | A | 12/1996 | Zanzucchi et al. |
| 5,587,128 | A | 12/1996 | Wilding et al. |
| 5,605,793 | A | 2/1997 | Stemmer et al. |
| 5,618,711 | A | 4/1997 | Gelfand et al. |
| 5,658,548 | A | 8/1997 | Padhye et al. |
| 5,695,940 | A | 12/1997 | Drmanac et al. |
| 5,700,642 | A | 12/1997 | Monforte et al. |
| 5,705,628 | A | 1/1998 | Hawkins |
| 5,708,153 | A | 1/1998 | Dower et al. |

(Continued)

FOREIGN PATENT DOCUMENTS

| | | |
|---|---|---|
| CN | 102292455 A | 12/2011 |
| CN | 102050953 B | 11/2012 |

(Continued)

OTHER PUBLICATIONS

Bose, et al. Scalable microfluidics for single-cell RNA printing and sequencing. Genome biology 16.1 (2015): 1-16.

(Continued)

*Primary Examiner* — David C Thomas
(74) *Attorney, Agent, or Firm* — Wilson Sonsini Goodrich & Rosati

(57) ABSTRACT

The present disclosure provides methods of generating supports (e.g., beads) comprising barcode molecules coupled thereto. A barcode molecule coupled to a support may comprise a barcode sequence and a functional sequence. A barcode molecule may be generated using two or more ligation reactions in a combinatorial fashion. A support comprising two or more different barcode molecules may be useful for analyzing or processing one or more analytes such as nucleic acid molecules, proteins, and/or perturbation agents.

18 Claims, 41 Drawing Sheets

Specification includes a Sequence Listing.

(56) References Cited

U.S. PATENT DOCUMENTS

| | | |
|---|---|---|
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,830,663 A | 11/1998 | Embleton et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,110,678 A | 8/2000 | Weisburg et al. |
| 6,123,798 A | 9/2000 | Gandhi et al. |
| 6,133,436 A | 10/2000 | Koester et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,176,962 B1 | 1/2001 | Soane et al. |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,915,679 B2 | 7/2005 | Chien et al. |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,076 B2 | 11/2009 | Davies et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,772,287 B2 | 8/2010 | Higuchi et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,927,797 B2 | 4/2011 | Nobile et al. |
| 7,943,671 B2 | 5/2011 | Herminghaus et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey et al. |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,658,430 B2 | 2/2014 | Miller et al. |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagilov et al. |
| 8,829,171 B2 | 9/2014 | Steemers et al. |
| 8,835,358 B2 | 9/2014 | Fodor et al. |
| 8,846,883 B2 | 9/2014 | Brown et al. |

(56) References Cited

U.S. PATENT DOCUMENTS

| | | |
|---|---|---|
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,628 B2 | 3/2015 | Stone et al. |
| 9,005,935 B2 | 4/2015 | Belyaev |
| 9,012,370 B2 | 4/2015 | Hong |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,040,256 B2 | 5/2015 | Grunenwald et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,085,798 B2 | 7/2015 | Chee |
| 9,089,844 B2 | 7/2015 | Hiddessen et al. |
| 9,102,980 B2 | 8/2015 | Brenner et al. |
| 9,126,160 B2 | 9/2015 | Ness et al. |
| 9,133,009 B2 | 9/2015 | Baroud et al. |
| 9,150,916 B2 | 10/2015 | Christen et al. |
| 9,156,010 B2 | 10/2015 | Colston et al. |
| 9,175,295 B2 | 11/2015 | Kaminaka et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,238,671 B2 | 1/2016 | Goryshin et al. |
| 9,238,815 B2 | 1/2016 | Shaw et al. |
| 9,249,460 B2 | 2/2016 | Pushkarev et al. |
| 9,266,104 B2 | 2/2016 | Link |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,410,201 B2 | 8/2016 | Hindson et al. |
| 9,417,190 B2 | 8/2016 | Hindson et al. |
| 9,436,088 B2 | 9/2016 | Seul et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,856,530 B2 | 1/2018 | Hindson et al. |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,119,167 B2 | 11/2018 | Srinivasan et al. |
| 10,137,449 B2 | 11/2018 | Bharadwaj et al. |
| 10,144,950 B2 | 12/2018 | Nolan |
| 10,150,117 B2 | 12/2018 | Bharadwaj et al. |
| 10,150,963 B2 | 12/2018 | Hindson et al. |
| 10,150,964 B2 | 12/2018 | Hindson et al. |
| 10,150,995 B1 | 12/2018 | Giresi et al. |
| 10,174,310 B2 | 1/2019 | Nolan |
| 10,208,343 B2 | 2/2019 | Hindson et al. |
| 10,221,436 B2 | 3/2019 | Hardenbol et al. |
| 10,221,442 B2 | 3/2019 | Hindson et al. |
| 10,227,648 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,337,061 B2 | 7/2019 | Hindson et al. |
| 10,344,329 B2 | 7/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,450,607 B2 | 10/2019 | Hindson et al. |
| 10,457,986 B2 | 10/2019 | Hindson et al. |
| 10,480,028 B2 | 11/2019 | Hindson et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 10,697,008 B2 | 6/2020 | Blauwkamp et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,876,147 B2 | 12/2020 | Meer et al. |
| 10,995,333 B2 | 5/2021 | Pfeiffer |
| 11,459,607 B1 | 10/2022 | Terry et al. |
| 11,467,153 B2 | 10/2022 | Belhocine et al. |
| 11,655,499 B1 | 5/2023 | Pfeiffer |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0051348 A1 | 12/2001 | Lee |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan |
| 2002/0119536 A1 | 8/2002 | Stern |
| 2002/0119544 A1 | 8/2002 | Yan et al. |
| 2002/0127736 A1 | 9/2002 | Chou et al. |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027203 A1 | 2/2003 | Fields |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |

(56) References Cited

U.S. PATENT DOCUMENTS

| | | |
|---|---|---|
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0040851 A1 | 3/2004 | Karger et al. |
| 2004/0063138 A1 | 4/2004 | Mcginnis et al. |
| 2004/0081962 A1 | 4/2004 | Chen et al. |
| 2004/0101680 A1 | 5/2004 | Barber, Jr. |
| 2004/0101880 A1 | 5/2004 | Rozwadowski et al. |
| 2004/0132122 A1 | 7/2004 | Banerjee et al. |
| 2004/0214175 A9 | 10/2004 | McKernan et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0037397 A1 | 2/2005 | Mirkin et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0136417 A1 | 6/2005 | Cole et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0250147 A1 | 11/2005 | Macevicz |
| 2005/0266582 A1 | 12/2005 | Modlin et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0009954 A1 | 1/2007 | Wang et al. |
| 2007/0020617 A1 | 1/2007 | Trnovsky et al. |
| 2007/0020640 A1 | 1/2007 | McCloskey et al. |
| 2007/0026401 A1 | 2/2007 | Hofmann et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0134277 A1 | 6/2007 | Chen et al. |
| 2007/0141584 A1 | 6/2007 | Roberts et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0196397 A1 | 8/2007 | Torii et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0056948 A1 | 3/2008 | Dale et al. |
| 2008/0124726 A1 | 5/2008 | Monforte |
| 2008/0138878 A1 | 6/2008 | Kubu et al. |
| 2008/0166720 A1 | 7/2008 | Hsieh et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2008/0268450 A1 | 10/2008 | Nam et al. |
| 2008/0268507 A1 | 10/2008 | Xu et al. |
| 2008/0299595 A1 | 12/2008 | Wong et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0047713 A1 | 2/2009 | Handique |
| 2009/0048124 A1 | 2/2009 | Leamon et al. |
| 2009/0053169 A1 | 2/2009 | Castillo et al. |
| 2009/0062129 A1 | 3/2009 | Mckernan et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0131543 A1 | 5/2009 | Weitz et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155563 A1 | 6/2009 | Petsev et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0235990 A1 | 9/2009 | Beer |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2009/0325260 A1 | 12/2009 | Otto et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0184928 A1 | 7/2010 | Kumacheva |
| 2010/0187705 A1 | 7/2010 | Lee et al. |
| 2010/0203647 A1 | 8/2010 | Hang et al. |
| 2010/0210479 A1 | 8/2010 | Griffiths et al. |
| 2010/0216153 A1 | 8/2010 | Lapidus et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |

(56) References Cited

U.S. PATENT DOCUMENTS

| | | |
|---|---|---|
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0166034 A1 | 7/2011 | Kwong et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0293701 A1 | 12/2011 | Bratzler et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van Der Zaag et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0190037 A1 | 7/2012 | Durin et al. |
| 2012/0196288 A1 | 8/2012 | Beer |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0219947 A1 | 8/2012 | Yurkovetsky et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0289428 A1 | 11/2012 | Duffy et al. |
| 2012/0295819 A1 | 11/2012 | Leamon et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0079251 A1 | 3/2013 | Boles |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0109596 A1 | 5/2013 | Peterson et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0268206 A1 | 10/2013 | Porreca et al. |
| 2013/0273640 A1 | 10/2013 | Krishnan et al. |
| 2013/0274117 A1 | 10/2013 | Church et al. |
| 2013/0296173 A1 | 11/2013 | Callow et al. |
| 2013/0311106 A1 | 11/2013 | White et al. |
| 2013/0343317 A1 | 12/2013 | Etemad et al. |
| 2013/0344508 A1 | 12/2013 | Schwartz et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0080717 A1 | 3/2014 | Li et al. |
| 2014/0093916 A1 | 4/2014 | Belyaev |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet et al. |
| 2014/0199331 A1 | 7/2014 | Robillard et al. |
| 2014/0199730 A1 | 7/2014 | Agresti et al. |
| 2014/0199731 A1 | 7/2014 | Agresti et al. |
| 2014/0200166 A1 | 7/2014 | Van Rooyen et al. |
| 2014/0206073 A1 | 7/2014 | Park et al. |
| 2014/0206554 A1 | 7/2014 | Hindson et al. |
| 2014/0214334 A1 | 7/2014 | Plattner et al. |
| 2014/0221239 A1 | 8/2014 | Carman et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0272996 A1 | 9/2014 | Bemis |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0323316 A1 | 10/2014 | Drmanac et al. |
| 2014/0338753 A1 | 11/2014 | Sperling et al. |
| 2014/0357500 A1 | 12/2014 | Vigneault et al. |
| 2014/0357530 A1 | 12/2014 | Zhang et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0031037 A1 | 1/2015 | Li et al. |
| 2015/0057163 A1 | 2/2015 | Rotem et al. |
| 2015/0066385 A1 | 3/2015 | Schnall-Levin et al. |
| 2015/0072396 A1 | 3/2015 | Gee et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0125904 A1 | 5/2015 | Ting et al. |
| 2015/0133344 A1 | 5/2015 | Shendure et al. |
| 2015/0211056 A1 | 7/2015 | Um et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0225777 A1 | 8/2015 | Hindson et al. |

(56) References Cited

U.S. PATENT DOCUMENTS

| | | |
|---|---|---|
| 2015/0225778 A1 | 8/2015 | Hindson et al. |
| 2015/0225786 A1 | 8/2015 | Litterst et al. |
| 2015/0247182 A1 | 9/2015 | Faham et al. |
| 2015/0258543 A1 | 9/2015 | Baroud et al. |
| 2015/0259736 A1 | 9/2015 | Steemers et al. |
| 2015/0267191 A1 | 9/2015 | Steelman et al. |
| 2015/0267246 A1 | 9/2015 | Baroud et al. |
| 2015/0291942 A1 | 10/2015 | Gloeckner et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329852 A1 | 11/2015 | Nolan |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0025726 A1 | 1/2016 | Altin et al. |
| 2016/0032282 A1 | 2/2016 | Vigneault et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0145683 A1 | 5/2016 | Fan et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0194699 A1 | 7/2016 | Borodina et al. |
| 2016/0201125 A1 | 7/2016 | Samuels et al. |
| 2016/0203196 A1 | 7/2016 | Schnall-Levin et al. |
| 2016/0208323 A1 | 7/2016 | Bernstein et al. |
| 2016/0231324 A1 | 8/2016 | Zhao et al. |
| 2016/0232291 A1 | 8/2016 | Kyriazopoulou-Panagiotopoulou et al. |
| 2016/0244742 A1 | 8/2016 | Linnarsson et al. |
| 2016/0244809 A1 | 8/2016 | Belgrader et al. |
| 2016/0244811 A1 | 8/2016 | Edwards |
| 2016/0244825 A1 | 8/2016 | Vigneault et al. |
| 2016/0251697 A1 | 9/2016 | Nolan |
| 2016/0257984 A1 | 9/2016 | Hardenbol et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0314242 A1 | 10/2016 | Schnall-Levin et al. |
| 2016/0326583 A1 | 11/2016 | Johnson et al. |
| 2016/0348093 A1 | 12/2016 | Price et al. |
| 2016/0350478 A1 | 12/2016 | Chin et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0073747 A1 | 3/2017 | Joung et al. |
| 2017/0114390 A1 | 4/2017 | Hindson et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0183701 A1 | 6/2017 | Agresti et al. |
| 2017/0211127 A1 | 7/2017 | Mikkelsen et al. |
| 2017/0235876 A1 | 8/2017 | Jaffe et al. |
| 2017/0247757 A1 | 8/2017 | Hindson et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0080021 A1 | 3/2018 | Reuter et al. |
| 2018/0080075 A1 | 3/2018 | Brenner et al. |
| 2018/0087050 A1 | 3/2018 | Zheng et al. |
| 2018/0088112 A1 | 3/2018 | Fan et al. |
| 2018/0094298 A1 | 4/2018 | Hindson et al. |
| 2018/0094312 A1 | 4/2018 | Hindson et al. |
| 2018/0094313 A1 | 4/2018 | Hindson |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195060 A1 | 7/2018 | Wang et al. |
| 2018/0195112 A1 | 7/2018 | Lebofsky et al. |
| 2018/0196781 A1 | 7/2018 | Wong |
| 2018/0216162 A1 | 8/2018 | Belhocine et al. |
| 2018/0237951 A1 | 8/2018 | Bock et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0267036 A1 | 9/2018 | Fan et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0305685 A1 | 10/2018 | Li et al. |
| 2018/0312822 A1 | 11/2018 | Lee et al. |
| 2018/0312873 A1 | 11/2018 | Zheng |
| 2018/0327838 A1 | 11/2018 | Giresi et al. |
| 2018/0327839 A1 | 11/2018 | Hindson et al. |
| 2018/0334670 A1 | 11/2018 | Bharadwaj et al. |
| 2018/0335424 A1 | 11/2018 | Chen et al. |
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0340939 A1 | 11/2018 | Gaublomme et al. |
| 2018/0346979 A1 | 12/2018 | Hindson et al. |
| 2018/0363029 A1 | 12/2018 | Hindson et al. |
| 2018/0371540 A1 | 12/2018 | Hindson et al. |
| 2018/0371545 A1 | 12/2018 | Wong et al. |
| 2018/0376609 A1 | 12/2018 | Ju et al. |
| 2019/0002967 A1 | 1/2019 | Chen et al. |
| 2019/0024166 A1 | 1/2019 | Hindson et al. |
| 2019/0032129 A1 | 1/2019 | Hindson et al. |
| 2019/0032130 A1 | 1/2019 | Giresi et al. |
| 2019/0040382 A1 | 2/2019 | Steemers et al. |
| 2019/0040464 A1 | 2/2019 | Giresi et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0078150 A1 | 3/2019 | Chen et al. |
| 2019/0085391 A1 | 3/2019 | Hindson et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0153436 A1 | 5/2019 | Belhocine et al. |

(56) References Cited

U.S. PATENT DOCUMENTS

| | | |
|---|---|---|
| 2019/0153532 A1 | 5/2019 | Bharadwaj et al. |
| 2019/0169666 A1 | 6/2019 | Hardenbol et al. |
| 2019/0176152 A1 | 6/2019 | Bharadwaj et al. |
| 2019/0177789 A1 | 6/2019 | Hindson et al. |
| 2019/0177800 A1 | 6/2019 | Boutet et al. |
| 2019/0203262 A1 | 7/2019 | Hindson et al. |
| 2019/0203291 A1 | 7/2019 | Hindson et al. |
| 2019/0249226 A1 | 8/2019 | Bent et al. |
| 2019/0276817 A1 | 9/2019 | Hindson et al. |
| 2019/0292593 A1 | 9/2019 | Hindson et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376058 A1 | 12/2019 | Belhocine |
| 2019/0376118 A1 | 12/2019 | Belhocine et al. |
| 2019/0382836 A1 | 12/2019 | Hindson et al. |
| 2020/0005902 A1 | 1/2020 | Mellen et al. |
| 2020/0020417 A1 | 1/2020 | Schnall-Levin et al. |
| 2020/0024596 A1 | 1/2020 | Belhocine et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0165603 A1 | 5/2020 | Belhocine et al. |
| 2020/0190551 A1 | 6/2020 | Hardenbol et al. |
| 2020/0232027 A1 | 7/2020 | Hindson et al. |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |

FOREIGN PATENT DOCUMENTS

| | | |
|---|---|---|
| CN | 103202812 A | 7/2013 |
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1944368 A1 | 7/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 A1 | 9/2013 |
| EP | 2752664 A1 | 7/2014 |
| EP | 2635679 B1 | 4/2017 |
| EP | 3013957 B1 | 9/2018 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| JP | 2012522517 A | 9/2012 |
| RU | 2321638 C2 | 4/2008 |
| WO | WO-84/02000 | 5/1984 |
| WO | WO-9301498 A1 | 1/1993 |
| WO | WO-9418218 A1 | 8/1994 |
| WO | WO-9419101 A1 | 9/1994 |
| WO | WO-9423699 A1 | 10/1994 |
| WO | WO-95/30782 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9942597 A1 | 8/1999 |
| WO | WO-99/52708 | 10/1999 |
| WO | WO-0008212 A1 | 2/2000 |
| WO | WO-2000008212 A1 | 2/2000 |
| WO | WO-0023181 A1 | 4/2000 |
| WO | WO-0026412 A1 | 5/2000 |
| WO | WO-0034527 A2 | 6/2000 |
| WO | WO-0043766 A1 | 7/2000 |
| WO | WO-0070095 A2 | 11/2000 |
| WO | WO-0102850 A1 | 1/2001 |
| WO | WO-2001002850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006030993 A1 | 3/2006 |
| WO | WO-2006040551 A2 | 4/2006 |
| WO | WO-2006071770 A2 | 7/2006 |
| WO | WO-2006078841 A1 | 7/2006 |
| WO | WO-2006086210 A2 | 8/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A2 | 11/2008 |
| WO | WO-2008061193 A3 | 11/2008 |
| WO | WO-2008134153 A1 | 11/2008 |
| WO | WO-2008135512 A2 | 11/2008 |
| WO | WO-2008150432 A1 | 12/2008 |
| WO | WO-2008135512 A3 | 1/2009 |
| WO | WO-2009005680 A1 | 1/2009 |
| WO | WO-2009011808 A1 | 1/2009 |
| WO | WO-2009015296 A1 | 1/2009 |

(56) References Cited

FOREIGN PATENT DOCUMENTS

| | | |
|---|---|---|
| WO | WO-2009023821 A1 | 2/2009 |
| WO | WO-2009048532 A2 | 4/2009 |
| WO | WO-2009061372 A1 | 5/2009 |
| WO | WO-2009085215 A1 | 7/2009 |
| WO | WO-2009147386 A1 | 12/2009 |
| WO | WO-2009152928 A2 | 12/2009 |
| WO | WO-2010004018 A2 | 1/2010 |
| WO | WO-2010009735 A2 | 1/2010 |
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010117620 A2 | 10/2010 |
| WO | WO-2010127304 A2 | 11/2010 |
| WO | WO-2010148039 A2 | 12/2010 |
| WO | WO-2010151776 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011106314 A2 | 9/2011 |
| WO | WO-2011140510 A2 | 11/2011 |
| WO | WO-2011140627 A1 | 11/2011 |
| WO | WO-2011156529 A2 | 12/2011 |
| WO | WO-2012012037 A1 | 1/2012 |
| WO | WO-2012019765 A1 | 2/2012 |
| WO | WO-2012047889 A2 | 4/2012 |
| WO | WO-2012048340 A2 | 4/2012 |
| WO | WO-2012048341 A1 | 4/2012 |
| WO | WO-2012055929 A1 | 5/2012 |
| WO | WO-2012061832 A1 | 5/2012 |
| WO | WO-2012083225 A2 | 6/2012 |
| WO | WO-2012087736 A1 | 6/2012 |
| WO | WO-2012100216 A2 | 7/2012 |
| WO | WO-2012106546 A2 | 8/2012 |
| WO | WO-2012112804 A1 | 8/2012 |
| WO | WO-2012112970 A2 | 8/2012 |
| WO | WO-2012116250 A1 | 8/2012 |
| WO | WO-2012116331 A2 | 8/2012 |
| WO | WO-2012136734 A1 | 10/2012 |
| WO | WO-2012142531 A2 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012150317 A1 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013035114 A1 | 3/2013 |
| WO | WO-2013036929 A1 | 3/2013 |
| WO | WO-2013055955 A1 | 4/2013 |
| WO | WO-2013096643 A1 | 6/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014018460 A1 | 1/2014 |
| WO | WO-2014028378 A2 | 2/2014 |
| WO | WO-2014028537 A1 | 2/2014 |
| WO | WO-2014053854 A1 | 4/2014 |
| WO | WO-2014071361 A1 | 5/2014 |
| WO | WO-2014072703 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014145047 A1 | 9/2014 |
| WO | WO-2014150931 A1 | 9/2014 |
| WO | WO-2014165559 A2 | 10/2014 |
| WO | WO-2014182835 A1 | 11/2014 |
| WO | WO-2014189957 A2 | 11/2014 |
| WO | WO-2014200767 A1 | 12/2014 |
| WO | WO-2014210353 A2 | 12/2014 |
| WO | WO-2015015199 A2 | 2/2015 |
| WO | WO-2015031691 A1 | 3/2015 |
| WO | WO-2015044428 A1 | 4/2015 |
| WO | WO-2014210353 A3 | 7/2015 |
| WO | WO-2015157567 A1 | 10/2015 |
| WO | WO-2015164212 A1 | 10/2015 |
| WO | WO-2015185067 A1 | 12/2015 |
| WO | WO-2015188839 A2 | 12/2015 |
| WO | WO-2015200891 A1 | 12/2015 |
| WO | WO-2015200893 A2 | 12/2015 |
| WO | WO-2016040476 A1 | 3/2016 |
| WO | WO-2016033251 A3 | 4/2016 |
| WO | WO-2016061517 A2 | 4/2016 |
| WO | WO-2016100976 A2 | 6/2016 |
| WO | WO-2016126871 A2 | 8/2016 |
| WO | WO-2016130578 A1 | 8/2016 |
| WO | WO-2016138496 A1 | 9/2016 |
| WO | WO-2016149661 A1 | 9/2016 |
| WO | WO-2016168584 A1 | 10/2016 |
| WO | WO-2016170126 A1 | 10/2016 |
| WO | WO-2016187256 A2 | 11/2016 |
| WO | WO-2016187717 A1 | 12/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017053905 A1 | 3/2017 |
| WO | WO-2017066231 A1 | 4/2017 |
| WO | WO-2017075265 A1 | 5/2017 |
| WO | WO-2017075294 A1 | 5/2017 |
| WO | WO-2017079593 A1 | 5/2017 |
| WO | WO-2017096158 A1 | 6/2017 |
| WO | WO-2017117358 A1 | 7/2017 |
| WO | WO-2017151828 A1 | 9/2017 |
| WO | WO-2017156336 A1 | 9/2017 |
| WO | WO-2017180420 A1 | 10/2017 |
| WO | WO-2017180949 A1 | 10/2017 |
| WO | WO-2017184707 A1 | 10/2017 |
| WO | WO-2017197343 A2 | 11/2017 |
| WO | WO-2017197343 A3 | 2/2018 |
| WO | WO-2018031631 A1 | 2/2018 |
| WO | WO-2018039338 A1 | 3/2018 |
| WO | WO-2018039969 A1 | 3/2018 |
| WO | WO-2018045186 A1 | 3/2018 |
| WO | WO-2018058073 A2 | 3/2018 |
| WO | WO-2018091676 A1 | 5/2018 |
| WO | WO-2018103025 A1 | 6/2018 |
| WO | WO-2018119301 A1 | 6/2018 |
| WO | WO-2018119447 A2 | 6/2018 |
| WO | WO-2018125982 A1 | 7/2018 |
| WO | WO-2018129368 A2 | 7/2018 |
| WO | WO-2018132635 A1 | 7/2018 |
| WO | WO-2018119447 A3 | 8/2018 |
| WO | WO-2018172726 A1 | 9/2018 |
| WO | WO-2018174827 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019071039 A1 | 4/2019 |
| WO | WO-2019083852 A1 | 5/2019 |
| WO | WO-2019084043 A1 | 5/2019 |
| WO | WO-2019084165 A1 | 5/2019 |
| WO | WO-2019084328 A1 | 5/2019 |
| WO | WO-2019099751 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |

(56) References Cited

FOREIGN PATENT DOCUMENTS

| WO | WO-2019157529 A1 | 8/2019 |
|---|---|---|
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/318,364, inventors Bava; Felice Alessio et al., filed May 12, 2021.
Co-pending U.S. Appl. No. 17/381,612, inventor Martinez; Luigi Jhon Alvarado, filed Jul. 21, 2021.
Co-pending U.S. Appl. No. 17/499,039, inventors Pfeiffer; Katherine et al., filed Oct. 12, 2021.
Co-pending U.S. Appl. No. 17/512,241, inventors Hill; Andrew John et al., filed Oct. 27, 2021.
Co-pending U.S. Appl. No. 17/517,408, inventors Salmanzadeh; Alireza et al., filed Nov. 2, 2021.
Co-pending U.S. Appl. No. 17/518,213, inventor Lund; Paul Eugene, filed Nov. 3, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Co-pending U.S. Appl. No. 17/580,947, inventor Gibbons; Michael, filed Jan. 21, 2022.
Co-pending U.S. Appl. No. 17/831,835, inventor Martinez; Luigi Jhon Alvarado, filed Jun. 3, 2022.
Co-pending U.S. Appl. No. 17/957,781, inventor Bava; Felice Alessio, filed Sep. 30, 2022.
Co-pending U.S. Appl. No. 18/046,843, inventor Toh; Mckenzi, filed Oct. 14, 2022.
Fowler, Enhancement of Mixing by Droplet-Based Microfluidics, Int Conf MEMS 97-100 (2002).
Hall, The EBG system of *E. coli*: origin and evolution of a novel beta-galactosidase for the metabolism of lactose, Genetica 118(2-3):143-56 (2003).
Jestin et al., A Method for the Selection of Catalytic Activity Using Phage Display and Proximity Coupling, Agnew. Chem. Int. Ed. Engi. 38(8):1124-1127 (1999).
Kilgore, et al. Single-molecule and population probing of chromatin structure using DNA methyltransferases. Methods. Mar. 2007;41(3):320-32.
Kruse, A.C. et al. "Structure of a mutant beta toxin from *Staphylococcus aureus* reveals domain swapping and conformational flexibility" Acta Crystallographica (Apr. 1, 2011) Epub Mar. 24, 2011, 67(4):438-441; Supplemental Data p. 1 DOI: 10.1107/S1744309111005239.
Laulicht et al., Evaluation of continuous flow nanosphere formation by controlled microfluidic transport, American Chem. Society (Aug. 6, 2008).
Lipkin et al., Biomarkers of increased susceptibility to gastrointestinal cancer: new application to studies of cancer prevention in human subjects, Cancer Research 48:235-245 (1988).
Zilionis et al. Single-cell barcoding and sequencing using droplet microfluidics, Nature Protocols, 12(1) 2017: 44.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Chien et al. "Multiport flow-control system for lab-on-a-chip microfluidic devices", Fresenius J. Anal Chem, 371:106-111 (Jul. 27, 2001).
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/434,102, inventors Price; Andrew D. et al., filed Jun. 6, 2019.
Co-pending U.S. Appl. No. 16/708,214, inventors Wheeler; Tobias Daniel et al., filed Dec. 9, 2019.
Co-pending U.S. Appl. No. 16/737,762, inventors Price; Andrew D. et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 16/800,450, inventor Katherine; Pfeiffer, filed Feb. 25, 2020.
Duffy et al., Rapid Protyping of Microfluidic Systems and Polydimethylsiloxane, Anal Chem 70:4974-4984 (1998).
Eid, et al. Real-time DNA sequencing from single polymerase molecules. Science. Jan. 2, 2009;323(5910):133-8. doi: 10.1126/science.1162986. Epub Nov. 20, 2008.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Klein, et al. Droplet barcoding for single-cell transcriptomics applied to embryonic stem cells. Cell. May 21, 2015; 161:1187-1201.
Lo, et al. On the design of clone-based haplotyping. Genome Biol. 2013;14(9):R100.

(56) References Cited

OTHER PUBLICATIONS

Nisisako, T. et al., Microfluidics large-scale integration on a chip for mass production of monodisperse droplets and particles, The Royal Society of Chemistry: Lab Chip, (Nov. 23, 2007) 8:287-293.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Skerra. Phosphorothioate primers improve the amplification of DNA sequences by DNA polymerases with proofreading activity. Nucleic Acids Res. Jul. 25, 1992; 20(14):3551-4.
Turchinovich, et al. "Capture and Amplification by Tailing and Switching (CATS): an Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Abate et al., Valve-based flow focusing for drop formation. Appl Phys Lett. 2009;94. 3 pages.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adamson et al., "Production of arrays of chemically distinct nanolitre plugs via repeated splitting in microfluidic devices", Lab Chip 6(9): 1178-1186 (Sep. 2006).
Adey, et al. Rapid, low-input, low-bias construction of shotgun fragment libraries by high-density in vitro transposition. Genome Biology 11:R119 (2010).
Adey, et al., "Ultra-low-input, tagmentation-based whole-genome bisulfite sequencing", Genome Research, 2012, 22 ;6): 1139-1143.
Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
AH006633.3 (*Homo sapiens* clone P1 and PAC max interactor 1 (MXI1) gene, complete cds, NCBI Reference Sequence, priority to Jun. 10, 2016, 5 pages) (Year:2016).
Ahern, "Biochemical, Reagents Kits Offer Scientists Good Return on Investment" The Scientist (1995) 9(15):1-7.
Ahern, H. The Scientist, vol. 20, pp. 20 and 22. July (Year: 1995).
Aikawa, et al. Spherical Phospholipid Polymer Hydrogels for Cell Encapsulation Prepared with a Flow-Focusing Microfluidic Channel Device. Langmuir. Jan. 31, 2012;28(4):2145-50. doi: 10.1021/la2037586. Epub Dec. 22, 2011.
Ailenberg, et al. (2000) Controlled Hot Start and Improved Specificity in Carrying Out PCR Utilizing Touch-up and Loop Incorporated Primers (TULIPS). BioTechniques, 29:1018-1024. (Year: 2000).
Aitman, et al. Copy number polymorphism in Fcgr3 predisposes to glomerulonephritis in rats and humans. Nature. Feb. 16, 2006;439(7078):851-5.

Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Allazetta, et al. Microfluidic Synthesis of Cell-Type-Specific Artificial Extracellular Matrix Hydrogels. Biomacromolecules. Apr. 8, 2013;14(4):1122-31. doi: 10.1021/bm4000162. Epub Mar. 8, 2013.
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Anonymous: "Dynal MPC(TM)-S", Oct. 13, 2008 (Oct. 13, 2008), XP055603532, Retrieved from the Internet on Jul. 9, 2019; URL: https://www.veritastk.co.jp/products/pdf/120%2020D.Dynal_MPC-S%28rev005%29.pdf>.
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "TCEP=HCI" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCI_UG.pdf.
Anonymous: "Three Ways to Get Intimate with Epigenetic Marks". Oct. 24, 2012. Retrieved from Internet: https://epigenie.com/three-ways-to-get-intimate-with-epigenetic-marks/.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Ason et al. DNA sequence bias during Tn5 transposition. Journal of molecular biology 335.5 (2004): 1213-1225.
Attia, et al. Micro-injection moulding of polymer microfluidic devices. Microfluidics and nanofluidics. 2009; 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.
Banchelli, et al. Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.
Bansal et al. "An MCMC algorithm for haplotype assembly from whole-genome sequence data," (2008) Genome Res 18:1336-1346.
Bansal et al. "HapCUT: an efficient and accurate algorithm for the haplotype assembly problem," Bioinformatics (2008) 24:i153-i159.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Bassett, et al. Competitive ligand exchange of crosslinking ions for ionotropic hydrogel formation. J. Mater. Chem. B, 2016,4, 6175-6182.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bedtools: General Usage, http://bedtools.readthedocs.io/en/latest/content/generalusage.html; Retrieved from the Internet Jul. 8, 2016.
Bentley, et al. 2008. Supplementary Information. pp. 1-55 Nature. Nov. 6, 2008; 456(7218):53-9.
Bentley et al. "Accurate whole human genome sequencing using reversible terminator chemistry," (2008) Nature 456:53-59.

(56) References Cited

OTHER PUBLICATIONS

Bentolila, et al. Single-step multicolor fluorescence in situ hybridization using semiconductor quantum dot-DNA conjugates. Cell Biochem Biophys. 2006;45(1):59-70.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bjornsson et al., Intra-individual change over time in DNA methylation with familial clustering, JAMA, Jun. 25, 2008, vol. 299 No. 24, pp. 2877-2883.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Boulanger, et al, "Massively parallel haplotyping on microscopic beads for the high-throughput phase analysis of single molecules", PLOS One, vol. 7:1-10, 2012.
Boyle, et al. "High-resolution genome-wide in vivo footprinting of diverse transcription factors in human cells", Genome Res. Mar. 2011;21(3):456-64.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Bray, "The JavaScript Object Notation (JSON) Data Interchange Format," Mar. 2014, retrieved from the Internet Feb. 15, 2015; https://tools.ietf.org/html/rfc7159.
Brenner, et al. In vitro cloning of complex mixtures of DNA on microbeads: physical separation of differentially expressed cDNAs. Proc Natl Acad Sci U S A. Feb. 15, 2000;97(4):1665-70.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Buenrostro, et al. ATAC-seq: a Method for Assaying Chromatin Accessibility Genome-Wide. Curr Protoc Mol Biol. Jan. 5, 2015;109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Bystrykh, et al. Generalized DNA barcode design based on Hamming codes. PLoS One. 2012;7(5):e36852. doi: 10.1371/journal.pone.0036852. Epub May 17, 2012.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Caruccio, et al. Nextera Technology for NGS DNA Library Preparation: Simultaneous Fragmentation and Tagging by In Vitro Transposition, Nextera Technology, 2009, 16-3. (Year: 2009).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241-55 (2011).
Casbon, et al, "Reflex: intramolecular barcoding of long-range PCR products for sequencing multiple pooled DNAs", Nucleic Acids Res., pp. 1-6, 2013.
Cejas, P. et al. "Chromatin immunoprecipitation from fixed clinical tissues reveals tumor-specific enhancer profiles" Nature Med (2016) 22(6):685-691.
Chang et al. Droplet-based microfluidic platform for heterogeneous enzymatic assays, 2013, Lab Chip, 13, 1817-1822 (Year: 2013).
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen et al. BreakDancer: an algorithm for high-resolution mapping of genomic structural variation. Nature Methods (2009) 6(9):677-681.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Christian, et al. Targeting DNA double-strand breaks with TAL effector nucleases. Genetics.186 (2010): 757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Cleary et al. "Joint variant and de novo mutation identification on pedigrees from highthroughput sequencing data," J Comput Biol (2014) 21:405-419.
Cong et al. Multiplex genome engineering using CRISPR/Cas systems. Science 339(6121):819-23 (2013).

(56) References Cited

OTHER PUBLICATIONS

Cook, et al. Copy-number variations associated with neuropsychiatric conditions. Nature. Oct. 16, 2008;455(7215):919-23. doi: 10.1038/nature07458.
Co-pending PCT/US2019/024418, filed Mar. 27, 2019.
Co-pending PCT/US2019/046940, filed Aug. 16, 2019.
Co-pending U.S. Appl. No. 15/440,772, inventors Hindson; Benjamin J. et al., filed Feb. 23, 2017.
Co-pending U.S. Appl. No. 15/449,741, inventors Hindson; Benjamin et al., filed Mar. 3, 2017.
Co-pending U.S. Appl. No. 16/033,065, inventors Giresi; Paul et al., filed Jul. 11, 2018.
Co-pending U.S. Appl. No. 16/138,448, inventor Hindson; Benjamin, filed Sep. 21, 2018.
Co-pending U.S. Appl. No. 16/144,832, inventor Hindson; Benjamin, filed Sep. 27, 2018.
Co-pending U.S. Appl. No. 16/160,576, inventors Giresi; Paul et al., filed Oct. 15, 2018.
Co-pending U.S. Appl. No. 16/160,719, inventors Giresi; Paul et al., filed Oct. 15, 2018.
Co-pending U.S. Appl. No. 16/165,389, inventors Hindson; Benjamin et al., filed Oct. 19, 2018.
Co-pending U.S. Appl. No. 16/196,684, inventor McDermott; Geoffrey, filed Nov. 20, 2018.
Co-pending U.S. Appl. No. 16/206,168, inventor Belhocine; Kamila, filed Nov. 30, 2018.
Co-pending U.S. Appl. No. 16/212,441, inventor Hindson; Benjamin, filed Dec. 6, 2018.
Co-pending U.S. Appl. No. 16/228,261, inventor Bharadwaj; Rajiv, filed Dec. 20, 2018.
Co-pending U.S. Appl. No. 16/228,362, inventor Hardenbol; Paul, filed Dec. 20, 2018.
Co-pending U.S. Appl. No. 16/231,142, inventor Hindson; Benjamin, filed Dec. 21, 2018.
Co-pending U.S. Appl. No. 16/231,185, inventor Hindson; Benjamin, filed Dec. 21, 2018.
Co-pending U.S. Appl. No. 16/249,688, inventor Hindson; Benjamin, filed Jan. 16, 2019.
Co-pending U.S. Appl. No. 16/294,769, inventor Hindson; Benjamin, filed Mar. 6, 2019.
Co-pending U.S. Appl. No. 16/419,555, inventor Belhocine; Kamila, filed May 22, 2019.
Co-pending U.S. Appl. No. 16/419,820, inventor Bharadwaj; Rajiv, filed May 22, 2019.
Co-pending U.S. Appl. No. 16/434,089, inventor Bent; Zachary, filed Jun. 6, 2019.
Co-pending U.S. Appl. No. 16/435,362, inventors Hindson; Christopher et al., filed Jun. 7, 2019.
Co-pending U.S. Appl. No. 16/410,953, filed May 13, 2019.
Co-pending U.S. Appl. No. 16/415,617, filed May 17, 2019.
Co-pending U.S. Appl. No. 16/434,068, filed Jun. 6, 2019.
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,095, filed Jun. 6, 2019.
Co-pending U.S. Appl. No. 16/434,099, filed Jun. 6, 2019.
Co-pending U.S. Appl. No. 16/434,102, filed Jun. 6, 2019.
Co-pending U.S. Appl. No. 16/435,393, filed Jun. 7, 2019.
Co-pending U.S. Appl. No. 16/439,568, filed Jun. 12, 2019.
Co-pending U.S. Appl. No. 16/439,675, filed Jun. 12, 2019.
Co-pending U.S. Appl. No. 16/454,485, filed Jun. 27, 2019.
Co-pending U.S. Appl. No. 16/530,930, filed Aug. 2, 2019.
Co-pending U.S. Appl. No. 16/575,280, filed Sep. 18, 2019.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PHD Thesis. 2002.
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Cusanovich, et al. Multiplex single-cell profiling of chromatin accessibility by combinatorial cellular indexing. Science, May 22, 2015;348(6237):910-14.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Dangla, et al. Droplet microfluidics driven by gradients of confinement. Proc Natl Acad Sci U S A. Jan. 15, 2013; 110(3): 853-858. Published online Jan. 2, 2013. doi: 10.1073/pnas.1209186110.
De Bruin et al., UBS Investment Research. Q-Series®: DNA Sequencing. UBS Securities LLC. Jul. 12, 2007. 15 pages.
Definition of "corresponding", Merriam-Webster Online, downloaded from http://www.merriam-webster.com/dictionary/corresponding (Year: 2019).
Dekker, et al. Capturing chromosome conformation. Science. Feb. 15, 2002;295(5558):1306-11.
Delehanty, et al. Peptides for specific intracellular delivery and targeting of nanoparticles: implications for developing nanoparticle-mediated drug delivery. Ther Deliv. Sep. 2010;1(3):411-33.
Demirci, et al. Single cell epitaxy by acoustic picolitre droplets. Lab Chip. Sep. 2007;7(9):1139-45. Epub Jul. 10, 2007.
Depristo et al. A framework for variation discovery and genotyping using next-generation DNA sequencing data. Nature Genet 43:491-498 (2011).
Dey, et al. Integrated Genome and Transcriptome Sequencing from the Same Cell. Nature biotechnology 33.3 (2015): 285-289. PMC. Web. Dec. 18, 2017.
Dhingra, et al. A complete solution for high throughput single cell targeted multiomic DNA and RNA sequencing for cancer research. Poster. AACR 2019.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15):8817-22).
Dressman et al. Transforming single DNA molecules into fluorescent magnetic particles for detection and enumeration of genetic variations. Proc. Natl. Acad. Sci. 2003. 100(15):8817-8822.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Ekblom, R. et al. "A field guide to whole-genome sequencing, assembly and annotation" Evolutionary Apps (Jun. 24, 2014) 7(9):1026-1042.
Ellison, et al., EGFR Mutation Testing in Lung Ancer: A Review of Available Methods and Their Use for Analysis of Tumour Tissue and Cytology Samples, Journal of Clinical Pathology, 2013, 66:79-89.
Ellison et al. Mutations in Active-Site Residues of the Uracil-DNA Glycosytase Encoded by Vaccinia Virus are Incompatible with Virus Viability. J Virology (1996) 70(11):7965-7973.
Epicenter, EZ-Tn5 Transposase, Epicenter, 2012, 1-5. (Year: 2012).

(56) References Cited

OTHER PUBLICATIONS

Epicentre., "EZ-Tn5TM Custom Transposome Construction Kits", http://www.epicentre.com, pp. 1-17, 2012.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-59.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fanielli, M. et al. "Pathology tissue-chromatin immunoprecipitation, coupled with high-throughput sequencing, allows the epigenetic profiling of patient samples" PNAS (2010) 107(50):21535-21540.
Farrukh, et al. Bioconjugating Thiols to Poly(acrylamide) Gels for Cell Culture Using Methylsulfonyl Co-monomers. Angew Chem Int Ed Engl. Feb. 5, 2016;55(6):2092-6. doi: 10.1002/anie.201509986. Epub Jan. 6, 2016.
Fisher, et al. A scalable, fully automated process for construction of sequence-ready human exome targeted capture libraries. Genome Biol. 2011;12(1):R1. doi: 10.1186/GB-2011-12-1-r1. Epub Jan. 4, 2011.
Fox, et al. Accuracy of Next Generation Sequencing Platforms. Next Gener Seq Appl. 2014;1. pii: 1000106.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, et al. A Microfabricated Fluorescence-Activated Cell Sorter. Nature Biotechnology.1999; 17:1109-1111.
Fulton, et al. Advanced multiplexed analysis with the FlowMetrix system. Clin Chem. Sep. 1997;43(9):1749-56.
Gangadharan et al., DNA transposon Hermes insert into DNA in nucleosome-free regions in vivo, Proc nat Ad Sci, Dec. 21, 2010, vol. 107, No. 51, pp. 21966-21972.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci USA. 2001;98:4552-4557.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Gordon et al. "Consed: a Graphical Tool for Sequence Finishing," Genome Research (1998) 8:198-202.
Granieri, Lucia. Droplet-based microfluidics and engineering of tissue plasminogen activator for biomedical applications. Ph.D. Thesis, Nov. 13, 2009 (131 pages).

Grasland-Mongrain, et al. Droplet coalescence in microfluidic devices. Jan.-Jul. 2003. 31 pages. http://www.eleves.ens.fr/home/grasland/rapports/stage4.pdf.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hamady, et al. Error-correcting barcoded primers for pyrosequencing hundreds of samples in multiplex. Nat Methods. Mar. 2008;5(3):235-7. doi: 10.1038/nmeth. 1184. Epub Feb. 10, 2008.
Hamilton, A.J. "microRNA in erythrocytes" Biochem. Soc. Trans. (2010) 38, 229-231.
Han, SW et al. "Targeted Sequencing of Cancer-Related Genes in Colorectal Cancer Using Next-Generation Sequencing" PLOS One (2013) 8(5):e64271.
Han, et al. CRISPR-Cas9 delivery to hard-to-transfect cells via membrane deformation. Science Advances (2015) 1(7): E1500454 (8 pages).
Haring, et al. Chromatin immunoprecipitation: optimization, quantitative analysis and data normalization. Plant Methods. 2007; 3: 11.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hebenstreit. Methods, Challenges and Potentials of Single Cell RNA-seq. Biology (Basel). Nov. 16, 2012;1(3):658-67. doi: 10.3390/biology1030658.
Henke, et al. Enzymatic Crosslinking of Polymer Conjugates is Superior over Ionic or UV Crosslinking for the on-Chip Production of Cell-Laden Microgels. Macromol Biosci. Oct. 2016;16(10):1524-1532. doi: 10.1002/mabi.201600174. Epub Jul. 21, 2016.
Hiatt, et al. Parallel, tag-directed assembly of locally derived short sequence reads. Nat Methods. Feb. 2010;7(2):119-22. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holmberg, et al. The biotin-streptavidin interaction can be reversibly broken using water at elevated temperatures. Feb. 2, 2005. Electrophoresis, 26:501-510.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
Hosono S, et al. Unbiased whole-genome amplification directly from clinical samples. Genome Res. May 2003; 13(5): 954-64. Epub Apr. 14, 2003.
"How many species of bacteria are there" (wisegeek.com; accessed Jan. 21, 2014).
Hu et al., Shape Controllable Microgel Particles Prepared by Microfluidic Combining External Crosslinking, Biomicrofluidics 6:26502 (May 18, 2012).

(56) References Cited

OTHER PUBLICATIONS

Huang et al. EagleView: a genome assembly viewer for next-generation sequencing technologies, Genome Research (2008) 18:1538-1543.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Illumina, Inc. An Introduction to Next-Generation Sequencing Technology. Feb. 28, 2012.
Illumina Nextera Enrichment Sample Preparation Guide. Feb. 2013.
Illumina TruSeq Custom Enrichment Kit Data Sheet. (c) 2014.
Imburgio, et al., "Studies of promoter recognition and start site selection by T7 RNA polymerase using a comprehensive collection of promoter variants", Biochemistry., 39:10419-30, 2000.
Invitrogen Dynal. Dynabeads M-280 Streptavidin 2006 product sheet.
Ioannidis, N. Manufacturing of agarose-based chromatographic adsorbents with controlled pore and particle sizes. a thesis submitted to The University of Birmingham for the degree of Doctor of Philosophy. 2009.
Jarosz, M. et al. "Using 1ng of DNA to detect haplotype phasing and gene fusions from whole exome sequencing of cancer cell lines" Cancer Res (2015) 75(suppl5):4742.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1 to 12822-12. doi: 10.1063/1.3682098. Epub Mar. 15, 2012.
Jiang et al. Cell-laden microfluidic microgels for tissue regeneration. Lab Chip 16(23):4482-4506 (Nov. 2016).
Jin, et al. Genome-wide detection of DNase I hypersensitive sites in single cells and FFPE tissue samples. Nature. Dec. 3, 2015;528(7580):142-6. doi: 10.1038/nature15740.
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Jung, et al. Micro machining of injection mold inserts for fluidic channel of polymeric biochips. Sensors. 2007; 7(8):1643-1654.
Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.
Kanehisa et al. "KEGG: Kyoto Encyclopedia of Genes and Genomes," Nucleic Acids Research (2000) 28:27-30.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.
Katsura, et al. Indirect micromanipulation of single molecules in water-in-oil emulsion. Electrophoresis. Jan. 2001;22(2):289-93.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Kenis, et al. Microfabrication Inside Capillaries Using Multiphase Laminar Flow Patterning. Science. 1999; 285:83-85.
Khomiakova et al., Analysis of perfect and mismatched DNA duplexes by a generic hexanucleotide microchip. Mol Biol(Mosk). Jul.-Aug. 2003;37(4):726-41. Russian. Abstract only.
Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functional microgels in microfluidic devices. Angew Chem Int Ed Engl. 2007;46(11):1819-22.
Kim et al. "HapEdit: an accuracy assessment viewer for haplotype assembly using massively parallel DNA-sequencing technologies," Nucleic Acids Research (2011) pp. W557-W561.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015;161(5):1187-201. doi: 10.1016/j.cell.2015.04.044.
Knapp, et al. Generating barcoded libraries for multiplex high-throughput sequencing. Methods Mol Biol. 2012;840:155-70. doi: 10.1007/978-1-61779-516-9_19.
Knight, et al. Subtle chromosomal rearrangements in children with unexplained mental retardation. Lancet. Nov. 13, 1999;354(9191):1676-81.
Kobayashi, et al. Effect of slot aspect ratio on droplet formation from silicon straight-through microchannels. J Colloid Interface Sci. Nov. 1, 2004;279(1):277-80.
Kolodeziejczyk et al., "The technology and biology of single-cell RNA sequencing", Molecular Cell, vol. 58 (May 21, 2015).
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Kozarewa, et al, "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.
Kukwikila, et al. Assembly of a biocompatible triazole-linked gene by one-pot click-DNA ligation. Nature Chemistry (2017) doi:10.1038/nchem.2850.
Kutyavin, et al. Oligonucleotides containing 2-aminoadenine and 2-thiothymine act as selectively binding complementary agents. Biochemistry. Aug. 27, 1996;35(34):11170-6.
Kwok, et al, "Single-molecule analysis for molecular haplotyping", Hum Mutat., 23:442-6, 2004.
Lagally, et al. Single-Molecular DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Lai; et al, ""Characterization and Use of Laser-Based Lysis for Cell Analysis on-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.
Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis by Transcriptional and Epigenetic States in Human Adult Brain". Apr. 19, 2017. doi: https://doi.org/10.1101/128520.

(56) References Cited

OTHER PUBLICATIONS

Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lander, et al. Initial sequencing and analysis of the human genome. Nature, 409 (Feb. 15, 2001): 860-921.
Lasken, et al. (1996) Archaebacterial DNA Polymerases Tightly Bind Uracil-containing DNA. The Journal of Biological Chemistry, 271(30):17692-17696 (Year: 1996).
Layer et al. "LUMPY: A probabilistic framework for structural variant discovery," Genome Biology (2014) 15(6):R84.
Lebedev, A. et al. "Hot Start PCR with heat-activatable primers: a novel approach for improved PCR performance" NAR (2008) 36(20):E131-1.
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee et al. Alginate: Properties and biomedical applications. Prog Polym Sci 37(1):106-126 (2012).
Lee, et al., "Fluorescent in situ sequencing (FISSEQ) of RNA for gene expression profiling in intact cells and tissues" Nature Protocols (Feb. 12, 2015) 10(3):442-458. XP055272042, GB ISSN:1754-2189, DOI: 10.1038/nprot.2014.191.
Lee, et al., Highly Multiplexed Subcellular RNA Sequencing in Situ. Science 343.6177 (Mar. 2014): 1360-1363, doi: 10.1126/science.1250212.
Lennon et al. A scalable, fully automated process for construction of sequence-ready barcoded libraries for 454. Genome Biology 11:R15 (2010).
Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Li, et al. Fast and accurate long-read alignment with Burrows—Wheeler transform. Bioinformatics 26.5 (2010): 589-595.
Li, et al. Step-emulsification in a microfluidic device. Lab Chip. Feb. 21, 2015;15(4):1023-31. doi: 10.1039/c4lc01289e.
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.
Lippert et al. Algorithmic strategies for the single nucleotide polymorphism haplotype assembly problem, Brief. Bionform (2002) 3:23-31.
"List of sequenced bacterial genomes" (Wikipedia.com; accessed Jan. 24, 2014).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lundin, et al., "Hierarchical molecular tagging to resolve long continuous sequences by massively parallel sequencing", Sci Rep., 3:1186, 2013.
Lupski. Genomic rearrangements and sporadic disease. Nat Genet. Jul. 2007;39(7 Suppl):S43-7.
Maan, et al. Spontaneous droplet formation techniques for monodisperse emulsions preparation—Perspectives for food applications. Journal of Food Engineering. vol. 107, Issues 3-4, Dec. 2011, pp. 334-346.
MaCaulay, et al. G&T-seq: parallel sequencing of single-cell genomes and transcriptomes. Nature Methods, 2015, p. 1-7.
MaCaulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Maeda, et al. Development of a DNA barcode tagging method for monitoring dynamic changes in gene expression by using an ultra high-throughput sequencer. Biotechniques. Jul. 2008;45(1):95-7. doi: 10.2144/000112814.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Mali, et al. Barcoding cells using cell-surface programmable DNA-binding domains. Nat Methods. May 2013;10(5):403-6. doi: 10.1038/nmeth.2407. Epub Mar. 17, 2013.
Mamedov, I.Z., et al. (2013), Preparing unbiased T-cell receptor and antibody cDNA libraries for the deep next generation sequencing profiling, Front Immunol 4: 456.
Man. Monolithic Structures for Integrated Microfluidic Analysis. PhD Thesis. 2001.
Marcus. Gene method offers diagnostic hope. The Wall Street Journal. Jul. 11, 2012.
Margulies 2005 Supplementary methods (Year: 2005).
Margulies et al. "Genome sequencing in microfabricated high-density picoliter reactors", Nature (2005) 437:376-380.
Maricic T, et al. Optimization of 454 sequencing library preparation from small amounts of DNA permits sequence determination of both DNA strands. Biotechniques. Jan. 2009; 46(1):51-2, 54-7.
Marquis, et al. Microfluidics-assisted diffusion self-assembly: toward the control of the shape and size of pectin hydrogel microparticles. Biomacromolecules. May 12, 2014;15(5):1568-78. doi: 10.1021/bm401596m. Epub Apr. 8, 2014.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
McCoy, R. et al. "Illumina TruSeq Synthetic Long-Reads Empower De Novo Assembly and Resolve Complex, Highly-Repetitive Transposable Elements" PLOS (2014) 9(9):e1016689.
McGinnis, et al. MULTI-seq: Scalable sample multiplexing for single-cell RNA sequencing using lipid-tagged indices. bioRxiv (2018) 387241; doi: https://doi.org/10.1101/387241.
McKenna, Aaron et al. "The Genome Analysis Toolkit: a MapReduce Framework for Analyzing next-Generation DNA Sequencing Data." Genome Research 20.9 (2010): 1297-1303. PMC. Web. Feb. 2, 2017.
Merriman, et al. Progress in ion torrent semiconductor chip based sequencing. Electrophoresis. Dec. 2012;33(23):3397-417. doi: 10.1002/elps.201200424.
"Meyer, et al., From micrograms to picograms: quantitative PCR reduces the material demands of high-throughput sequencing, Nucleic Acids Research, 2008, vol. 36, No. 1, 6 pages".
Meyer, et al. Targeted high-throughput sequencing of tagged nucleic acid samples. Nucleic Acids Res. 2007;35(15):e97.
Microfluidic ChipShop. Microfluidic product catalogue. Mar. 2005.
Microfluidic ChipShop. Microfluidic product catalogue. Oct. 2009.
Mignardi, M. et al. "Oligonucleotide gap-fill ligation for mutation detection and sequencing in situ" Nucl Acids Res (2015) 43(22):e151.

(56) References Cited

OTHER PUBLICATIONS

Miller et al. "Assembly Algorithms for next-generation sequencing data," Genomics, 95 (2010), pp. 315-327.
Miller JC, et al. An improved zinc-finger nuclease architecture for highly specific genome editing. Nat. Biotechnol. 2007;25:778-785.
Miller-Stephenson Chemicals 157 FS Series catalog, http://www.miller-stephenon.com. Feb. 6, 2018.
MiRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLOS Comput Biol. 2012;8(12):e1002808. doi: 10.1371/journal.pcbi.1002808. Epub Dec. 27, 2012.
Morimoto, et al. Monodisperse semi-permeable microcapsules for continuous observation of cells. 2009. Lab Chip 9(15):2217-2223.
Morton. Parameters of the human genome. Apr. 23, 1991. Proceedings of the National Academy of Sciences of the United States of America, 88: 7474-7476.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al. "Efficient targeted resequencing of human germline and cancer genomes by oligonucleotide-selective sequencing," Nat Biotechnol, (2011) 29:1024-1027.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Narayanan, J. et al. "Determination of agarose gel pore size: Absorbance measurements vis a vis other techniques" Journal of Physics: Conference Series 28 (2006) 83-86 (Year: 2006).
National Human Genome Research Institute (NHGRI). The Human Genome Project Completion: Frequently Asked Questions. Last Updated: Oct. 30, 2010.
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.

Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production of Monodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al., "Optimizing Illumina next-generation sequencing library preparation for extremely AT-biased genomes", BMC Genomics., 13:1, 2012.
Pantel, et al. Detection methods of circulating tumor cells. J Thorac Dis. Oct. 2012;4(5):446-7. doi: 10.3978/j.issn.2072-1439.2012.08.15.
PARK. ChIP-seq: advantages and challenges of a maturing technology. Nature Reviews Genetics vol. 10, pp. 669-680 (2009).
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Pelton, et al. (2011) Microgels and Their Synthesis: an Introduction, in Microgel Suspensions: Fundamentals and Applications (eds A. Fernandez-Nieves, H. M. Wyss, J. Mattsson and D. A. Weitz), Wiley-VCH Verlag GmbH & Co. KGaA, Weinheim, Germany. doi: 10.1002/9783527632992.ch1.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Pfeifer, et al. Bivalent cholesterol-based coupling of oligonucleotides to lipid membrane assemblies. J Am Chem Soc. Aug. 25, 2004;126(33):10224-5.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
"U.S. Appl. No. 61/982,001, filed Apr. 21, 2014 (Year:2014)".
Pushkarev et al. Single-molecule sequencing of an individual human genome, Nature Biotech (2009) 17:847-850.
Qiagen. Omniscript Reverse Transcription Handbook. Oct. 2010.
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.

(56) References Cited

OTHER PUBLICATIONS

Ran et al. Genome engineering using the CRISPR-Cas9 system. Nature Protocols 8:2281-2308 (2013).
Reis, A. et al. "CRISPR/Cas9 and Targeted Genome Editing: a New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Ritz, A. et al. "Characterization of structural variants with single molecule and hybrid sequencing approaches" Bioinformatics (2014) 30(24):3458-3466.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005UsingMultiplexIdentifierAdaptorsForTheGSFLXTitaniumChemistry-ExtendedMIDSet.pdf.
Rodrigue, S. et al. "Whole genome amplification and de novo assembly of single bacterial cells" PLOS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sahin, et al. Microfluidic EDGE emulsification: the importance of interface interactions on droplet formation and pressure stability. Sci Rep. May 27, 2016;6:26407. doi: 10.1038/srep26407.
Sahiner. Single step poly(L-Lysine) microgel synthesis, characterization and biocompatibility tests. Polymer, vol. 121, Jul. 14, 2017, pp. 46-54.
Sakaguchi, et al. (1996) Cautionary Note on the Use of dUMP-Containing PCR Primers with Pfu and VentR. Biotechniques, 21(3): 368-370 (Year: 1996).
Sander JD, et al. Selection-free zinc-finger-nuclease engineering by context-dependent assembly (CoDA). Nat. Methods. 2011;8:67-69.
Savva, et al. The structural basis of specific base-excision repair by uracil-DNA glycosylase. Nature. Feb. 9, 1995;373(6514):487-93.
Schirinzi et al., Combinatorial sequencing-by-hybridization: Analysis of the NF1 gene. Genet Test. 2006 Spring;10(1):8-17.
Schmieder, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Seiffert, et al. Microfluidic fabrication of smart microgels from macromolecular precursors.Polymer. vol. 51, Issue 25, Nov. 26, 2010, pp. 5883-5889.
Seiffert, et al. Smart microgel capsules from macromolecular precursors. J Am Chem Soc. May 12, 2010;132(18):6606-9. doi: 10.1021/ja102156h.
Seiffert. Microgel capsules tailored by droplet-based microfluidics. Chemphyschem. Feb. 4, 2013;14(2):295-304. doi: 10.1002/cphc.201200749. Epub Dec. 6, 2012.
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shaikh, et al. A modular microfluidic architecture for integrated biochemical analysis. Proc Natl Acad Sci U S A. Jul. 12, 2005;102(28):9745-50. Epub Jun. 28, 2005.
Shelbourne et al., "Fast copper-free click DNA ligation by the ring-strain promoted alkyne-azide cycloaddition reaction," Chem. Commun., 2011, 47, 6257-6259.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Shih, et al. Photoclick Hydrogels Prepared from Functionalized Cyclodextrin and Poly(ethylene glycol) for Drug Delivery and in Situ Cell Encapsulation. Biomacromolecules. Jul. 13, 2015;16(7):1915-23. doi: 10.1021/acs.biomac.5b00471. Epub Jun. 3, 2015.
Shimkus, et al. A chemically cleavable biotinylated nucleotide: usefulness in the recovery of protein-DNA complexes from avidin affinity cols. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Simon, et al., "Using formaldehyde-assisted isolation of regulatory elements (FAIRE) to isolate active regulatory DNA", Nature Protocols, 2012, 7(2): 256-267.
Smith, et al. Highly-multiplexed barcode sequencing: an efficient method for parallel analysis of pooled samples. Nucleic Acids Research, 38(13): e142 (2010).
Song, et al., "DNase-seq: a High-Resolution Technique for Mapping Active Gene Regulatory Elements across the Senome from Mammalian Cells", Cold Spring Harbor Laboratory Press, 2010, 2010(2), doi:10.1101/pdb.prot5384.
Song, et al. Reactions in droplets in microfluidic channels. Angew Chem Int Ed Engl. Nov. 13, 2006;45(44):7336-56.

(56) References Cited

OTHER PUBLICATIONS

Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Spitale et al., "Structural imprints in vivo decode RNA regulatory mechanisms," Nature. Mar. 26, 2015;519(7544):486-90; doi: 10.1038/nature14263. Epub Mar. 18, 2015.
Spormann Laboratory, Polymerase Chain Reaction (PCR), Alfred Spormann Laboratory, 2009, 1-3. (Year: 2009).
SSH Tunnel—Local and Remote Port Forwarding Explained With Examples, Trackets Blog, http://blog.trackets.com/2014/05/17/ssh-tunnel-local-and-remote-port-forwarding-explained with-examples.html; Retrieved from the Internet Jul. 7, 2016.
Stoeckius, et al. Large-scale simultaneous measurement of epitopes and transcriptomes in single cells. bioRxiv 113068; doi: https://doi.org/10.1101/113068; (Mar. 2, 2017).
Stoeckius, et al. Simultaneous epitope and transcriptome measurement in single cells. Nature methods. Jul. 31, 2017.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tam, et al. Engineering Cellular Microenvironments with Photo- and Enzymatically Responsive Hydrogels: Toward Biomimetic 3D Cell Culture Models. Acc Chem Res. Apr. 18, 2017;50(4):703-713. doi: 10.1021/acs.accounts.6b00543. Epub Mar. 27, 2017.
Tawfik, D.S., et al., "Man-made cell-like compartments for molecular evolution," Nature Biotechnology, vol. 16, pp. 652-656 (1998).
Tayyab, S. et al. Size exclusion chromatography and size exclusion HPLC of proteins. Biochem Ed, Pergamon. 19(3):149-152 (1991).
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Tewhey et al. The importance of phase information for human genomics, Nat Rev Genet (2011) 12:215-223.
Thaxton, C.S. et al. "A Bio-Bar-Code Assay Based Upon Dithiothreitol Oligonucleotide Release" Anal Chem (2005) 77:8174-8178.
The SAM/BAM Format Specificatio Working Group, "Sequence Allignment/ Map Format Specification," Sep. 6, 2016.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thermofisher, Protocols, M-270 Streptavidin, ThermoFisherScientific, 2007, 1-5. (Year: 2007).
Thorsen, et al. Dynamic pattern formation in a vesicle-generating microfluidic device. Physical Review Letters. American Physical Society. 2001; 86(18):4163-4166.
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1) 107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ullal et al. Cancer Cell Profiling by Barcoding Allows Multiplexed Protein Analysis in Fine-Needle Aspirates. Sci Transl Med. Jan. 15, 2014; 6(219): 219ra9.
Umbanhowar, P.B., et al., "Monodisperse Emulsion Generation via Drop Break off in a Coflowing Stream," Langmuir, vol. 16, pp. 347-351 (2000).
Ushijima et al, Detection and interpretation of altered methylation patterns in cancer cells, 2005, Nature reviews, 5, 223-231.
Uttamapinant, et al. Fast, cell-compatible click chemistry with copper-chelating azides for biomolecular labeling.Angew. Chem. Int. End. Engl., Jun. 11, 2012: 51(24) pp. 5852-5856.
Van Dijke, et al. Effect of viscosities of dispersed and continuous phases in microchannel oil-in-water emulsification . Microfluid Nanofluid (2010) 9: 77. https://doi.org/10.1007/s10404-009-0521-7.
Van Nieuwerburgh, et al, "Illumina mate-paired DNA sequencing-library preparation using Cre-Lox recombination", Nucleic Acids Res., 40:1-8, 2012.
Velasco, et al. Microfluidic encapsulation of cells in polymer microgels. Small. Jun. 11, 2012;8(11):1633-42. doi: 10.1002/smll.201102464. Epub Mar. 29, 2012.
Voskoboynik, A. et al. The genome sequence of the colonial chordate, Botryllus schlosseri. eLife, 2:e00569 (2013). doi: 10.7554/eLife.00569. Epub Jul. 2, 2013.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25): 16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Wheeler et al., "Database resources of the National Center for Biotechnology Information," Nucleic Acids Res. (2007) 35 (Database issue): D5-12.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled by CombiGEM. PNAS. Mar. 1, 2016, vol. 113, pp. 2544-2549.

(56) References Cited

OTHER PUBLICATIONS

Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLOS One. Jul. 19, 2017;12(7):e0181163. doi: 10.1371/journal.pone.0181163. eCollection 2017.
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xiao, et al., "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zentner, et al. Surveying the epigenomic landscape, one base at a time. Genome Biol. Oct. 22, 2012;13(10):250. doi: 10.1186/gb4051.
Zerbino, Daniel, "Velvet Manual—version 1.1," Aug. 15, 2008, pp. 1-22.
Zerbino, D.R. "Using the Velvet de novo assembler for short-read sequencing technologies" Curr Protoc Bioinformatics. Sep. 2010;Chapter 11:Unit 11.5. doi: 10.1002/0471250953.bi1105s31.
Zerbino et al. "Velvet: Algorithms for de novo short read assembly using de Bruijn graphs," Genome Research (2008) 18:821-829.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang, et al. One-step fabrication of supramolecular microcapsules from microfluidic droplets. Science. Feb. 10, 2012;335(6069):690-4. doi: 10.1126/science.1215416.
Zhang, et al. Reconstruction of DNA sequencing by hybridization. Bioinformatics. Jan. 2003;19(1):14-21.
Zhang F, et al. Efficient construction of sequence-specific TAL effectors for modulating mammalian transcription. Nat. Biotechnol. 2011;29:149-153.
Zhang. Genomics of inherited bone marrow failure and myelodysplasia. Dissertation [online]. University of Washington. 2015 [Retrieved on May 3, 2017].
Zhang, H. et al. Massively Parallel Single-Molecule and Single-Cell Emulsion Reverse Transcription Polymerase Chain Reaction using Agarose Droplet Microfluidics. Anal Chem (2012) 84:3599-3606.
Zhang, H. et al. "Massively Parallel Single-Molecule and Single-Cell Emulsion Reverse Transcription Polymerase Chain Reaction using Agarose Droplet Microfluidics" Anal Chem (2012) 84:3599-3606, Supporting Information.
Zhao, J., et al., "Preparation of hemoglobin-loaded Nano-sized particles with porous structure as oxygen carriers," Biomaterials, vol. 28, pp. 1414-1422 (2007).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Reverse transcriptase template switching: a SMART approach for full-length cDNA library construction. Biotechniques. Apr. 2001;30(4):892-7.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypo-osmolar electrofusion. Hum. Antibodies Hybridomas. Jan. 1992;3 (1): 14-8.
Zong et al. Genome-Wide Detection of Single Nucleotide and Copy Number Variations of a Single Human Cell. Science 338(6114):1622-1626 (2012).
Co-pending U.S. Appl. No. 18/152,650, inventor Shastry; Shankar, filed Jan. 10, 2023.

Plate 1 - Well A1 - TruSeq Oligo

R1
Part A
Part S (Alpha C8)
Part B (Alpha C8)
Part D
Shared 10X BC

Plate 1 - Well A1 - Nextera Oligo

R1
Part A
Part S (Beta C8)
Part B (Beta C8), Capture Sequence
Part D
Shared 10X BC

TruSeq pR1
Part A
Part S (Alpha OH)
Part B (Alpha OH)
Part D (Theta OH)
Part C (Theta OH), Poly(dT)
Part T CTACACGACGCTCTT...TGGATGAT(N1)₁₀TTTTTTTTTTTTTTTTTTTTTTTVN
GCGAGAAGGCTAGATGAGTCAAGTACGAACCTACTA

FIG. 17

Nxt pR1
Part A
Part S (Beta OH)
Part B (Beta OH)
Part D (Eta OH)
Part C (Eta OH), Capture Sequence
Part T GTCAGAATGTGTAAAA[...]ACGATGAT(N1)₁₀TTGCTAGGACCGGCTTAAAGC
CACATATTCTTCTGTCTGAGTCGT[...]TGCTACTA

SEQUENCE LISTING

```
<160> NUMBER OF SEQ ID NOS: 208

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgccttgtaa cgcgaa                                                         16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```

```
tatggccgcg caatta                                                    16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttcgagcgcg caatta                                                    16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
attgcgccga acgtat                                                    16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gttgcacgcg caatta                                                    16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgccattgcg cgataa                                                    16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaggatcgcg cctatt                                                    16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
```

```
gttacgcgcg caatta                                                         16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agcatgtcgc gcatta                                                         16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttcgcaacgg tcgaat                                                         16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
attgcgcgcg aattac                                                         16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcttagcgga cgcaat                                                         16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atccatggcg cgatta                                                         16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gttcgcacgc gaatta                                                         16
```

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgattgcgcg acatta                                                      16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgatcgcgct acgaat                                                      16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgcattcaat tggcga                                                      16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aacgttcgcg attgac                                                      16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcttgaccgc gaatta                                                      16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
actgcgcgat tcgtaa                                                      16

```
<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tccaataatg cgcggt                                                      16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agtcatcgac cggatt                                                      16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agacttcgcg cgatta                                                      16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgagtcgcg caatta                                                      16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tcgctaacgg tcgaat                                                      16

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tatgcgcgcg aattac                                                      16
```

```
<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tatgcgcgct acgaat                                                        16

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aactgcgcga ttcgta                                                        16

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tggaccgcgc atatta                                                        16

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tatcacaatg cgcggt                                                        16

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtcacgcgcg aattat                                                        16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtctagcgcg caatta                                                        16

<210> SEQ ID NO 33
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tctgcaacgg tcgaat                                                    16

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccagtgcgcg aattat                                                    16

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atcgtcacgc gattag                                                    16

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gccaatcgac gttagt                                                    16

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttagcgcgcg aattac                                                    16

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcgatcagtt acgcga                                                    16

<210> SEQ ID NO 39
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
acctgaatac gcggtt                                                       16

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tgcggtcgaa cctaat                                                       16

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgaacgcgct actatg                                                       16

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tggcttaatc gcgaca                                                       16

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
taggtccgcg acatta                                                       16

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccttggcgaa cgatta                                                       16

<210> SEQ ID NO 45
<211> LENGTH: 16
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 45
aagtccgcgc gattat                                                   16

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gactgtcgcg caatta                                                   16

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttaggtccgc tacgaa                                                   16

<210> SEQ ID NO 48
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tctgtgaacc gtcgaa                                                   16

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtcacaatac gcggtt                                                   16

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gagacttcgc gcatta                                                   16

<210> SEQ ID NO 51
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 51
gagcaattcg cgctat                                                    16

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cgttacgatt acgcga                                                    16

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
agcacgtaat cgttcg                                                    16

<210> SEQ ID NO 54
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gcgttaccga acgtat                                                    16

<210> SEQ ID NO 55
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttaacgaccg gttacg                                                    16

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
attgcgcgcg atacta                                                    16

<210> SEQ ID NO 57
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 57
ctgttgaccg cgaata                                                    16

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gcaagattcg cgctat                                                    16

<210> SEQ ID NO 59
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggccatcgcg aattat                                                    16

<210> SEQ ID NO 60
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
atggaccgcg ctatta                                                    16

<210> SEQ ID NO 61
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
acgcgataat cgttcg                                                    16

<210> SEQ ID NO 62
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
taggcattat ccgcga                                                    16

<210> SEQ ID NO 63
<211> LENGTH: 16
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 63
tcagctcgaa cggtta                                              16

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cattcaattg cgcgag                                              16

<210> SEQ ID NO 65
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gctcaattac gcggat                                              16

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
acggatcgca tcgtta                                              16

<210> SEQ ID NO 67
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ctgcaattac gcggat                                              16

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgtcgattac gcgaac                                              16

<210> SEQ ID NO 69
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 69
acctaggcgc gattat                                                    16

<210> SEQ ID NO 70
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cgcgtagcgc atatta                                                    16

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caatcgttac gcggat                                                    16

<210> SEQ ID NO 72
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
taacgcttac gcggat                                                    16

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gctaacgcga ttcgta                                                    16

<210> SEQ ID NO 74
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
attcctaatg cgcgag                                                    16

<210> SEQ ID NO 75
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 75
ttcactaatg cgcgag                                                        16

<210> SEQ ID NO 76
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
caaggattcg cgctat                                                        16

<210> SEQ ID NO 77
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
acgattcgac cggtat                                                        16

<210> SEQ ID NO 78
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gagcaactat tcgcgt                                                        16

<210> SEQ ID NO 79
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tacctacgat tgcgag                                                        16

<210> SEQ ID NO 80
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
taatcgaccg gttacg                                                        16

<210> SEQ ID NO 81
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gttcacaata cgcggt                                              16

<210> SEQ ID NO 82
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gctagcgcgc atatta                                              16

<210> SEQ ID NO 83
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
actgacttac gcggat                                              16

<210> SEQ ID NO 84
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gcacgttcgc gtaata                                              16

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aaggtccgcg ctatta                                              16

<210> SEQ ID NO 86
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ctagtgaacg cgctat                                              16

<210> SEQ ID NO 87
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ggccatcgat tcgtaa                                               16

<210> SEQ ID NO 88
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
accttgcgcg atagta                                               16

<210> SEQ ID NO 89
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctaggtccgc gaatta                                               16

<210> SEQ ID NO 90
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
atatcgaccg gttacg                                               16

<210> SEQ ID NO 91
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
atagcttatg cgcgac                                               16

<210> SEQ ID NO 92
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
acgttaatcg gtacgc                                               16

<210> SEQ ID NO 93
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
catcatcgat tgcgag                                               16

<210> SEQ ID NO 94
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gtaactcgac cggatt                                                   16

<210> SEQ ID NO 95
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tcgaacgcgt attagc                                                   16

<210> SEQ ID NO 96
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tagtcgaccg attacg                                                   16

<210> SEQ ID NO 97
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gatcacgcga ttcgta                                                   16

<210> SEQ ID NO 98
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
agttagcgtt acgacc                                                   16

<210> SEQ ID NO 99
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gctcaataag tcgcgt                                                   16

<210> SEQ ID NO 100
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cttaggcgcg aattac                                                   16

<210> SEQ ID NO 101
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
taggtcacgt tacgac                                                   16

<210> SEQ ID NO 102
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ataccttatg cgcgag                                                   16

<210> SEQ ID NO 103
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcacgatagt tcgcta                                                   16

<210> SEQ ID NO 104
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gtcatacaat tcgcgg                                                   16

<210> SEQ ID NO 105
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cgactattat gcgcga                                                   16

```
<210> SEQ ID NO 106
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
taagccgcgt attagc                                                      16

<210> SEQ ID NO 107
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cgaattcgac cggtat                                                      16

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cgtcaataat cgcgtg                                                      16

<210> SEQ ID NO 109
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggaaccttaa tcgcgt                                                      16

<210> SEQ ID NO 110
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gctcaataat cgcgtg                                                      16

<210> SEQ ID NO 111
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ccaatgcgcg ttagta                                                      16

<210> SEQ ID NO 112
```

-continued

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gaacttcgac cggtat                                                   16

<210> SEQ ID NO 113
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
cgcttaatcg aacggt                                                   16

<210> SEQ ID NO 114
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ccttgagtcg aacgat                                                   16

<210> SEQ ID NO 115
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atcgagtaac cgttcg                                                   16

<210> SEQ ID NO 116
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
taccgtaacg tagtcg                                                   16

<210> SEQ ID NO 117
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gttctcatcg aacgga                                                   16

<210> SEQ ID NO 118
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atcttgaatc gcgacg                                                    16

<210> SEQ ID NO 119
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
agaccttaat cgcgtg                                                    16

<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gaccaatatg tcgcgt                                                    16

<210> SEQ ID NO 121
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cgtaatcgac cggtat                                                    16

<210> SEQ ID NO 122
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtacactaag tcgcgt                                                    16

<210> SEQ ID NO 123
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tagtaccgat tgaccg                                                    16

<210> SEQ ID NO 124
<211> LENGTH: 16
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 124
agtctaatcg gtacgc                                                    16

<210> SEQ ID NO 125
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gtactgaccg attacg                                                    16

<210> SEQ ID NO 126
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ccttgaatcg aacggt                                                    16

<210> SEQ ID NO 127
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tcgactaatc ggtacg                                                    16

<210> SEQ ID NO 128
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gcggattacg ctacta                                                    16

<210> SEQ ID NO 129
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ccttagtagt acgcga                                                    16

<210> SEQ ID NO 130
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 130
ccttaagtta cgcgag                                                         16

<210> SEQ ID NO 131
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gtaagtacgc gctatc                                                         16

<210> SEQ ID NO 132
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ctgtcgcgat cgataa                                                         16

<210> SEQ ID NO 133
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggacaatcgc tcgtta                                                         16

<210> SEQ ID NO 134
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gtccgtcgat cgataa                                                         16

<210> SEQ ID NO 135
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gacttacgac cggtat                                                         16

<210> SEQ ID NO 136
<211> LENGTH: 16
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 136
ctgttaatcg accgga                                                      16

<210> SEQ ID NO 137
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
atgcggtaac ctatcg                                                      16

<210> SEQ ID NO 138
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
agatagttac gcgtcc                                                      16

<210> SEQ ID NO 139
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gagtccaact atcggt                                                      16

<210> SEQ ID NO 140
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ttacagtact agcggc                                                      16

<210> SEQ ID NO 141
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gactaatacg cgttcg                                                      16

<210> SEQ ID NO 142
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
tggtaactat accggc                                                      16

<210> SEQ ID NO 143
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cgtacgtaac tatcgg                                                      16

<210> SEQ ID NO 144
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gaccttaatc ggtacg                                                      16

<210> SEQ ID NO 145
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
cattaccgga tagtcg                                                      16

<210> SEQ ID NO 146
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gatagttatc gcaccg                                                      16

<210> SEQ ID NO 147
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
actagtcgta cgatgc                                                      16

<210> SEQ ID NO 148
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 148
gatcactaat cgcgtg                                                    16

<210> SEQ ID NO 149
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gcgttacgct aatacg                                                    16

<210> SEQ ID NO 150
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cacgatcgta cggtat                                                    16

<210> SEQ ID NO 151
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tgtacgtacg atccga                                                    16

<210> SEQ ID NO 152
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ctagactaat cgcgtg                                                    16

<210> SEQ ID NO 153
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
catagtcgta cgatgc                                                    16

<210> SEQ ID NO 154
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 154
gtcgactaac tatcgg         16

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ccttagccgc taataggtga gc         22

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ttgctaggac cggccttaaa gc         22

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gaggattgcg caccttacta gc         22

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
caactttagc ggtccaaggt gc         22

<210> SEQ ID NO 159
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
acgctagttt cgcgtacgaa gc         22

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
acgctagttt cgcgtacgaa gc                                              22

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gaggattgcg caccttacta gc                                              22

<210> SEQ ID NO 162
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ttgctaggac cggccttaaa gc                                              22

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gacaattgtc ggctcgacta gc                                              22

<210> SEQ ID NO 164
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, t, g, unknown or other

<400> SEQUENCE: 164
tttttttttt tttttttttt tttttttttt vn                                   32

<210> SEQ ID NO 165
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(48)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other

<400> SEQUENCE: 165
ctacacgacg ctcttccgat ctagtaaccg tcacgctgnn nnnnnnnntt tttttttttt     60
tttttttttt tttttttttvn                                                        80

<210> SEQ ID NO 166
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cagcgtgacg gttactagat cggaagagcg                                              30

<210> SEQ ID NO 167
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(48)
<223> OTHER INFORMATION: a, c, t, g, unknown or other

<400> SEQUENCE: 167
gtcagatgtg tataagagac agagtaaccc acacgctgnn nnnnnnnntt gctaggaccg             60
gccttaaagc                                                                    70

<210> SEQ ID NO 168
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
cagcgtgtgg gttactctgt ctcttataca c                                            31

<210> SEQ ID NO 169
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ctacacgacg ctctt                                                              15

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other

<400> SEQUENCE: 170
ctacacgacg ctcttccgat ctnnnnnn                                                28

```
<210> SEQ ID NO 171
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other

<400> SEQUENCE: 171
acnnnnnnag atcggaagag cg                                              22

<210> SEQ ID NO 172
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(48)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other

<400> SEQUENCE: 172
ctacacgacg ctcttccgat ctnnnnnngt nnnnnnnnnn nnnnnnnntt tttttttttt     60
tttttttttt tttttttttvn                                                80

<210> SEQ ID NO 173
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (11)..(16)
<223> OTHER INFORMATION: a, c, t, g, unknown or other

<400> SEQUENCE: 173
nnnnnnnnac nnnnnnagat cggaagagcg                                      30

<210> SEQ ID NO 174
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(48)
```

<223> OTHER INFORMATION: a, c, t, g, unknown or other

<400> SEQUENCE: 174
ctacacgacg ctcttccgat ctnnnnnngt nnnnnnnnnn nnnnnnnntt gctaggaccg    60
gccttaaagc                                                           70

<210> SEQ ID NO 175
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other

<400> SEQUENCE: 175
gtcagatgtg tataagagac agnnnnnnn                                      29

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 176
tgnnnnnnnc tgtctcttat acac                                           24

<210> SEQ ID NO 177
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (11)..(17)
<223> OTHER INFORMATION: a, c, t, g, unknown or other

<400> SEQUENCE: 177
nnnnnnnntg nnnnnnnctg tctcttatac ac                                  32

<210> SEQ ID NO 178
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(54)
<223> OTHER INFORMATION: a, c, t, g, unknown or other
<220> FEATURE:
<221> NAME/KEY: modified_base
<222> LOCATION: (86)..(86)
<223> OTHER INFORMATION: a, c, t, g, unknown or other

<400> SEQUENCE: 178
ctacacgacg ctcttccgat ctactcaggt cgctcgtgga tgatnnnnnn nnnnttttt      60 tttttttttt tttttttttt ttttvn                                          86

<210> SEQ ID NO 179
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
atcatccacg agcgacctga gtagatcgga agagcg                               36

<210> SEQ ID NO 180
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(54)
<223> OTHER INFORMATION: a, c, t, g, unknown or other

<400> SEQUENCE: 180
gtcagatgtg tataagagac agactcagca cgctcgacga tgatnnnnnn nnnnttgcta      60
ggaccggcct taaagc                                                     76

<210> SEQ ID NO 181
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
atcatcgtcg agcgtgctga gtctgtctct tatacac                              37

<210> SEQ ID NO 182
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(54)
<223> OTHER INFORMATION: a, c, t, g, unknown or other
<220> FEATURE:
<221> NAME/KEY: modified_base
<222> LOCATION: (86)..(86)
<223> OTHER INFORMATION: a, c, t, g, unknown or other

<400> SEQUENCE: 182
ctacacgacg ctcttccgat ctactcaggt cgctcgtgga tgatnnnnnn nnnnttttt      60 tttttttttt tttttttttt ttttvn                                          86

<210> SEQ ID NO 183
<211> LENGTH: 36
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 183
atcatccacg agcgacctga gtagatcgga agagcg                36

<210> SEQ ID NO 184
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (45)..(54)
<223> OTHER INFORMATION: a, c, t, g, unknown or other

<400> SEQUENCE: 184
gtcagatgtg tataagagac agactcagca cgctcgacga tgatnnnnnn nnnnttgcta        60
ggaccggcct taaagc        76

<210> SEQ ID NO 185
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 185
atcatcgtcg agcgtgctga gtctgtctct tatacac        37

<210> SEQ ID NO 186
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 186
gtcagatgtg tataa        15

<210> SEQ ID NO 187
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (30)..(36)
<223> OTHER INFORMATION: a, c, t, g, unknown or other

<400> SEQUENCE: 187
ctacacgacg ctcttccgat ctnnnnnngt nnnnnn        36

<210> SEQ ID NO 188
<211> LENGTH: 30
<212> TYPE: DNA

-continued

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other
<220> FEATURE:
<221> NAME/KEY: modified_base
<222> LOCATION: (11)..(16)
<223> OTHER INFORMATION: a, c, t, g, unknown or other

<400> SEQUENCE: 188
cannnnnnac nnnnnnagat cggaagagcg                                      30

<210> SEQ ID NO 189
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (31)..(37)
<223> OTHER INFORMATION: a, c, t, g, unknown or other

<400> SEQUENCE: 189
gtcagatgtg tataagagac agnnnnnnnc annnnnn                              37

<210> SEQ ID NO 190
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other
<220> FEATURE:
<221> NAME/KEY: modified_base
<222> LOCATION: (11)..(17)
<223> OTHER INFORMATION: a, c, t, g, unknown or other

<400> SEQUENCE: 190
gtnnnnnntg nnnnnnnctg tctcttatac ac                                   32

<210> SEQ ID NO 191
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (32)..(37)
<223> OTHER INFORMATION: a, c, t, g, unknown or other
<220> FEATURE:
<221> NAME/KEY: modified_base
<222> LOCATION: (40)..(55)
<223> OTHER INFORMATION: a, c, t, g, unknown or other
```

<400> SEQUENCE: 191
gtcagatgtg tataagagac agnnnnnnnc annnnnnacn nnnnnnnnnn nnnnncctta    60
gccgctaata ggtgagc                                                  77

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
aaaaaaaaaa aaaaaaaaaa                                               20

<210> SEQ ID NO 193
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
atcctagcaa                                                          10

<210> SEQ ID NO 194
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (53)..(59)
<223> OTHER INFORMATION: a, c, t, g, unknown or other
<220> FEATURE:
<221> NAME/KEY: modified_base
<222> LOCATION: (62)..(67)
<223> OTHER INFORMATION: a, c, t, g, unknown or other
<220> FEATURE:
<221> NAME/KEY: modified_base
<222> LOCATION: (70)..(85)
<223> OTHER INFORMATION: a, c, t, g, unknown or other

<400> SEQUENCE: 194
cgatgacgtt aatacgactc actatagggja ctacacgacg ctcttccgat ctnnnnnnng    60
tnnnnnntgn nnnnnnnnnn nnnnn                                         85

<210> SEQ ID NO 195
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (53)..(58)
<223> OTHER INFORMATION: a, c, t, g, unknown or other
<220> FEATURE:
<221> NAME/KEY: modified_base
<222> LOCATION: (61)..(66)
<223> OTHER INFORMATION: a, c, t, g, unknown or other

```
<220> FEATURE:
<221> NAME/KEY: modified_base
<222> LOCATION: (69)..(75)
<223> OTHER INFORMATION: a, c, t, g, unknown or other

<400> SEQUENCE: 195
cgatgacgtt aatacgactc actataggga ctacacgacg ctcttccgat ctnnnnnngt    60
nnnnnntgnn nnnnntttct tatatggg                                      88

<210> SEQ ID NO 196
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(54)
<223> OTHER INFORMATION: a, c, t, g, unknown or other

<400> SEQUENCE: 196
gtcagatgtg tataagagac agactcagca cgctcgacga tgatnnnnnn nnnnttgcta    60
ggaccggcct taaagc                                                   76

<210> SEQ ID NO 197
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
atcatcgtcg agcgtgctga gtctgtctct tatacacatc tgac                    44

<210> SEQ ID NO 198
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(54)
<223> OTHER INFORMATION: a, c, t, g, unknown or other
<220> FEATURE:
<221> NAME/KEY: modified_base
<222> LOCATION: (86)..(86)
<223> OTHER INFORMATION: a, c, t, g, unknown or other

<400> SEQUENCE: 198
ctacacgacg ctcttccgat ctactcaggt cgctcgtgga tgatnnnnnn nnnntttttt    60
tttttttttt tttttttttt ttttvn                                        86

<210> SEQ ID NO 199
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
atcatccacg agcgacctga gtagatcgga agagcgtcgt gtag                    44
```

<210> SEQ ID NO 200
<211> LENGTH: 53
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<221> NAME/KEY: modified_base
<222> LOCATION: (22)..(28)
<223> OTHER INFORMATION: a, c, t, g, unknown or other
<220> FEATURE:
<221> NAME/KEY: modified_base
<222> LOCATION: (31)..(36)
<223> OTHER INFORMATION: a, c, t, g, unknown or other
<220> FEATURE:
<221> NAME/KEY: modified_base
<222> LOCATION: (39)..(53)
<223> OTHER INFORMATION: a, c, t, g, unknown or other

<400> SEQUENCE: 200
ctacacgacg ctcttcgatc tnnnnnnngt nnnnnntgnn nnnnnnnnnn nnn            53

<210> SEQ ID NO 201
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
aagagcgtcg tgtag                                                       15

<210> SEQ ID NO 202
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(13)
<223> OTHER INFORMATION: a, c, t, g, unknown or other

<400> SEQUENCE: 202
ccgatctnnn nnn                                                         13

<210> SEQ ID NO 203
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(35)
<223> OTHER INFORMATION: a, c, t, g, unknown or other

<400> SEQUENCE: 203
ctacacgacg ctcttccgat ctnnnnnngt nnnnn                                 35

<210> SEQ ID NO 204
<211> LENGTH: 29

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(7)
<223> OTHER INFORMATION: a, c, t, g, unknown or other
<220> FEATURE:
<221> NAME/KEY: modified_base
<222> LOCATION: (10)..(15)
<223> OTHER INFORMATION: a, c, t, g, unknown or other

<400> SEQUENCE: 204
cannnnnacn nnnnnagatc ggaagagcg                                          29

<210> SEQ ID NO 205
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(36)
<223> OTHER INFORMATION: a, c, t, g, unknown or other
<220> FEATURE:
<221> NAME/KEY: modified_base
<222> LOCATION: (39)..(54)
<223> OTHER INFORMATION: a, c, t, g, unknown or other

<400> SEQUENCE: 205
ctacacgacg ctcttccgat ctnnnnnngt nnnnnntgnn nnnnnnnnnn nnnntttctt        60
atatggg                                                                  67

<210> SEQ ID NO 206
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (9)..(14)
<223> OTHER INFORMATION: a, c, t, g, unknown or other
<220> FEATURE:
<221> NAME/KEY: modified_base
<222> LOCATION: (17)..(22)
<223> OTHER INFORMATION: a, c, t, g, unknown or other

<400> SEQUENCE: 206
nnnnnncann nnnnacnnnn nnagatcgga agagcg                                  36

<210> SEQ ID NO 207
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide
<220> FEATURE:
<221> NAME/KEY: modified_base
<222> LOCATION: (3)..(18)
<223> OTHER INFORMATION: a, c, t, g, unknown or other

<400> SEQUENCE: 207
tgnnnnnnnn nnnnnnnntt tcttatatgg g                              31

<210> SEQ ID NO 208
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (32)..(49)
<223> OTHER INFORMATION: a, c, t, g, unknown or other

<400> SEQUENCE: 208
gtcagatgtg tataagagac agnnnnnnnc annnnnnnnn nnnnnnnnnt tgctaggacc    60
ggccttaaag c                                                         71
```

FUNCTIONALIZED GEL BEADS

CROSS REFERENCE

This application is a continuation of U.S. application Ser. No. 16/680,343, filed Nov. 11, 2019, which is a continuation of U.S. application Ser. No. 16/230,936, filed Dec. 21, 2018, now U.S. Pat. No. 10,745,742, which is a continuation of International Patent Application No. PCT/US2018/061391, filed Nov. 15, 2018, which claims the benefit of U.S. Provisional Application No. 62/586,784, filed Nov. 15, 2017, and U.S. Provisional Application No. 62/629,561, filed Feb. 12, 2018, each of which applications is entirely incorporated herein by reference.

SEQUENCE LISTING

The instant application contains a Sequence Listing which has been submitted electronically in ASCII format and is hereby incorporated by reference in its entirety. Said ASCII copy, created on Mar. 29, 2019, is named 43487-786_301_SL.txt and is 55,855 bytes in size.

BACKGROUND

Samples may be processed for various purposes, such as identification of a type of moiety within the sample. The sample may be a biological sample. The biological samples may be processed for various purposes, such as detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

The present disclosure provides methods for use in various sample processing and analysis applications. The methods provided herein may provide barcode molecules comprising one or more sequences such as a barcode sequence and a functional sequence. Barcode molecules may be attached to supports such as beads. Such methods may employ combinatorial (e.g., split pool) ligation reactions and may be useful, for example, in controlled analysis and processing of analytes such as biological particles, nucleic acid molecules, proteins, and perturbation agents.

In an aspect, the present disclosure provides a method for generating a plurality of barcode molecules, comprising: (a) providing a plurality of molecules coupled to a plurality of supports; and combinatorially assembling the plurality of barcode molecules coupled to the plurality of supports by coupling one or more molecules each comprising one or more segments to each of the plurality of molecules, wherein the plurality of barcode molecules comprises (i) a first set of barcode molecules coupled to a support of the plurality of supports and (ii) a second set of barcode molecules coupled to the support, wherein barcode molecules of the first set of barcode molecules are different than barcode molecules of the second set of barcode molecules.

In some embodiments, the barcode molecules of the first set of barcode molecules and the barcode molecules of the second set of barcode molecules comprise barcode sequences that are different from barcode sequences of barcode molecules coupled to other supports of the plurality of supports.

In some embodiments, barcode sequences of the barcode molecules of the first set of barcode molecules and the barcode molecules of the second set of barcode molecules are identical.

In some embodiments, the plurality of supports is a plurality of beads, and wherein the barcode molecules of the first set of barcode molecules and the barcode molecules of the second set of barcode molecules are coupled to a bead of the plurality of beads. In some embodiments, at least a subset of the barcode molecules of the first set of barcode molecules and/or the barcode molecules of the second set of barcode molecules is coupled to an interior of the bead. In some embodiments, the barcode molecules of the first set of barcode molecules and the barcode molecules of the second set of barcode molecules are releasably coupled to the bead. In some embodiments, the barcode molecules of the first set of barcode molecules and the barcode molecules of the second set of barcode molecules are releasably coupled to the bead through chemical cross-linkers. In some embodiments, the plurality of beads is a plurality of gel beads. In some embodiments, the plurality of beads is dissolvable or disruptable.

In some embodiments, (b) comprises sequentially coupling multiple molecules to each of the plurality of molecules.

In some embodiments, in (b) the one or more molecules comprise a first molecule comprising a first segment and a second molecule comprising a second segment, and wherein the combinatorially assembling comprises coupling the first molecule to a molecule of the plurality of molecules and coupling the second molecule to the first molecule, wherein the molecule is coupled to the support. In some embodiments, the method further comprises coupling a third molecule comprising a third segment to the second molecule. In some embodiments, the third segment is different than the first segment or the second segment. In some embodiments, the third segment is different than the first segment and the second segment. In some embodiments, the first segment of the first molecule is different than the second segment of the second molecule.

In some embodiments, wherein the first molecule comprises a double-stranded region comprising the first segment and a single-stranded region. In some embodiments, the single-stranded region of the first molecule has six or fewer nucleotides. In some embodiments, the single-stranded region of the first molecule has two nucleotides. In some embodiments, the sequence of the single-stranded region of the first molecule is selected from the group consisting of CA, GT, AC, and TG. In some embodiments, the first molecule further comprises an additional single-stranded region configured to couple to the molecule of the plurality of molecules. In some embodiments, the single-stranded region and the additional single-stranded region of the first molecule are included in the same strand of the first molecule. In some embodiments, the second molecule comprises a double-stranded region comprising the second segment and a single-stranded region. In some embodiments, the single-stranded region of the second molecule comprises a sequence complementary to the sequence of the single-stranded region of the first molecule. In some embodiments, the single-stranded region of the second molecule has six or fewer nucleotides. In some embodiments, the single-stranded region of the second molecule has two nucleotides. In some embodiments, the second molecule further comprises an additional single-stranded region. In some embodiments, the single-stranded region and the additional single-stranded region of the second molecule are included in different strands of the second molecule.

In some embodiments, in (b) the one or more molecules comprise a third molecule comprising a third segment and a fourth molecule comprising a fourth segment, and wherein the combinatorially assembling comprises coupling the third molecule to an additional molecule of the plurality of molecules and coupling the fourth molecule to the third molecule, wherein the additional molecule is coupled to the support. In some embodiments, (i) the first molecule comprises a double-stranded region comprising the first segment and a single-stranded region and (ii) the third molecule comprises a double-stranded region comprising the third segment and a single-stranded region. In some embodiments, the first segment of the first molecule and the third segment are the same. In some embodiments, the second segment of the second molecule and the fourth segment of the fourth molecule are the same. In some embodiments, the single-stranded region of the first molecule and the single-stranded region of the third molecule are the same. In some embodiments, the single-stranded region of the first molecule and the single-stranded region of the third molecule are different. In some embodiments, the single-stranded region of the first molecule and the single-stranded region of the third molecule each have six or fewer nucleotides. In some embodiments, the molecule and the additional molecule coupled to the support are the same. In some embodiments, the molecule and the additional molecule coupled to the support are different. In some embodiments, the second molecule comprises a first functional sequence and the fourth molecule comprises a second functional sequence, which first functional sequence is different than the second functional sequence.

In some embodiments, the one or more molecules comprise a plurality of first molecules comprising the first segment, a plurality of second molecules comprising the second segment, a plurality of third molecules comprising the third segment, and a plurality of fourth molecules comprising the fourth segment, and wherein the combinatorially assembling comprises (i) coupling first molecules of the plurality of first molecules to molecules of the plurality of molecules and coupling second molecules of the plurality of second molecules to the first molecules, and (ii) coupling third molecules of the plurality of third molecules to additional molecules of the plurality of molecules and coupling fourth molecules of the plurality of fourth molecules to the third molecules, wherein the molecules and the additional molecules of the plurality of molecules are coupled to the support. In some embodiments, among the one or molecules, the plurality of first molecules comprises a greater number of molecules than the plurality of third molecules. In some embodiments, among the one or more molecules, the plurality of second molecules comprises a greater number of molecules than the plurality of fourth molecules. In some embodiments, the molecules of the plurality of molecules comprises a greater number of molecules than the additional molecules of the plurality of molecules.

In some embodiments, (b) comprises ligating the one or more molecules to each of the plurality of molecules coupled to the plurality of supports.

In some embodiments, (b) comprises partitioning the plurality of molecules coupled to the plurality of supports in separate partitions, and coupling at least a subset of the one or more molecules to molecules of the plurality of molecules in the separate partitions. In some embodiments, (b) further comprises partitioning the plurality of molecules coupled to the plurality of supports in one or more additional partitions, and coupling at least a subset of the one or more molecules to molecules of the plurality of molecules in the one or more additional partitions. In some embodiments, the separate partitions are wells. In some embodiments, the separate partitions are droplets.

In some embodiments, the barcode sequences are nucleic acid sequences. In some embodiments, the barcode sequences are amino acid sequences. In some embodiments, barcode molecules of the other supports of the plurality of supports comprise different barcode sequences. In some embodiments, each other support of the other supports of the plurality of supports comprises barcode molecules comprising a different barcode sequence.

In some embodiments, the one or more segments are at least one nucleotide in length.

In some embodiments, each of the barcode molecules of the first set of barcode molecules and the barcode molecules of the second set of barcode molecules comprises a unique identifier that is different than unique identifiers of other barcode molecules coupled to the support.

In some embodiments, the barcode molecules of the first set of barcode molecules and the barcode molecules of the second set of barcode molecules comprise at least 100,000 barcode molecules.

In some embodiments, each of the barcode molecules of the first set of barcode molecules and the barcode molecules of the second set of barcode molecules comprise a segment separated from the one or more segments by a sequence that is the same across at least a subset of the plurality of barcode molecules.

In some embodiments, the one or more segments are different for at least a subset of the plurality of barcode molecules.

In some embodiments, barcode molecules of the first set of barcode molecules include a first sequence for use with a first assay and barcode molecules of the second set of barcode molecules include a second sequence for use with a second assay, wherein the first assay is different than the second assay.

In some embodiments, barcode molecules of the first set of barcode molecules and barcode molecules of the second set of barcode molecules include both identical barcode sequences and different barcode sequences.

In some embodiments, barcode molecules of the first set of barcode molecules include first functional sequences and barcode molecules of the second set of barcode molecules include second functional sequences, wherein the first functional sequences and the second functional sequences are different. In some embodiments, the first set of barcode molecules coupled to the support comprises a greater number of barcode molecules than the second set of barcode molecules coupled to the support. In some embodiments, the first set of barcode molecules coupled to the support comprises at least 10,000 barcode molecules. In some embodiments, the second set of barcode molecules coupled to the support comprises at least 10,000 barcode molecules.

In some embodiments, the method further comprises contacting a solution comprising the first molecule and the second molecule coupled to the molecule of the plurality of molecules with an exonuclease. In some embodiments, the second molecule comprises a phosphorothioate moiety.

In another aspect, the present disclosure provides a method of processing a plurality of barcode molecules, comprising: (a) providing a plurality of molecules coupled to a plurality of supports; (b) subjecting a subset of molecules of the plurality of molecules to conditions sufficient to couple first molecules to the subset of molecules, wherein the subset of molecules are coupled to a support of the plurality of supports; (c) subjecting the first molecules coupled to the subset of molecules to conditions sufficient to couple second molecules to the first molecules, thereby generating the plurality of barcode molecules and by-products, which plurality of barcode molecules comprise the second molecules coupled to the first molecules; and (d) contacting the products and by-products with a molecule capable of degrading the by-products.

In some embodiments, the molecule capable of degrading the by-products is an exonuclease.

In some embodiments, the second molecules comprise phosphorothioate moieties. In some embodiments, the phosphorothioate moieties are disposed at an end of the second molecules.

In some embodiments, the plurality of barcode molecules comprises a plurality of barcode sequences. In some embodiments, the plurality of barcode sequences of the plurality of barcode molecules coupled to the support are identical. In some embodiments, the plurality of barcode sequences comprises a plurality of nucleic acid barcode sequences.

In some embodiments, the plurality of supports comprises a plurality of beads, and wherein the plurality of barcode molecules are coupled to a bead of the plurality of beads. In some embodiments, the plurality of beads is a plurality of gel beads. In some embodiments, the plurality of beads is dissolvable or disruptable. In some embodiments, the plurality of barcode molecules is releasably coupled to the bead.

In some embodiments, (b) comprises ligating the first molecules to the molecules.

In some embodiments, (c) comprises ligating the second molecules to the first molecules.

In some embodiments, the method further comprises partitioning the plurality of molecules coupled to the plurality of supports in separate partitions. In some embodiments, (b) comprises coupling the first molecules to the subset of molecules within a partition of the separate partitions. In some embodiments, the method further comprises, subsequent to (b), partitioning the plurality of molecules coupled to the plurality of supports in one or more additional partitions. In some embodiments, (c) comprises coupling the second molecules to the first molecules within a partition of the one or more additional partitions. In some embodiments, the separate partitions are wells. In some embodiments, the separate partitions are droplets. In some embodiments, prior to (d), the plurality of barcode molecules coupled to the support and the by-products are recovered from the separate partitions.

In some embodiments, the first molecules and the second molecules are nucleic acid molecules, which nucleic acid molecules each comprise at least two nucleotides.

In some embodiments, the plurality of barcode molecules coupled to the support comprises at least 10,000 barcode molecules.

In some embodiments, the plurality of barcode molecules coupled to the support comprises a plurality of first barcode molecules and a plurality of second barcode molecules, which plurality of first barcode molecules and plurality of second barcode molecules are different. In some embodiments, the plurality of first barcode molecules comprise a plurality of first barcode sequences and the plurality of second barcode molecules comprise a plurality of second barcode sequences, which first barcode sequences are different than the second barcode sequences. In some embodiments, the plurality of first barcode molecules comprise first functional sequences and the plurality of second barcode molecules comprise second functional sequences, which first functional sequences are different than the second functional sequences.

In some embodiments, the plurality of barcode molecules comprise a plurality of functional sequences. In some embodiments, the functional sequences are poly(T) sequences.

In a further aspect, the present disclosure provides a composition comprising a support comprising a plurality of nucleic acid barcode molecules coupled thereto, which plurality of nucleic acid barcode molecules comprise one or more sequences selected from the sequences included in Table 1 or Table 2.

In some embodiments, the plurality of nucleic acid barcode molecules comprise one or more sequences from the sequences included in Table 1.

In some embodiments, the plurality of nucleic acid barcode molecules comprise one or more sequences from the sequences included in Table 2. In some embodiments, the plurality of nucleic acid barcode molecules comprise the sequence CCTTAGCCGCTAATAGGTGAGC (SEQ ID NO: 155). In some embodiments, the plurality of nucleic acid barcode molecules comprise the sequence TTGCTAGGACCGGCCTTAAAGC (SEQ ID NO: 156).

In some embodiments, each nucleic acid barcode molecule of the plurality of nucleic acid barcode molecules comprises one or more sequences selected from the sequences included in Table 1 or Table 2.

In some embodiments, the plurality of nucleic acid barcode molecules comprise a first plurality of nucleic acid barcode molecules and a second plurality of nucleic acid barcode molecules, which first plurality of nucleic acid barcode molecules comprise one or more sequences selected from the sequences included in Table 1 or Table 2 and which second plurality of nucleic acid barcode molecules do not comprise a sequence included in Table 1 or Table 2. In some embodiments, the second plurality of nucleic acid barcode molecules are configured to interact with ribonucleic acid molecules. In some embodiments, the second plurality of nucleic acid barcode molecules comprise a poly(T) sequence. In some embodiments, the first plurality of nucleic acid barcode molecules are configured to interact with deoxyribonucleic acid molecules.

In some embodiments, the first plurality of nucleic acid barcode molecules comprises at least 10,000 nucleic acid barcode molecules. In some embodiments, the second plurality of nucleic acid barcode molecules comprises at least 10,000 nucleic acid barcode molecules. In some embodiments, among the plurality of nucleic acid barcode molecules, the first plurality of nucleic acid barcode molecules comprises a greater number of nucleic acid barcode molecules than the second plurality of nucleic acid barcode molecules. In some embodiments, among the plurality of nucleic acid barcode molecules, the second plurality of nucleic acid barcode molecules comprises a greater number of nucleic acid barcode molecules than the first plurality of nucleic acid barcode molecules.

In some embodiments, the support is a bead. In some embodiments, the bead is a gel bead. In some embodiments, the bead is dissolvable or disruptable. In some embodiments, the plurality of nucleic acid barcode molecules is releasably coupled to the bead.

In some embodiments, the plurality of nucleic acid barcode molecules coupled to the support comprise a plurality of barcode sequences. In some embodiments, the plurality of barcode sequences is the same for each of the plurality of nucleic acid barcode molecules. In some embodiments, the plurality of barcode sequences is a plurality of nucleic acid barcode sequences.

In some embodiments, the plurality of nucleic acid barcode molecules comprises at least 10,000 nucleic acid barcode molecules.

In another aspect, the present disclosure provides a kit comprising a plurality of barcode molecules, comprising: a plurality of supports; and a plurality of barcode molecules coupled to the plurality of supports, wherein the plurality of barcode molecules comprises (i) a first set of barcode molecules coupled to a support of the plurality of supports and (ii) a second set of barcode molecules coupled to the support, wherein first barcode molecules of the first set of barcode molecules are different than second barcode molecules of the second set of barcode molecules, and wherein the first barcode molecules are configured to interact with different target molecules than the second barcode molecules.

In some embodiments, the first barcode molecules of the first set of barcode molecules and the second barcode molecules of the second set of barcode molecules comprise barcode sequences that are different from barcode sequences of barcode molecules coupled to other supports of the plurality of supports.

In some embodiments, the first barcode molecules of the first set of barcode molecules and the second barcode molecules of the second set of barcode molecules comprise barcode sequences, wherein the barcode sequences of the first barcode molecules of the first set of barcode molecules and the second barcode molecules of the second set of barcode molecules are identical.

In some embodiments, the plurality of supports is a plurality of beads, and wherein the first barcode molecules of the first set of barcode molecules and the second barcode molecules of the second set of barcode molecules are coupled to a bead of the plurality of beads. In some embodiments, at least a subset of the first barcode molecules of the first set of barcode molecules and/or the second barcode molecules of the second set of barcode molecules is coupled to an interior of the bead. In some embodiments, the first barcode molecules of the first set of barcode molecules and the second barcode molecules of the second set of barcode molecules are releasably coupled to the bead. In some embodiments, the first barcode molecules of the first set of barcode molecules and the second barcode molecules of the second set of barcode molecules are releasably coupled to the bead through chemical cross-linkers. In some embodiments, the plurality of beads is a plurality of gel beads. In some embodiments, the plurality of beads is dissolvable or disruptable.

In some embodiments, the first barcode molecules or the second barcode molecules are configured to interact with deoxyribonucleic acid molecules. In some embodiments, the first barcode molecules or the second barcode molecules are configured to interact with ribonucleic acid molecules. In some embodiments, the first barcode molecules or the second barcode molecules are configured to interact with amino acids, polypeptides or proteins.

In some embodiments, the first barcode molecules of the first set of barcode molecules and the second barcode molecules of the second set of barcode molecules comprise barcode sequences, which barcode sequences are nucleic acid sequences. In some embodiments, the first barcode molecules of the first set of barcode molecules and the second barcode molecules of the second set of barcode molecules comprise barcode sequences, which barcode sequences are amino acid sequences.

In some embodiments, each of the first barcode molecules of the first set of barcode molecules and the second barcode molecules of the second set of barcode molecules comprises a unique identifier that is different than unique identifiers of other barcode molecules coupled to the support.

In some embodiments, the first barcode molecules of the first set of barcode molecules and the second barcode molecules of the second set of barcode molecules comprise at least 100,000 barcode molecules.

In some embodiments, the first barcode molecules of the first set of barcode molecules and the second barcode molecules of the second set of barcode molecules include both identical barcode sequences and different barcode sequences.

In some embodiments, the first barcode molecules of the first set of barcode molecules include a first sequence for use with a first assay and the second barcode molecules of the second set of barcode molecules include a second sequence for use with a second assay, wherein the first assay is different than the second assay. In some embodiments, the first sequences of the first barcode molecules of the first set of barcode molecules are configured to interact with first target molecules and the second sequences of the second barcode molecules of the second set of barcode molecules are configured to interact with second target molecules. In some embodiments, the first target molecules are deoxyribonucleic acid molecules and the second target molecules are ribonucleic acid molecules.

In some embodiments, the first set of barcode molecules coupled to the support comprises a greater number of barcode molecules than the second set of barcode molecules coupled to the support.

In a further aspect, the present disclosure provides a method for processing a plurality of analytes, comprising: (a) providing a plurality of barcode molecules coupled to a plurality of supports, wherein the plurality of barcode molecules comprises (i) a first set of barcode molecules coupled to a support of the plurality of supports and (ii) a second set of barcode molecules coupled to the support, wherein first barcode molecules of the first set of barcode molecules are different than second barcode molecules of the second set of barcode molecules; (b) partitioning the support of the plurality of supports in a partition, wherein subsequent to partitioning, the partition comprises the plurality of analytes; (c) using (i) a first barcode molecule from the first set of barcode molecules and a first analyte from the plurality of analytes to generate a first barcoded analyte, and (ii) a second barcode molecule from the second set of barcode molecules and a second analyte from the plurality of analytes to generate a second barcoded analyte; and (d) recovering (i) the first barcoded analyte or a derivative thereof and (ii) the second barcoded analyte or a derivative thereof from the partition.

In some embodiments, the first barcode molecules of the first set of barcode molecules and the second barcode molecules of the second set of barcode molecules comprise barcode sequences that are different from barcode sequences of barcode molecules coupled to other supports of the plurality of supports.

In some embodiments, the first barcode molecules of the first set of barcode molecules and the second barcode molecules of the second set of barcode molecules comprise barcode sequences, wherein the barcode sequences of the first barcode molecules of the first set of barcode molecules and the second barcode molecules of the second set of barcode molecules are identical. In some embodiments, the plurality of supports is a plurality of beads, and wherein the first barcode molecules of the first set of barcode molecules and the second barcode molecules of the second set of barcode molecules are coupled to a bead of the plurality of beads. In some embodiments, at least a subset of the first barcode molecules of the first set of barcode molecules and/or the second barcode molecules of the second set of barcode molecules is coupled to an interior of the bead. In some embodiments, the first barcode molecules of the first set of barcode molecules and the second barcode molecules of the second set of barcode molecules are releasably coupled to the bead. In some embodiments, the first barcode molecules of the first set of barcode molecules and the second barcode molecules of the second set of barcode molecules are releasably coupled to the bead through chemical cross-linkers. In some embodiments, the plurality of beads is a plurality of gel beads. In some embodiments, the plurality of beads is dissolvable or disruptable.

In some embodiments, the plurality of analytes comprises a plurality of deoxyribonucleic acid molecules. In some embodiments, the plurality of analytes comprises a plurality of ribonucleic acid molecules. In some embodiments, the plurality of analytes comprises a plurality of amino acids, polypeptides or proteins.

In some embodiments, the first analyte is a deoxyribonucleic acid molecule. In some embodiments, the second analyte is a ribonucleic acid molecule.

In some embodiments, the first barcode molecules of the first set of barcode molecules and the second barcode molecules of the second set of barcode molecules comprise barcode sequences, which barcode sequences are nucleic acid sequences. In some embodiments, the first barcode molecules of the first set of barcode molecules and the second barcode molecules of the second set of barcode molecules comprise barcode sequences, which barcode sequences are amino acid sequences.

In some embodiments, each of the first barcode molecules of the first set of barcode molecules and the second barcode molecules of the second set of barcode molecules comprises a unique identifier that is different than unique identifiers of other barcode molecules coupled to the support.

In some embodiments, the first barcode molecules of the first set of barcode molecules and the second barcode molecules of the second set of barcode molecules comprise at least 100,000 barcode molecules.

In some embodiments, the first barcode molecules of the first set of barcode molecules and the second barcode molecules of the second set of barcode molecules include both identical barcode sequences and different barcode sequences.

In some embodiments, the first barcode molecules of the first set of barcode molecules include first functional sequences and the second barcode molecules of the second set of barcode molecules include second functional sequences, wherein the first functional sequences and the second functional sequences are different. In some embodiments, the first functional sequences of the first barcode molecules of the first set of barcode molecules are configured to interact with first analytes of the plurality of analytes and the second functional sequences of the second barcode molecules of the second set of barcode molecules are configured to interact with second analytes of the plurality of analytes. In some embodiments, the first analytes are deoxyribonucleic acid molecules and the second analytes are ribonucleic acid molecules.

In some embodiments, the first set of barcode molecules coupled to the support comprises a greater number of barcode molecules than the second set of barcode molecules coupled to the support.

In some embodiments, barcode molecules of the other supports of the plurality of supports comprise different barcode sequences.

In some embodiments, the partition is a well. In some embodiments, the partition is a droplet.

In some embodiments, (c) comprises performing one or more nucleic acid extension reactions.

In some embodiments, (i) the first barcode molecule or a sequence thereof and (ii) the second barcode molecule or a sequence thereof are released from the support.

In some embodiments, the plurality of analytes is components of a cell. In some embodiments, subsequent to (b), the cell is lysed or permeabilized to provide access to the plurality of analytes.

In some embodiments, subsequent to (c), the first barcoded analyte and the second barcoded analyte are in solution in the partition.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 12 shows examples of differential functionalization of a bead comprising different starter sequences (SEQ ID NOs: 165-168, respectively, in order of appearance).

FIG. 14 illustrates a double ligation reaction to provide a nucleic acid barcode molecule. FIG. 14 discloses SEQ ID NOs: 169-173, respectively, in order of appearance.

FIG. 15 discloses SEQ ID NOs: 169, 169, 170, 171, 170, 171, 172-174, and 173, respectively, in order of appearance.

FIG. 16 discloses SEQ ID NOs: 169, 186, 170, 171, 175, 176, 172, 173, 208, and 177, respectively, in order of appearance.

FIG. 17 shows a nucleic acid barcode molecule generated by a triple ligation method. FIG. 17 discloses SEQ ID NOs: 178-179, respectively, in order of appearance.

FIG. 18 shows a nucleic acid barcode molecule generated by a triple ligation method. FIG. 18 discloses SEQ ID NOs: 180-181, respectively, in order of appearance.

FIG. 19 discloses SEQ ID NOs: 182-185, respectively, in order of appearance.

FIG. 20 discloses SEQ ID NOs: 169, 186, 170, 171, 175, 176, 175, 176, 187-190, 189, 190, 172, 173, 167, 190, 191, and 190, respectively, in order of appearance.

FIG. 23 discloses SEQ ID NOs: 192, 193, 192, 193, 192, 193, 192, and 193, respectively, in order of appearance.

FIG. 27 discloses SEQ ID NOs: 194-195, respectively, in order of appearance.

FIG. 28 discloses SEQ ID NOs: 194-195, respectively, in order of appearance.

FIG. 31 shows a scheme relating to off-products in a ligation process. FIG. 31 discloses SEQ ID NOs: 196-199, respectively, in order of appearance.

FIG. 32 discloses SEQ ID NOs: 200-201, respectively, in order of appearance.

FIG. 33A discloses SEQ ID NOs: 169, 202, 171, 170, 171, 203, 204, 207, 205, 206, and 205, respectively, in order of appearance.

DETAILED DESCRIPTION

Figure 1:
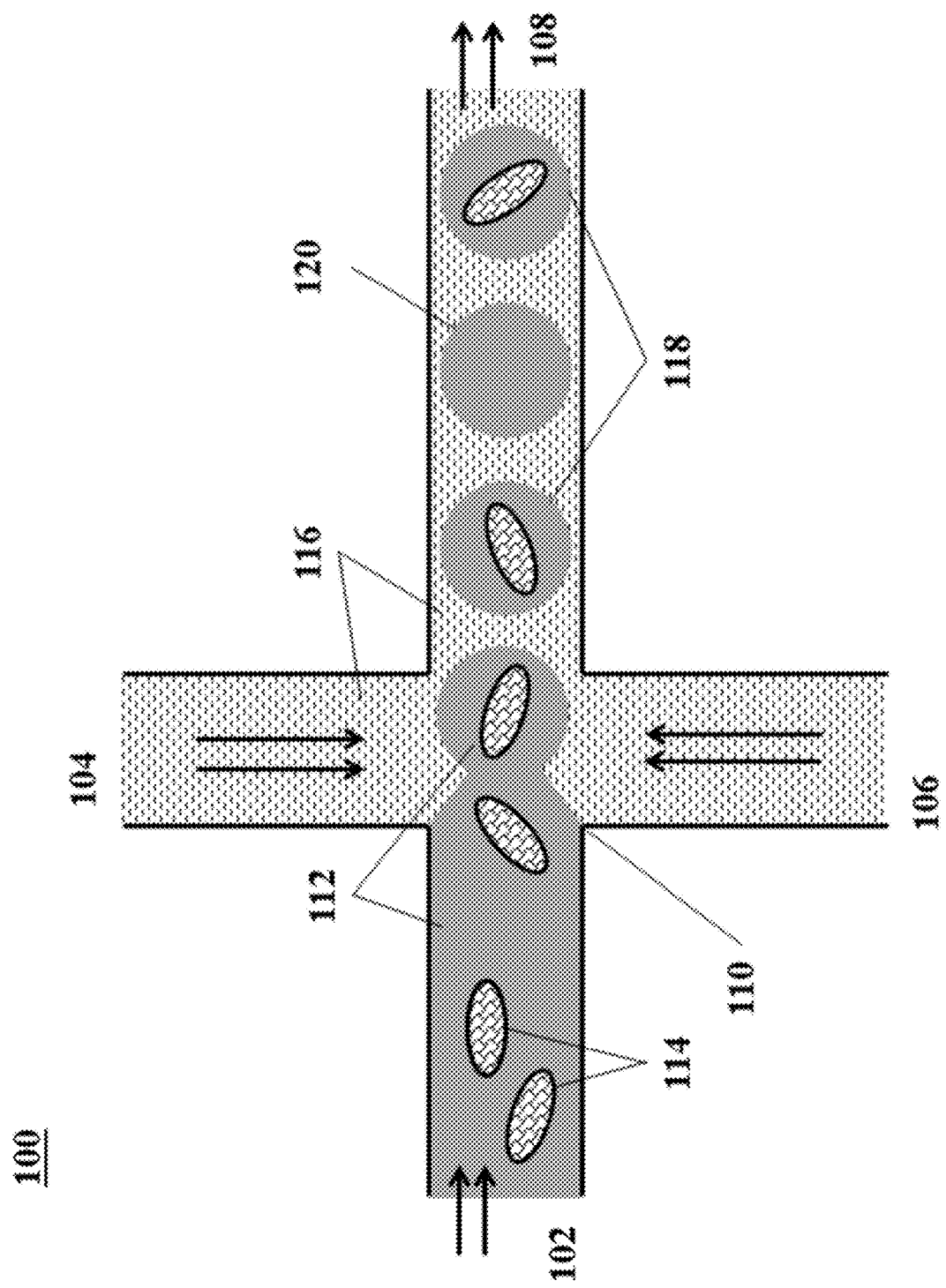
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or crosslinking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Provided herein are methods that may be used for various sample processing and/or analysis applications. A method of the present disclosure may provide a support (e.g., a bead, such as a gel bead) attached thereto two or more different barcode molecules (e.g., nucleic acid barcode molecules) each comprising one or more sequences (e.g., priming sequences, barcode sequences, random N-mer sequences, capture sequences, poly(T) sequences, and/or other sequences). Two or more different barcode molecules attached to a support may comprise the same or different features. For example, a first barcode molecule attached to a support may comprise a first feature (e.g., a first sequence, such as a first nucleic acid sequence) and a second barcode molecule attached to the same support may comprise a second feature (e.g., a second sequence, such as a second nucleic acid sequence) that is the same as or different from said first feature. In some cases, a first barcode molecule attached to a support may comprise a first feature and a second feature and a second barcode molecule attached to the same support may comprise a third feature and a fourth feature, where the first and third features may be different from the second and fourth features. For example, different nucleic acid barcode molecules attached to the same bead may comprise the same barcode sequence and one or more different other sequences (e.g., functional or starter sequences). A barcode molecule may be releasably attached to a support (e.g., a bead). Methods of generating a plurality of barcode molecules coupled to a plurality of supports may comprise combinatorial (e.g., split pool) assembly and a series of hybridization and ligation processes. The methods may facilitate combinatorial construction of a bead library comprising beads comprising a plurality of different barcode molecules.

Methods of Generating Barcode Molecules

In an aspect, the present disclosure provides a method for generating a plurality of barcode molecules (e.g., nucleic acid barcode molecules) from a plurality of molecules (e.g., nucleic acid molecules, such as a nucleic acid molecule comprising a starter or functional flow cell sequence) coupled to a plurality of supports (e.g., beads). The method may comprise combinatorially assembling (e.g., using a split pool method) the plurality of barcode molecules by coupling one or more molecules to each of the plurality of molecules. Each of the molecules coupled to a molecule coupled to a support may comprise one or more features, such as one or more nucleic acid sequences (e.g., barcode sequences, functional sequences, starter sequences, and/or overhang sequences, or complements thereof). A feature may comprise a barcode sequence or a portion of a barcode sequence. The plurality of molecules generated through this method may comprise (i) a first set of barcode molecules coupled to a support of a plurality of supports and (ii) a second set of barcode molecules coupled to the same support, where barcode molecules of the first set of barcode molecules are different than barcode molecules of the second set of barcode molecules. Barcode molecules of the first set of barcode molecules and barcode molecules of the second set of barcode molecules may comprise the same barcode sequence. The barcode molecules of the first set of barcode molecules and the barcode molecules of the second set of barcode molecules may comprise a barcode sequence that is different from other barcode sequences of other barcode molecules coupled to other supports of the plurality of supports. Accordingly, the method may provide a combinatorially constructed library of beads where each bead comprises two or more different barcode molecules, where each barcode molecule attached to a given bead comprises the same barcode sequence.

In some cases, methods of the present disclosure may be used to generate barcode molecules comprising one or more amino acids, peptides, proteins, PEG moieties, hydrocarbon chains, and/or other moieties. In some cases, methods of the present disclosure may be used to generate nucleic acid barcode molecules. In some cases, methods of the present disclosure may be used to generate barcode molecules that may be useful in a plurality of assays. A support may have multiple barcode molecule populations coupled thereto, each population of which may be configured for use in a different assay. For example, a first population of barcode molecules coupled to the support may comprise a first sequence (e.g., a poly(T) sequence) for use with a first assay (e.g., analysis of a messenger ribonucleic acid molecule) and a second population of barcode molecules coupled to the same support may comprise a second sequence (e.g., a capture sequence) for use with a second assay (e.g., analysis of a deoxyribonucleic acid molecule) that is different from the first assay.

The methods described herein may comprise multiple ligation and/or hybridization processes. For example, a method may comprise providing a bead (e.g., a gel bead) that may have a starter sequence coupled thereto; providing a first molecule comprising a first sequence; attaching the first sequence of the first molecule to the starter sequence, thereby generating a first product; providing a second molecule comprising a second sequence; and attaching the second sequence of the second molecule to the first product, thereby generating a second product. The second product may comprise a barcode molecule, and may comprise one or more barcode sequences, functional sequences, and/or other sequences. In some cases, the method may further comprise providing a third molecule comprising a third sequence and attaching the third sequence of the third molecule to the second product, thereby generating a third product. In such a case, the third product may comprise a barcode molecule, and may comprise one or more barcode sequences, functional sequences, and/or other sequences. The starter sequence may comprise a functional sequence such as a flow cell functional sequence and/or a partial read sequence. The first, second, and third molecules may comprise first, second, and third barcode sequences, respectively. One or more of the first, second, and third molecules may comprise a functional sequence such as a poly(T) sequence or a DNA capture sequence. One or more of the first, second, and third molecules may also comprise an overhang sequence to facilitate attachment of a particular sequence at a specific location. The barcode molecules generated using the methods described herein may be releasably attached to a support. In some cases, a combinatorial (e.g., split pool) approach may be employed to provide a plurality of supports each comprising attached thereto two or more different barcode molecules.

A support used in a method of the present disclosure may be, for example, a well, matrix, rod, container, or bead(s). A support may have any useful features and characteristics, such as any useful size, fluidity, solidity, density, porosity, and composition. In some cases, a support may be a bead such as a gel bead. A bead may be solid or semi-solid. Additional details of beads are provided elsewhere herein.

A support (e.g., a bead) may comprise a starter sequence functionalized thereto (e.g., as described herein). A starter sequence may be attached to the support via, for example, a disulfide linkage. A starter sequence may comprise a partial read sequence and/or flow cell functional sequence. Such a sequence may permit sequencing of nucleic acid molecules attached to the sequence by a sequencer (e.g., an Illumina sequencer). Different starter sequences may be useful for different sequencing applications. A starter sequence may comprise, for example, a TruSeq or Nextera sequence. A starter sequence may have any useful characteristics such as any useful length and nucleotide composition. For example, a starter sequence may comprise 2, 3, 4, 5, 6, 7, 8, 9, 10, 11, 12, 13, 14, 15, 16, 17, 18, 19, 20, or more nucleotides. In some cases, a starter sequence may comprise 15 nucleotides. Nucleotides of a starter sequence may be naturally occurring or non-naturally occurring (e.g., as described herein). A bead may comprise a plurality of starter sequences attached thereto. For example, a bead may comprise a plurality of first starter sequences attached thereto. In some cases, a bead may comprise two or more different starter sequences attached thereto. For example, a bead may comprise both a plurality of first starter sequences (e.g., Nextera sequences) and a plurality of second starter sequences (e.g., TruSeq sequences) attached thereto. For a bead comprising two or more different starter sequences attached thereto, the sequence of each different starter sequence may be distinguishable from the sequence of each other starter sequence at an end distal to the bead. For example, the different starter sequences may comprise one or more nucleotide differences in the 2, 3, 4, 5, 6, 7, 8, 9, 10, or more nucleotides furthest from the bead.

A first molecule (e.g., a first nucleic acid molecule) may be provided that is capable of attaching to a starter sequence attached to a bead. A first molecule may be, for example, a nucleic acid molecule and/or may comprise an amino acid, peptide, polyethylene glycol (PEG) moiety, hydrocarbon chain, or another moiety. A first nucleic acid molecule may comprise a double-stranded region and one or more single-stranded regions. For example, a first nucleic acid molecule may comprise a central portion that is a double-stranded region and adjacent regions on either side that are single-stranded regions. Such a nucleic acid molecule may be referred to as a "splint oligonucleotide." Both single-stranded regions of the first nucleic acid molecule may be on the same strand. The single-stranded region on a first end of a first nucleic acid molecule may comprise 1, 2, 3, 4, 5, 6, or more nucleotides. This single-stranded region may be referred to as an "overhang" sequence. The single-stranded region on a second end of a first nucleic acid molecule may comprise a sequence that is complementary to a starter sequence attached to the bead. For example, the bead may comprise a starter sequence comprising a TruSeq sequence, and a first nucleic acid molecule may comprise a single-stranded region comprising a sequence that is complementary to a distal portion of the TruSeq sequence. The complementary sequence may comprise any useful length and base composition. Similarly, the double-stranded region may comprise any useful length and composition. A strand of the double-stranded region of the first nucleic acid molecule may comprise a barcode sequence, and the corresponding strand may comprise a complement of the barcode sequence. As an example, the first nucleic acid molecule may comprise a first strand including a first barcode sequence and a second strand including a sequence complementary to a starter sequence or a portion thereof that is attached to a bead, a sequence complementary to the first barcode sequence of the first strand, and an overhang sequence.

Figure 13:
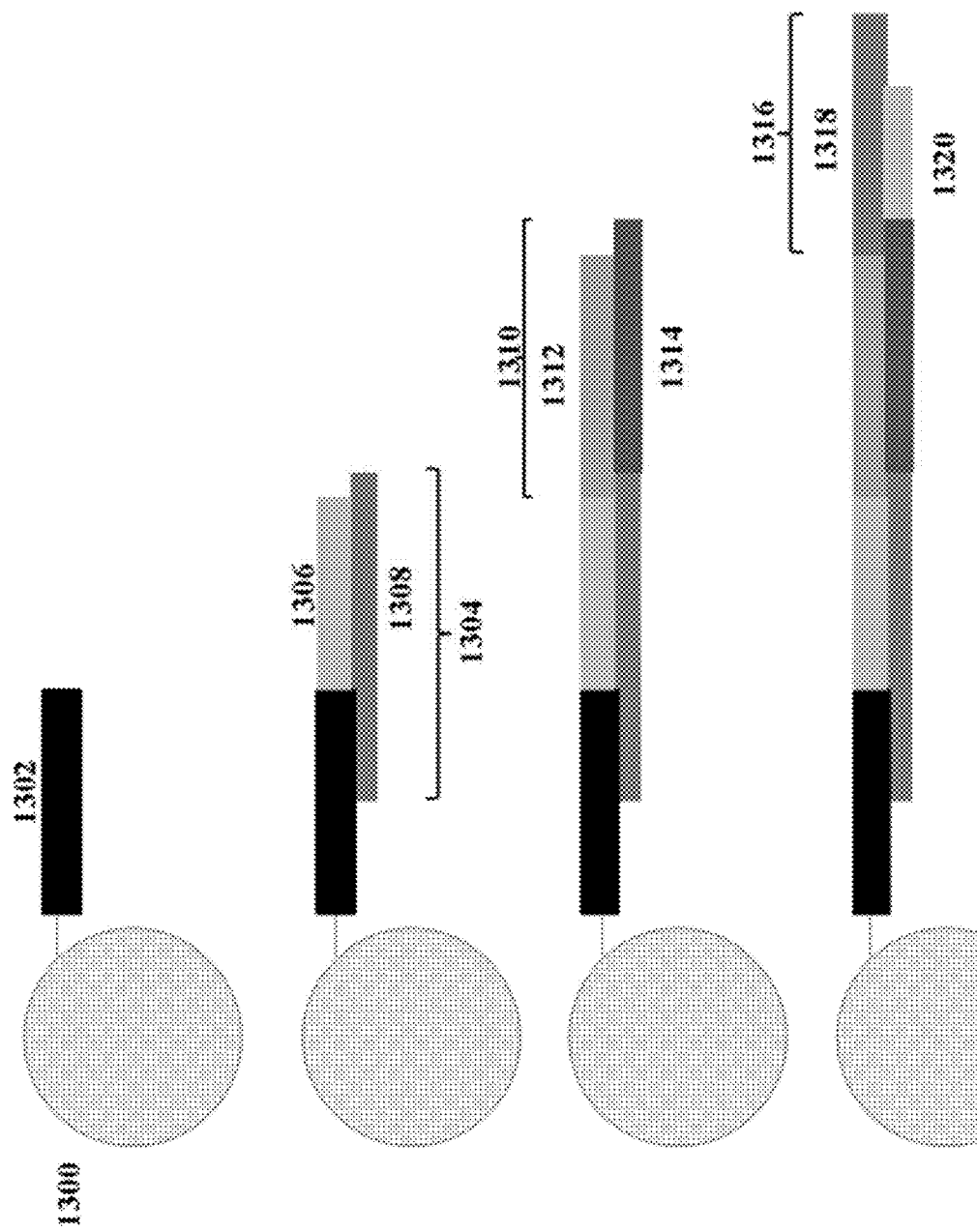
FIG. 13 schematically illustrates a triple ligation reaction.

A first molecule (e.g., a first nucleic acid molecule or segment) may be attached to the starter sequence attached to the support (e.g., bead, such as a gel bead). Attachment of the first molecule may comprise hybridization and/or ligation (e.g., as described herein). FIG. 13 shows an example of this process. Bead 1300 comprises starter sequence 1302 attached thereto. As described herein, starter sequence 1302 may comprise a partial read sequence such as a TruSeq or Nextera sequence. In the second panel, first molecule 1304 is ligated to starter sequence 1302. First molecule 1304 comprises a first strand 1306 that comprises a first barcode sequence and a second strand 1308 that comprises a sequence complementary to starter sequence 1302, a sequence complementary to the first barcode sequence of first strand 1306, and an overhang sequence. Ligation of first molecule 1304 to starter sequence 1302 may comprise hybridization of the sequence of second strand 1308 that is complementary to starter sequence 1302 to starter sequence 1302.

A second molecule (e.g., a second nucleic acid molecule or segment) may be provided that is capable of attaching to the overhang sequence of a first molecule attached to a starter sequence attached to a support (e.g., bead). A second molecule may be, for example, a nucleic acid molecule and/or may comprise an amino acid, peptide, PEG moiety, hydrocarbon chain, or another moiety. A second nucleic acid molecule may comprise a double-stranded region and one or more single-stranded regions. For example, a second nucleic acid molecule may comprise a central portion that is a double-stranded region and adjacent regions on either side that are single-stranded regions. The single-stranded regions of the second nucleic acid molecule may be on the same or different strands. In some cases, a first strand of a second nucleic acid molecule comprises a single-stranded region comprising 1, 2, 3, 4, 5, 6, or more nucleotides. This single-stranded region may be referred to as a "complementary overhang" sequence. This sequence may be complementary to the overhang sequence of a first nucleic acid molecule. The first strand may comprise a second single-stranded region at a second end that comprises one or more additional sequences such as a unique molecular identifier or a functional sequence. The single-stranded region of a second end of the first strand of the second nucleic acid molecule may comprise 1, 2, 3, 4, 5, 6, 7, 8, 9, 10, 12, 14, 16, 18, 20, 25, 30, 35, 40, 45, 50, or more nucleotides. The first strand may further comprise a second barcode sequence in the double stranded region of the second nucleic acid molecule. The second strand may comprise a sequence complementary to the second barcode sequence. Accordingly, in some cases, a second nucleic acid molecule comprises a first strand comprising a complementary overhang sequence, a second barcode sequence, and one or more additional sequences such as a unique molecular identifier or a functional sequence and a second strand comprising a sequence that is complementary to the second barcode sequence. In other cases, the first strand may include a single-stranded region and the second strand may include a single-stranded region. The single-stranded region of a first strand of a second nucleic acid molecule may comprise a "complementary overhang" sequence that is complementary to the overhang sequence of a first nucleic acid molecule. The single-stranded region of the second strand of the second nucleic acid molecule may comprise 1, 2, 3, 4, 5, 6, or more nucleotides. This single-stranded region may be referred to as a "second overhang" sequence. The double-stranded region may comprise any useful length and composition. A strand of the double-stranded region of the second nucleic acid molecule may comprise a second barcode sequence, and the corresponding strand may comprise a complement of the second barcode sequence. As an example, the second nucleic acid molecule may comprise a first strand including a second barcode sequence and a complementary overhang sequence and a second strand including a sequence complementary to the second barcode sequence of the first strand, and a second overhang sequence. A second nucleic acid molecule may be ligated to the first nucleic acid molecule (e.g., as described herein). In FIG. 13, second molecule 1310 comprises first strand 1312 comprising a complementary overhang sequence and a second barcode sequence and second strand 1314 comprising a sequence complementary to the second barcode sequence and a second overhang sequence. Ligation of second molecule 1310 to first molecule 1304 may comprise hybridization of the sequence of first strand 1312 that is complementary to the overhang sequence of strand 1308 of first molecule 1304 to strand 1308.

In some cases, a third molecule (e.g., a third nucleic acid molecule or segment) may be provided that is capable of attaching to the overhang sequence of a second molecule attached to a first molecule attached to a starter sequence attached to a support (e.g., bead). A third molecule may be, for example, a nucleic acid molecule and/or may comprise an amino acid, peptide, PEG moiety, hydrocarbon chain, or another moiety. A third nucleic acid molecule may comprise a double-stranded region and one or more single-stranded regions. For example, a third nucleic acid molecule may comprise a central portion that is a double-stranded region and adjacent regions on either side that are single-stranded regions. The single-stranded regions of the second nucleic acid molecule may be the same strand. The single-stranded region of a first end of a first strand of a third nucleic acid molecule may comprise 1, 2, 3, 4, 5, 6, or more nucleotides. This single-stranded region may be referred to as a "second complementary overhang" sequence. This sequence may be complementary to the second overhang sequence of a second nucleic acid molecule. The single-stranded region of a second end of the first strand of the third nucleic acid molecule may comprise 1, 2, 3, 4, 5, 6, 7, 8, 9, 10, 12, 14, 16, 18, 20, 25, 30, 35, 40, 45, 50, or more nucleotides. This single-stranded region may comprise one or more sequences. For example, this region may comprise a unique molecular identifier, a third barcode sequence, and/or a functional sequence. The double-stranded region may comprise any useful length and composition. A strand of the double-stranded region of the second nucleic acid molecule may comprise a third barcode sequence, a unique molecular identifier, or another sequence and the corresponding strand may comprise a complement of the third barcode sequence, unique molecular identifier, or other sequence. As an example, the third nucleic acid molecule may comprise a first strand including a third barcode sequence, a second complementary overhang sequence that is complementary to the second overhang sequence of a second nucleic acid molecule, and one or more additional sequences such as a unique molecular identifier and a functional sequence. The second strand of the third nucleic acid molecule may include a sequence complementary to the third barcode sequence of the first strand. A third nucleic acid molecule may be ligated to the second nucleic acid molecule (e.g., as described herein). In FIG. 13, third molecule 1316 comprises first strand 1318 comprising a second complementary overhang sequence, a third barcode sequence, and one or more additional sequences and second strand 1320 comprising a sequence complementary to the third barcode sequence. Ligation of third molecule 1316 to second molecule 1310 may comprise hybridization of the sequence of first strand 1318 that is complementary to the overhang sequence of strand 1314 of second molecule 1310 to strand 1314.

Figure 14:
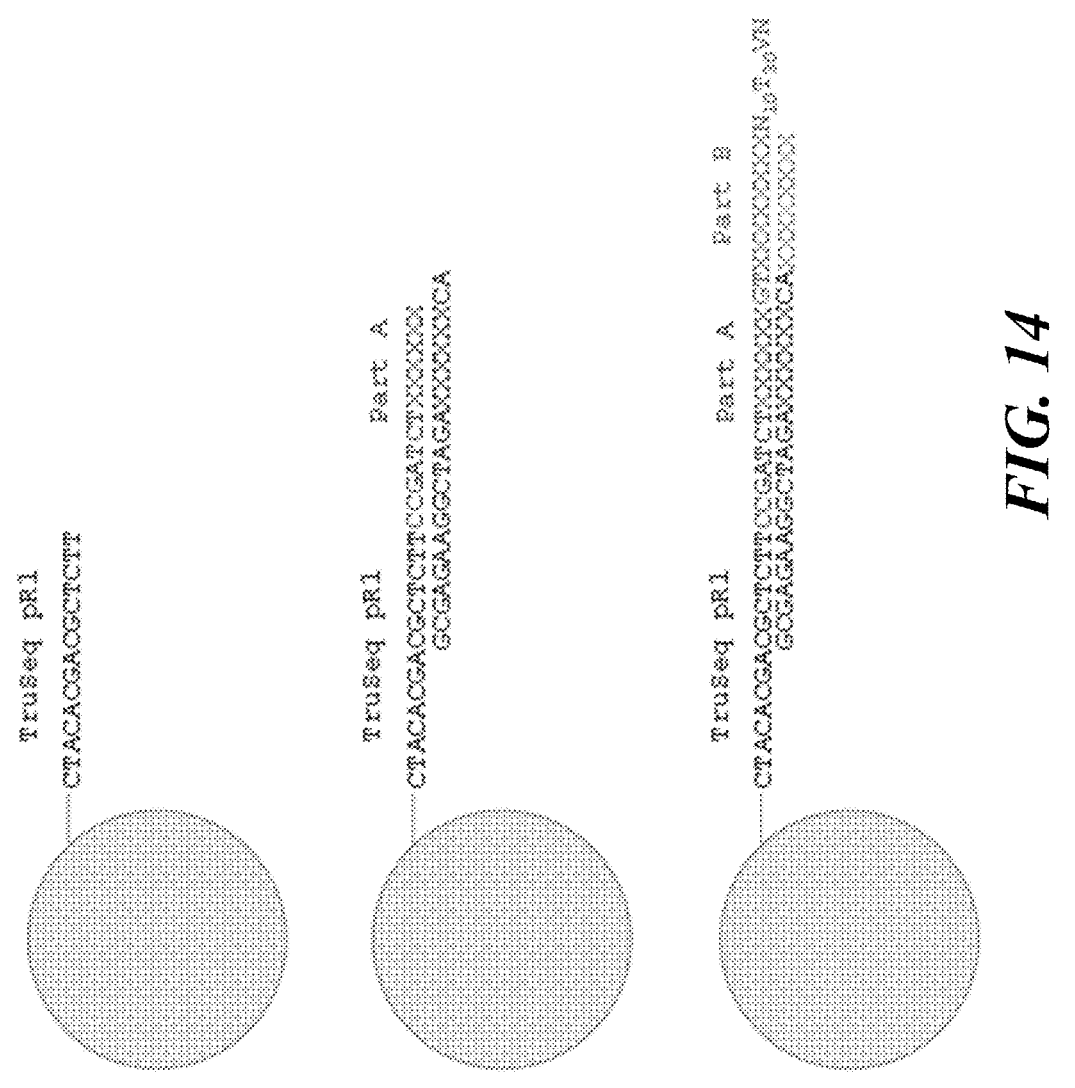

FIG. 14 shows an example of a double ligation method involving a bead comprising a starter sequence comprising a TruSeq sequence. In the second panel, a first nucleic acid molecule comprising a first strand (top) and a second strand (bottom) is ligated to the TruSeq sequence. The second strand of the first nucleic acid molecule comprises a sequence complementary to a portion of the TruSeq sequence at one end and a two-nucleotide overhang sequence (CA) at a second end. The first strand comprises a first barcode sequence (indicated by the sequence XXXXXX, where X represents a variable nucleotide), and the second strand comprises a sequence complementary to the first barcode sequence. In the third panel of FIG. 14, a second nucleic acid molecule comprising a first strand (top) and a second strand (bottom) is ligated to the first nucleic acid molecule. The first strand comprises a barcode sequence (indicated by the sequence XXXXXXXX, where X represents a variable nucleotide), and the second strand comprises a sequence complementary to the second barcode sequence. The first strand also comprises a two-nucleotide sequence (GT) that is complementary to the overhang sequence of the first nucleic acid molecule as well as additional sequences indicated by $N_{10}$ and $T_{30}VN$ (SEQ ID NO: 164). The sequence $N_{10}$ represents a random N-mer that represents a unique molecular identifier while the sequence $T_{30}VN$ (SEQ ID NO: 164) represents a functional sequence. The functional sequence included in FIG. 14 is a poly(T) sequence. Following ligation of the second nucleic acid molecule to the first nucleic acid molecule, the bead comprises a double-stranded nucleic acid barcode molecule attached thereto. The double-stranded nucleic acid barcode molecule may be denatured to remove the bottom strand and retain a single-stranded nucleic acid barcode molecule attached to the bead. This single-stranded nucleic acid barcode molecule may also be referred to as a "nucleic acid barcode molecule".

Successive attachment of a first molecule, second molecule, and, in some cases, a third molecule to a bead or a sequence attached thereto may result in the generation of a bead comprising a barcode molecule (e.g., a nucleic acid barcode molecule). The barcode molecule may be useful in various analysis and processing applications. Barcode molecules attached to beads may be useful for capturing and/or labeling, for example, nucleic acid sequences. A barcode molecule (e.g., a nucleic acid barcode molecule) may comprise a functional sequence designed to interact with a particular nucleic acid sequence or type of sequence. For example, a nucleic acid barcode molecule may comprise a functional sequence selected from the group consisting of capture sequences (e.g., random N-mers), poly(T) sequences, poly(C) sequences, primer sequences, universal primer sequences, primer annealing sequences, or other sequences. The nucleic acid barcode molecule may comprise one or more barcode sequences and/or unique molecular identifiers and be useful for indexing nucleic acid sequences deriving from one or a variety of sources. If a plurality of beads each comprising one or more barcode molecules comprising a unique barcode and/or unique molecular identifier is partitioned amongst a plurality of partitions (e.g., droplets or wells, as described herein) each comprising an analyte, the barcode molecules may be useful for indexing the analytes corresponding to each partition.

Multiple barcode molecules (e.g., nucleic acid barcode molecules) may be generated on the same support (e.g., bead). For example, a bead may comprise a plurality of starter sequences attached thereto, and barcode molecules may be generated using all or a portion of the plurality of starter sequences. The barcode molecules attached to a given support may be the same (e.g., comprising the same barcode sequences, functional sequences, and/or other sequences). In some cases, barcode molecules attached to the same support may differ in unique molecular identifiers included in each barcode molecule. Such barcode molecules may otherwise include the same components.

In some cases, multiple different barcode molecules (e.g., nucleic acid barcode molecules) may be generated on the same support (e.g., bead). For example, two different barcode molecules may be generated on the same support. Alternatively, three or more different barcode molecules may be generated on the same support. Different barcode molecules attached to the same support may comprise one or more different sequences. For example, different barcode molecules may comprise one or more different barcode sequences, functional sequences, and/or other sequences (e.g., starter sequences). In some cases, different barcode molecules attached to the same support may comprise the same barcode sequences and different functional sequences. For example, a first barcode molecule attached to a support may comprise a first functional sequence (e.g., a random N-mer) that is a capture sequence (e.g., for capturing a deoxyribonucleic acid (DNA) molecule), while a second barcode molecule attached to the same support may comprise a second functional sequence that is a poly(T) sequence (e.g., for capturing a messenger ribonucleic acid (mRNA) molecule which may comprise a poly(A) sequence). Different barcode molecules attached to the same support may comprise barcode sequences that are the same or different. Similarly, different barcode molecules may comprise unique molecular identifiers (UMIs) that are the same or different. Different barcode molecules attached to the same support may have several different configurations. A first barcode molecule attached to a support may comprise a first functional sequence, a first barcode sequence, and a first starter sequence, and a second barcode molecule attached to the same support may comprise a second functional sequence, a second barcode sequence, and a second starter sequence. In a first example, the first and second barcode sequences may be the same, the first and second functional sequences may be the same, and the first and second starter sequences may be different. Such a configuration may facilitate performing different assays (e.g., sequencing methods) on the same target molecules. In a second example, the first and second barcode sequences may be the same, the first and second functional sequences may be different, and the first and second starter sequences may be the same. Such a configuration may facilitate performing different assays on different target molecules (e.g., RNA and DNA molecules). In a third example, the first and second barcode sequences may be different, the first and second functional sequences may be the same, and the first and second starter sequences may be the same. Such a configuration may facilitate sample preparation for multiple different subsequent assays (e.g., a first population processed using the first barcode molecules can be separated from a second population processed using the second barcode molecules). In other examples, any first pair of first and second sequences (e.g., functional sequence, barcode sequence, or starter sequence) in first and second barcode molecules may be the same, and second and third pairs of first and second sequences (not the first pair) may be different. In other examples, any first and second pairs of first and second sequences (e.g., functional sequence, barcode sequence, or starter sequence) in first and second barcode molecules may be the same, and a third pair of first and second sequences (not the first or second pair) may be different.

Figure 15:
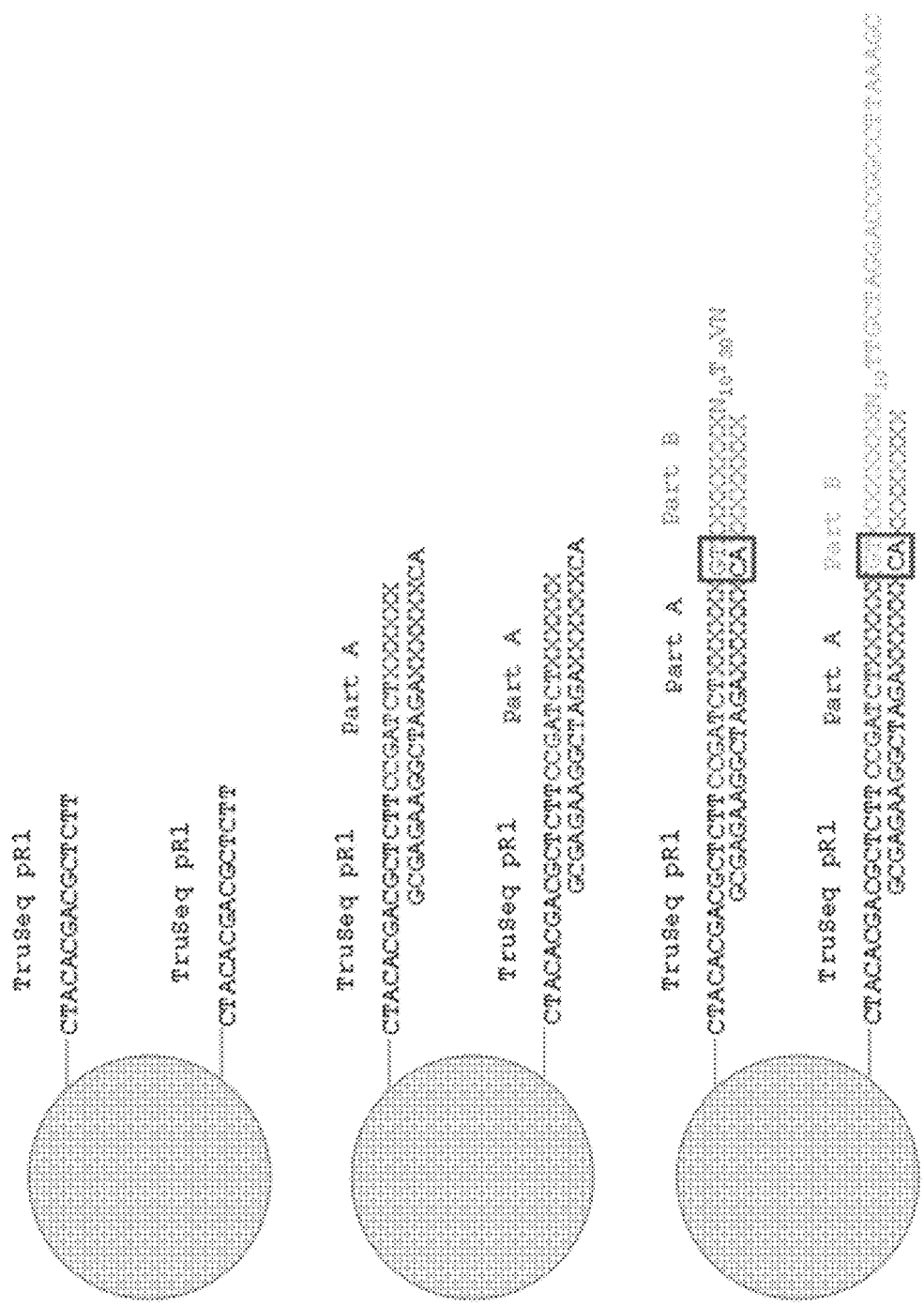
FIG. 15 illustrates a double ligation reaction to provide two different nucleic acid barcode molecules.

FIG. 15 shows an example of a double ligation method involving a bead comprising a plurality of TruSeq sequences. The TruSeq sequences attached to the bead comprise the same sequence. Accordingly, the same first nucleic acid molecule can be ligated to each TruSeq sequence. In the third panel, a second nucleic acid molecule comprising a functional sequence comprising a poly(T) sequence attaches to a first nucleic acid molecule, and a second nucleic acid molecule comprising a functional sequence comprising a capture sequence attached to another first nucleic acid molecule. The second barcode sequences of each second nucleic acid molecule may be the same. Accordingly, FIG. 15 demonstrates double ligation to generate multiple different nucleic acid barcode molecules attached to the same bead.

Figure 16:
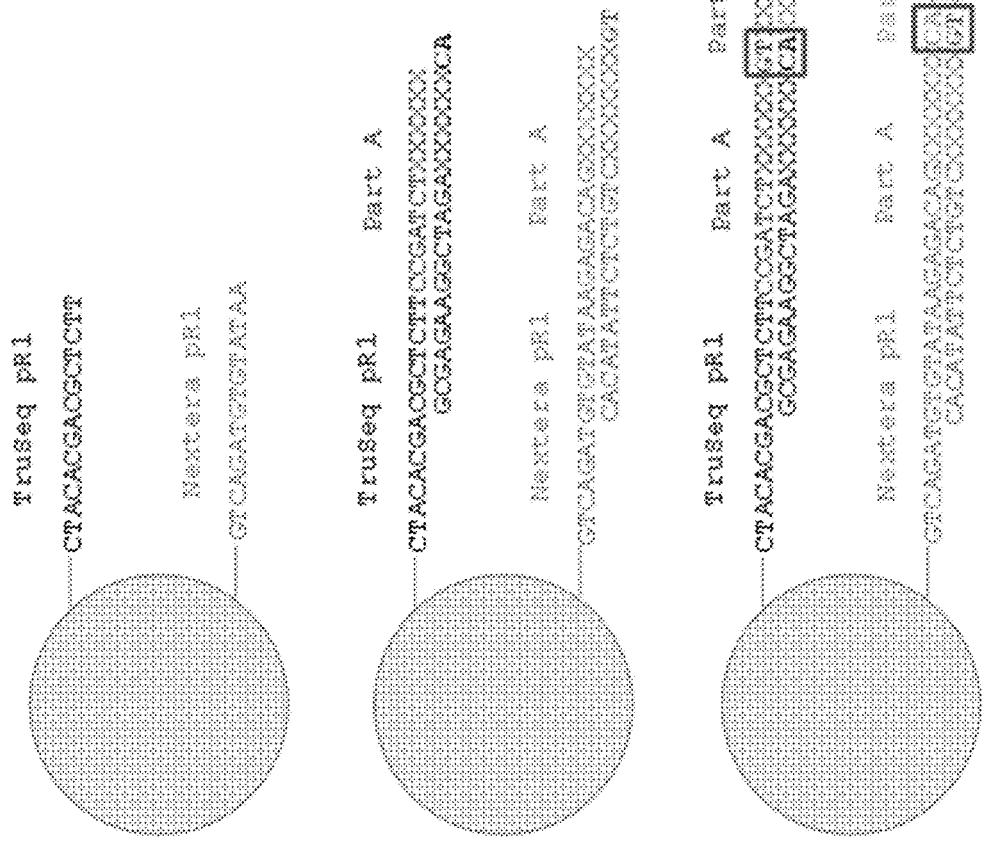
FIG. 16 illustrates a double ligation reaction to provide two different nucleic acid barcode molecules.

Different overhang sequences may be used to direct the formation of different nucleic acid barcode molecules associated with the same bead. FIG. 16 shows an example of a double ligation method involving a bead comprising a first starter sequence that is a TruSeq sequence and a second starter sequence that is a Nextera sequence. The first and second starter sequences comprise different nucleic acid sequences. Accordingly, different first nucleic acid molecules ligate to each different starter sequence. In the second panel of FIG. 16, different first nucleic acid molecules are shown ligated to the different starter sequences (e.g., the TruSeq and Nextera sequences). The first nucleic acid molecule ligated to the TruSeq sequence comprises a sequence that is complementary to a portion of the TruSeq sequence, a first barcode sequence, and a first overhang sequence. The first overhang sequence comprises two nucleotides, CA. The first nucleic acid molecule ligated to the Nextera sequence comprises a sequence that is complementary to a portion of the Nextera sequence, a first barcode sequence that is the same or different from the first barcode sequence of the other first nucleic acid molecule, and a first overhang sequence that is different from the first overhang sequence of the other first nucleic acid molecule. The first overhang sequence corresponding to the Nextera sequence is a two nucleotide sequence, GT. By using first nucleic acid molecules with different overhang sequences, the second nucleic acid molecules that ligate to first nucleic acid molecules attached to the different starter sequences can be maintained. Accordingly, the overhang sequences prove useful as indices for controlling the generation of barcode molecules attached to the bead. In the bottom panel of FIG. 16, different second nucleic acid molecules are shown ligated to the different first nucleic acid molecules ligated to TruSeq and Nextera sequences. The second nucleic acid molecule corresponding to the TruSeq sequence comprises a first complementary overhang sequence with a sequence complementary to the first overhang sequence of the first nucleic acid molecule corresponding to the TruSeq sequence. Accordingly, the complementary overhang sequence has a sequence GT. The second nucleic acid molecule corresponding to the Nextera sequence comprises a complementary overhang sequence with a sequence complementary to the first overhang sequence of the first nucleic acid molecule corresponding to the Nextera sequence. Accordingly, the complementary overhang sequence has a sequence CA. Each second nucleic acid molecule further comprises a second barcode sequence and a functional sequence. The second barcode sequences of the second nucleic acid molecules may be the same or different. The functional sequences of the second nucleic acid molecules may be different. For example, the functional sequence of the second nucleic acid molecule corresponding to the TruSeq sequence may comprise a poly(T) sequence, while the functional sequence of the second nucleic acid molecule corresponding to the Nextera sequence may comprise a capture sequence. Each second nucleic acid molecule may further comprise a unique molecular identifier. The unique molecular identifiers of each second nucleic acid molecules may be the same or different. FIG. 12 displays another example of differential functionalization of a bead comprising different starter sequences. The first nucleic acid molecule associated with each starter sequence comprises Parts A and S, and the second nucleic acid molecule associated with each starter sequence comprises Parts B and D. During the first attachment step, a portion of Part S hybridizes to its corresponding starter sequence and an end of Part A ligates to the starter sequence. During the second attachment step, a portion of Part B hybridizes to an overhang sequence of Part S and an end of Part B ligates to an end of Part A. The resultant product is a partial double-stranded nucleic acid barcode molecule. The nucleic acid barcode molecule may be denatured to provide a single-stranded nucleic acid barcode molecule (e.g., as described herein). The first and second nucleic acid molecules of FIG. 12 share the same first and second barcode sequences (shown highlighted). As indicated in the key, the overhang sequence associated with the TruSeq starter sequences is referred to as an "alpha" overhang, while the overhang sequence associated with the Nextera starter sequence is referred to as a "beta" overhang.

Figure 19:
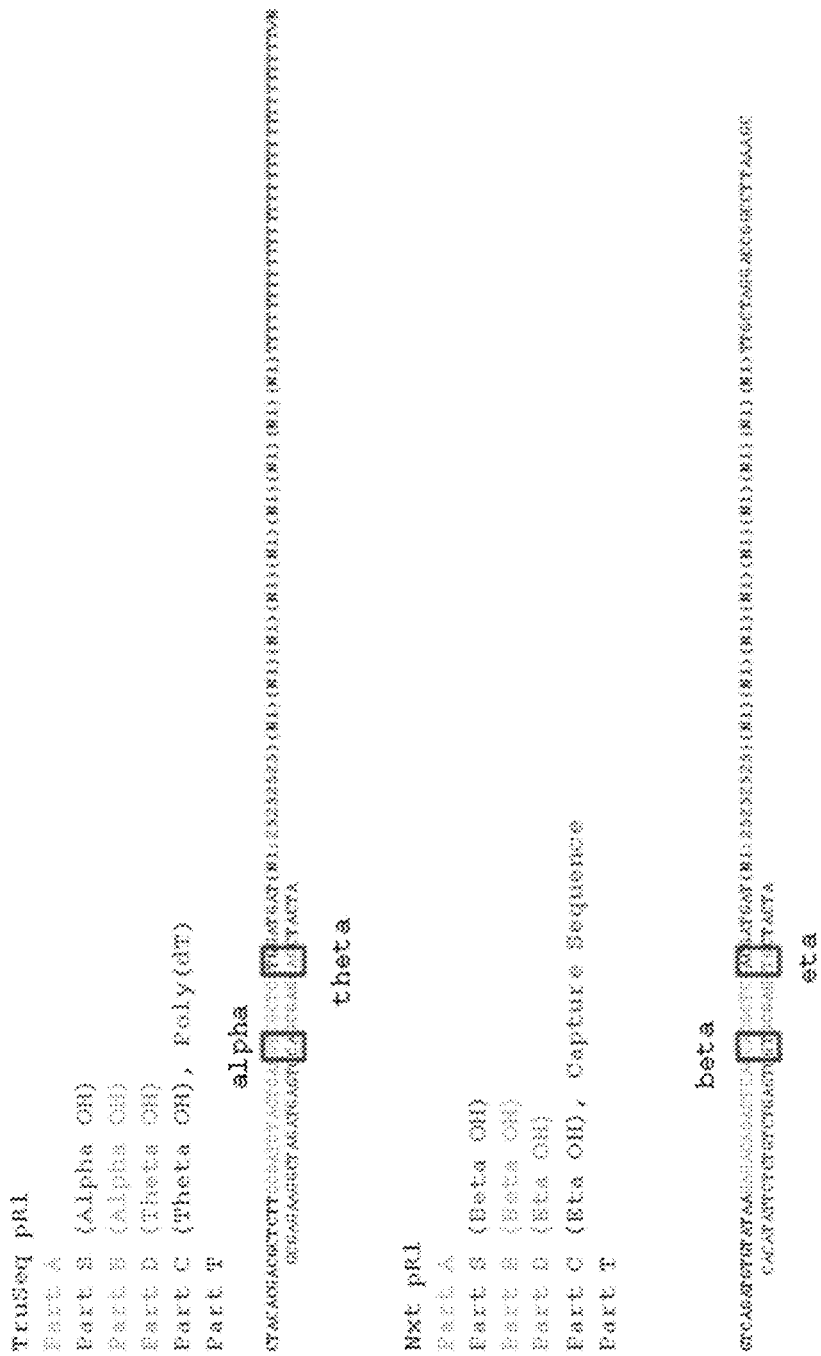
FIG. 19 shows a comparison of the nucleic acid barcode molecules of FIGS. 17 and 18.

Triple ligation may also be employed to generate barcode molecules attached to beads, as described above. FIG. 17 shows an example of functionalization of a bead comprising a TruSeq starter sequence using triple ligation. The first nucleic acid molecule comprises Parts A and S, the second nucleic acid molecule comprises Parts B and D, and the third nucleic acid molecule comprises Parts C and T. Part S comprises a sequence that is complementary to a portion of the TruSeq starter sequence on one end and an overhang sequence CA on the second end. The overhang sequence CA may be referred to as an "alpha" overhang. Part S also comprises a sequence complementary to a first barcode sequence of Part A. Part B comprises a complementary overhang sequence GT that is complementary to the alpha overhang. Part B further comprises a second barcode sequence and Part D comprises a sequence that is complementary to the second barcode sequence. Part D further comprises a second overhang sequence comprising the sequence AC. The second overhang sequence AC may be referred to as a "theta" overhang. Part C comprises a second complementary overhang sequence that is complementary to the theta overhang. Part C further comprises a third barcode sequence and a functional sequence, while Part T comprises a sequence that is complementary to the third barcode sequence. Similarly, FIG. 18 shows an example of functionalization of a bead comprising a Nextera starter sequence using triple ligation. The first nucleic acid molecule comprises Parts A and S, the second nucleic acid molecule comprises Parts B and D, and the third nucleic acid molecule comprises Parts C and T. Part S comprises a sequence that is complementary to a portion of the Nextera starter sequence on one end and an overhang sequence GT on the second end. The overhang sequence GT may be referred to as a "beta" overhang. Part S also comprises a sequence complementary to a first barcode sequence of Part A. Part B comprises a complementary overhang sequence CA that is complementary to the beta overhang. Part B further comprises a second barcode sequence and Part D comprises a sequence that is complementary to the second barcode sequence. Part D further comprises a second overhang sequence comprising the sequence TG. The second overhang sequence TG may be referred to as an "eta" overhang. Part C comprises a second complementary overhang sequence that is complementary to the eta overhang. Part C further comprises a third barcode sequence and a functional sequence, while Part T comprises a sequence that is complementary to the third barcode sequence. FIG. 19 compares triple ligation for TruSeq and Nextera sequences, highlighting the overhang and complementary overhang sequences therein.

Figure 20:
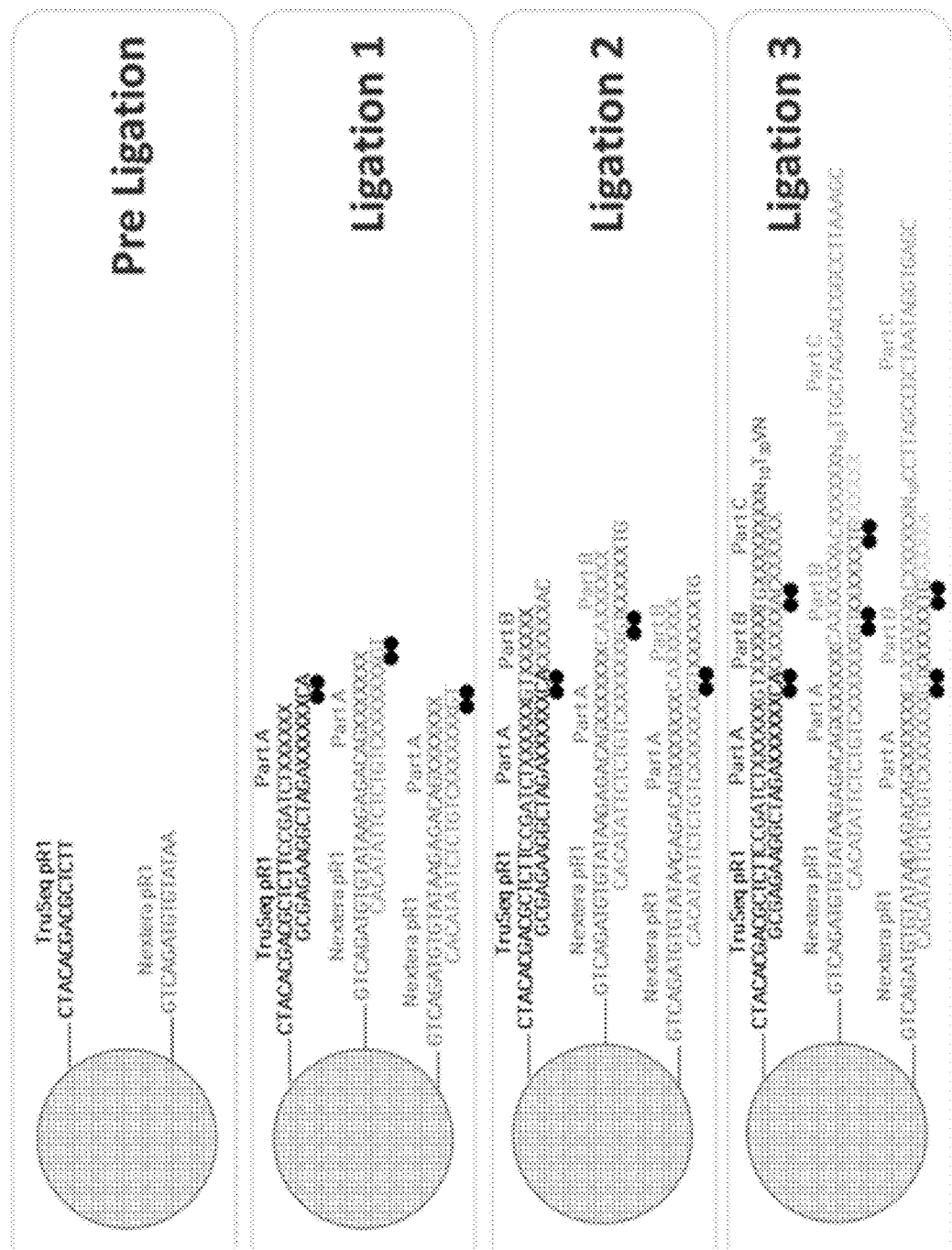
FIG. 20 illustrates a triple ligation reaction to provide three different nucleic acid barcode molecules.

FIG. 20 shows an example of triple ligation method involving a bead comprising a starter sequence comprising a TruSeq sequence and a starter sequence comprising a Nextera sequence. In the second panel, a first nucleic acid molecule comprising a first strand (top strand, indicated as "Part A") and a second strand (bottom strand) is ligated to the TruSeq sequence. The second strand of the first nucleic acid molecule comprises a sequence complementary to a portion of the TruSeq sequence at one end and a two-nucleotide overhang sequence (CA) at a second end. Similarly, a first nucleic acid molecule comprising a first strand (top strand, indicated as "Part A") and a second strand (bottom strand) is ligated to each Nextera sequence. The second strand of the first nucleic acid molecule comprises a sequence complementary to a portion of the Nextera sequence at one end and a two-nucleotide overhang sequence (GT) at a second end. The first strand of each first nucleic acid molecule comprises a first barcode sequence (indicated by the sequence XXXXXX, where X represents a variable nucleotide), and the second strand comprises a sequence complementary to the first barcode sequence. In the third panel, a second nucleic acid molecule comprising a first strand (top strand, indicated as "Part B") and a second strand (bottom strand) is ligated to each first nucleic acid molecule. The first strand of each second nucleic acid molecule comprises a complementary overhang sequence that is complementary to the corresponding overhang sequence of a first nucleic acid molecule, and the second strand of each second nucleic acid molecule comprises an overhang sequence that differs based on the associated starter sequence. Accordingly, the first strand of the second nucleic acid molecule associated with the TruSeq sequence comprises a complementary overhang sequence GT, while the first strand of the second nucleic acid molecule associated with the Nextera sequences comprises a complementary overhang sequence CA. Similarly, the second strand of the second nucleic acid molecule associated with the TruSeq sequence comprises an overhang sequence AC, while the second strand of the second nucleic acid molecule associated with the Nextera sequence comprises an overhang sequence TG. Each second nucleic acid molecule comprises a second barcode sequence (indicated by the sequence XXXXXXXX, where X represents a variable nucleotide) in its first strand, and the complement of the second barcode sequence in its second strand.

In the fourth panel, a third nucleic acid molecule comprising a first strand (top strand, indicated as "Part C") and a second strand (bottom strand) is ligated to each second nucleic acid molecule. The first strand of each third nucleic acid molecule comprises a complementary overhang sequence that is complementary to the corresponding overhang sequence of a second nucleic acid molecule, and the second strand of each third nucleic acid molecule comprises an overhang sequence that differs based on the associated starter sequence. Accordingly, the first strand of the third nucleic acid molecule associated with the TruSeq sequence comprises a complementary overhang sequence TG, while the first strand of the third nucleic acid molecule associated with the Nextera sequences comprises a complementary overhang sequence AC. Each third nucleic acid molecule comprises a third barcode sequence (indicated by the sequence XXXXXXXX, where X represents a variable nucleotide) in its first strand, and the complement of the third barcode sequence, or a portion thereof, in its second strand. The first strand of each third nucleic acid molecule also includes a unique molecular identifier (Nm) and a functional sequence. The functional sequence associated with the TruSeq sequence comprises a poly(T) sequence while the functional sequences associated with the Nextera sequences comprise different capture sequences.

Figure 11:
FIG. 11 shows examples of beads comprising two or more different nucleic acid barcode molecules.

FIG. 11 shows examples of beads including two or more different nucleic acid barcode molecules attached thereto. Each nucleic acid barcode molecule comprises a starter sequence (e.g., a partial read sequence such as a TruSeq or Nextera sequence), a barcode sequence, a unique molecular identifier, and a functional sequence. The barcode sequence may comprise two or more barcode sequences from two or more nucleic acid molecules, as well as one or more overhangs. For example, a double ligation method may be used to generate the nucleic acid barcode molecules such that the barcode sequence may comprise a first barcode sequence from a first nucleic acid molecule, a first overhang sequence or complement thereof, and a second barcode sequence from a second nucleic acid molecule. Alternatively, a triple ligation method may be used to generate the nucleic acid barcode molecules such that the barcode sequence may comprise a first barcode sequence from a first nucleic acid molecule, a first overhang sequence or complement thereof, a second barcode sequence from a second nucleic acid molecule, a second overhang sequence or complement thereof, and a third barcode sequence from a third nucleic acid molecule. Nucleic acid barcode molecules may be differently functionalized (e.g., comprise different functional sequences suited for different applications, such as interaction with different analytes). The functional sequence of a nucleic acid barcode molecule may be included in the second (in the case of double ligation) or third (in the case of triple ligation) nucleic acid molecule used to construct the nucleic acid barcode molecule. The starter sequence to which other components of the nucleic acid barcode molecule attach may dictate the functional sequence of the nucleic acid barcode molecule after double or triple ligation. For example, the middle panel of FIG. 11 shows a bead comprising a TruSeq and a Nextera starter sequence. Because the different starter sequences have different nucleic acid sequences, a different first nucleic acid molecule will ligate to the first (e.g., TruSeq) sequence than will ligate to the second (e.g., Nextera) starter sequence. By designing the first nucleic acid molecules associated with each starter sequence to include different overhang sequences, the second nucleic acid molecule that ligates to each different first nucleic acid molecule may also be controlled. For example, a first nucleic acid molecule that ligates to a first starter sequence may include a first overhang sequence, while a first nucleic acid molecule that ligates to a second starter sequence may include a different first overhang sequence. The second nucleic acid molecule that ligates to the first nucleic acid molecule ligated to the first starter sequence will include a sequence complementary to its overhang sequence, while the second nucleic acid molecule that ligates to the first nucleic acid molecule ligated to the second starter sequence will include a sequence complementary to its overhang sequence which is different from the other overhang sequence. Accordingly, different second nucleic acid molecules may ligate to different first nucleic acid molecules ligated to different starter sequences attached to the same bead based on different overhang sequences. This so-called "overhang control" construction method may facilitate construction of different nucleic acid barcode molecules including different functional sequences on the same bead. Additional nucleic acid molecules (e.g., third nucleic acid molecules, fourth nucleic acid molecules, etc.) may be selectively ligated in a similar fashion. The barcode sequences of the different first, second, third, etc. nucleic acid molecules may be the same such that different nucleic acid barcode molecules comprising different starter sequences may comprise the same barcode sequences.

Alternatively, concentration and other reaction parameters may be used to control the nucleic acid barcode molecules formed in a so-called "concentration control" construction method. For example, the top panel of FIG. 11 shows two different nucleic acid barcode molecules attached to a bead, where each nucleic acid barcode molecule comprises the same starter sequence (e.g., a TruSeq sequence). The barcode sequence associated with each nucleic acid barcode molecule may be the same. In order to achieve multiple different nucleic acid barcode molecules attached to a bead, different concentrations of a second or third nucleic acid molecule comprising a first functional sequence and a second or third nucleic acid molecule comprising a second functional sequence may be added to a ligation reaction mixture. For example, for a double ligation reaction, equal concentrations of a second nucleic acid molecule comprising a first functional sequence and a second nucleic acid molecule comprising a second functional sequence may be added to the ligation reaction mixture, which may result in equal concentrations of the first and second functional sequences attached to a bead. Alternatively, a higher concentration of second nucleic acid molecules including a first functional sequence may be used to provide a bead comprising a higher concentration of the first functional sequence than a second functional sequence. A mixture comprising second nucleic acid molecules comprising first functional sequences and second nucleic acid molecules comprising second functional sequences may comprise greater than 50% second nucleic acid molecules comprising first functional sequences, such as 51%, 52%, 55%, 60%, 65%, 70%, 75%, 80%, 85%, 90%, 95%, or more second nucleic acid molecules comprising first functional sequences. A mixture comprising second nucleic acid molecules comprising first functional sequences and second nucleic acid molecules comprising second functional sequences may be designed to provide a bead comprising greater than 50% nucleic acid barcode molecules comprising first functional sequences, such as 51%, 52%, 55%, 60%, 65%, 70%, 75%, 80%, 85%, 90%, 95%, or more nucleic acid barcode molecules comprising first functional sequences. Accordingly, different second nucleic acid molecules may ligate to the same first nucleic acid molecules ligated to the same starter sequences attached to the same bead based on different concentrations. The same method may be applied for triple ligation using beads comprising the same starter sequences, first nucleic acid molecules, and second nucleic acid molecules and different third nucleic acid molecules comprising different functional sequences. The "concentration control" construction method may thus facilitate construction of different nucleic acid barcode molecules including different functional sequences on the same bead. The barcode sequences of the first, second, third, etc. nucleic acid molecules may be the same such that different nucleic acid barcode molecules comprising different starter sequences may comprise the same barcode sequences.

The bottom panel of FIG. 11 shows a bead comprising a first nucleic acid barcode molecule comprising a first starter sequence (e.g., a TruSeq sequence) and second and third nucleic acid barcode molecules comprising second starter sequences (e.g., Nextera sequences). The barcode sequence associated with each different nucleic acid barcode molecule may be the same. As described with regard to the top and middle panels of FIG. 11, overhang and concentration control construction methods may be used to construct different nucleic acid molecules attached to the same bead. For example, overhang sequences may be used to direct the generation of a particular first nucleic acid barcode molecule comprising the first starter sequence, while concentration control may be used to direct the generation of the second and third nucleic acid barcode molecules comprising the second starter sequences in a given ratio.

A concentration control scheme may be used to block a given barcode molecule from being produced (e.g., in a larger quantity) on the support (e.g., bead) by limiting the amount of necessary molecular segments or sequences or other reagents available for the reaction. Alternatively or in addition, one or more molecules or portions thereof coupled to a bead may be blocked to prevent or lessen generation of a given barcode molecule on the support (e.g., bead).

A nucleic acid molecule and/or a starter sequence associated with a support (e.g., bead) may comprise natural and/or non-naturally occurring (e.g., modified) nucleotides. For example, a nucleotide of a nucleic acid molecule and/or starter sequence associated with a bead may comprise any number or concentration of guanine, cytosine, thymine, uracil, and adenine bases, as well as non-naturally occurring (e.g., modified) nucleosides. A modified nucleoside may comprise one or more modifications (e.g., alkylation, hydroxylation, oxidation, or other modification) in its nucleobase and/or sugar moieties. A nucleic acid molecule and/or a starter sequence associated with a bead may comprise a nucleotide comprising a modified phosphate linker moiety. A nucleotide of a nucleic acid molecule and/or starter sequence may comprise one or more detectable moieties such as one or more fluorophores.

A barcode sequence of a barcode molecule (e.g., a nucleic acid barcode molecule) may comprise a first barcode sequence, a second barcode sequence, and, in some cases, a third barcode sequence. A first overhang sequence or a complement thereof and, in some cases, a second overhang sequence or a complement thereof, may be inserted between two or more sequences of a barcode sequence. For example, a barcode sequence may comprise a first barcode sequence and a second barcode sequence flanking an overhang sequence or complement thereof. In some cases, a barcode sequence may comprise, in order, a first barcode sequence, a first overhang sequence or complement thereof, a second barcode sequence, a second overhang sequence or complement thereof, and a third barcode sequence. A barcode sequence may have any useful length and composition. In some cases, a barcode sequence may comprise 4 or more nucleotides, such as 5, 6, 7, 8, 9, 10, 11, 12, 13, 14, 15, 16, 17, 18, 19, 20, 21, 22, 23, 24, 25, 26, 27, 28, 29, 30, or more nucleotides. For example, a barcode sequence may comprise a first barcode sequence comprising 6 nucleotides and a second barcode sequence comprising 8 nucleotides for a total of 14 nucleotides. In another example, a barcode sequence may comprise a first barcode sequence comprising 6 nucleotides, a second barcode sequence comprising 6 nucleotides, and a third barcode sequence comprising 8 nucleotides for a total of 20 nucleotides. A barcode sequence may comprise naturally occurring and/or non-naturally occurring nucleotides. A barcode sequence may comprise any useful sequence and composition of nucleotides. In some cases, all nucleic acid barcode molecules attached to a given bead comprise the same barcode sequences. In other cases, nucleic acid barcode molecules attached to a given bead may comprise different barcode sequences. For example, all nucleic acid barcode molecules may comprise the same first and second barcode sequences and different third barcode sequences. For beads for which all nucleic acid barcode molecules comprise the same barcode sequence, each nucleic acid barcode molecule may comprise a different unique molecular identifier that identifies the nucleic acid barcode molecules attached to the beads.

Figure 21:
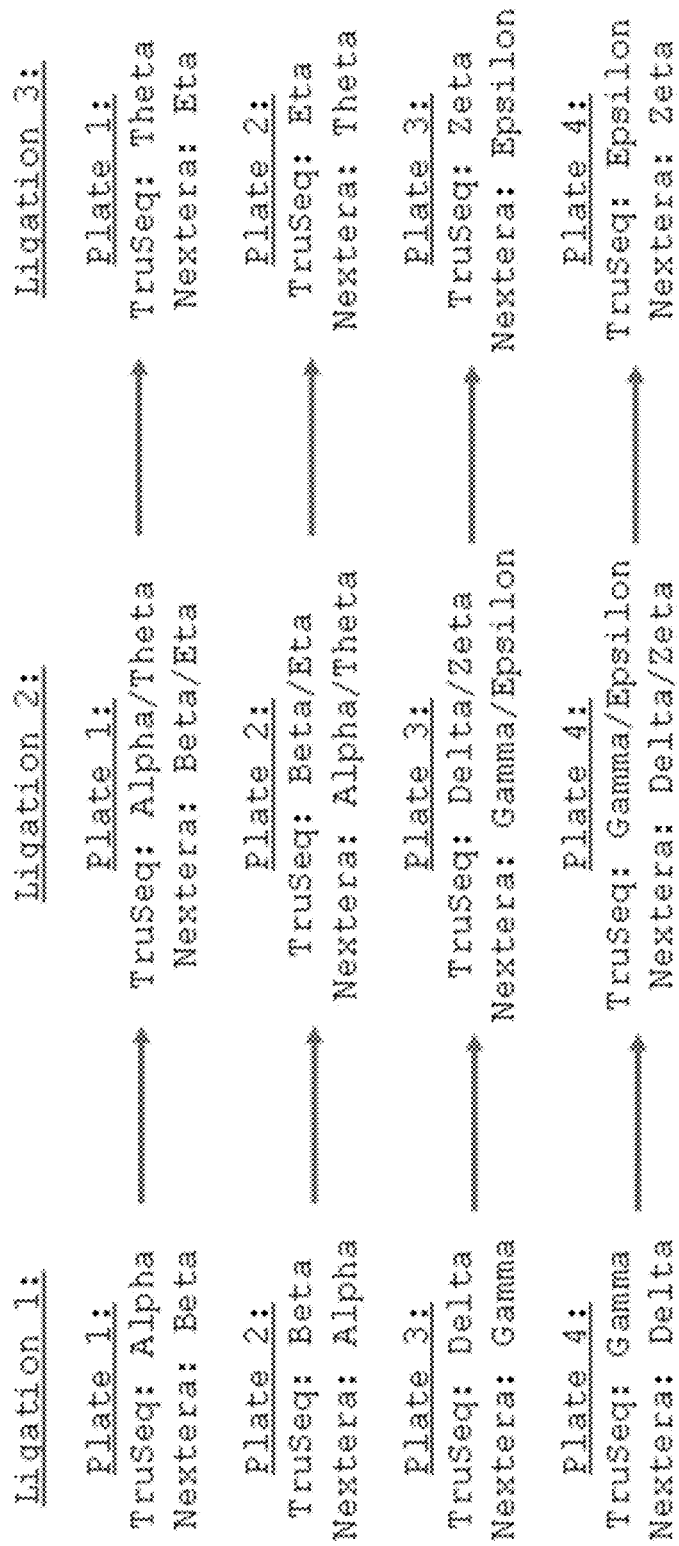
FIG. 21 shows a combinatorial scheme for a triple ligation method.

Overhang sequences may help control the generation of different nucleic acid barcode molecules on a given bead (e.g., as described herein). A given overhang sequence may comprise 2, 3, 4, 5, 6, or more nucleotides. In some cases, the overhang sequence comprises 2 nucleotides. Examples of overhang sequences comprising 2 nucleotides include GT (referred to herein as "alpha"), CA ("beta"), AG ("gamma"), TC ("delta"), GA ("epsilon"), CT ("zeta"), AC ("eta"), and TG ("theta"). FIG. 21 provides a scheme for triple ligation premised on differentiation between overhang sequences. The middle section provides overhang pairs (e.g., a first overhang and a second overhang) that may be used in triple ligation. As indicated therein, alpha and theta overhangs may be used in tandem; beta and eta overhangs may be used in tandem, delta and zeta overhangs may be used in tandem, and gamma and epsilon overhangs may be used in tandem.

Functional sequences may be useful for different applications and assays. For example, a functional sequence capable of hybridizing with an mRNA molecule (e.g., a functional sequence comprising a poly(T) sequence) may facilitate analysis of an mRNA analyte, while a functional sequence capable of hybridizing with a DNA molecule (e.g., a capture sequence, such as a capture sequence comprising a random N-mer) may facilitate analysis of a DNA analyte. A bead comprising a nucleic acid barcode molecule comprising a poly(T) sequence and a nucleic acid barcode molecule comprising a DNA capture sequence may be useful for analyzing an mRNA analyte and a DNA analyte in tandem (e.g., in a multi-assay method). Other examples of functional sequences include functional sequences capable of interacting with other nucleic acid molecules (e.g., transfer RNA (tRNA) molecules, ribosomal RNA (rRNA) molecules, and mitochondrial RNA (mtRNA) molecules), functional sequences capable of interacting with an oligonucleotide coupled to a labeling agent (e.g., an oligonucleotide coupled to a protein or antibody) and capable of detecting a an analyte (e.g., an intracellular protein, extracellular protein, transmembrane protein, or surface protein), and functional sequences capable of interacting with a nucleic acid sequence of or encoding a perturbation agent such as a clustered regularly interspersed short palindromic repeat (CRISPR) agent (e.g., crRNA or sgRNA), transcription-activator like effector nucleases (TALENs, e.g., TALEN mRNA sequence)), zinc finger nucleases (ZFN, e.g., ZFN mRNA sequence), or other perturbation agent. A functional sequence may comprise a random N-mer. In some cases, a functional sequence may be referred to as a "target sequence." Examples of capture and primer sequences useful in nucleic acid barcode molecules of the claimed methods are provided in Table 1 below:

TABLE 1

Sequences for inclusion in nucleic acid barcode molecules

| SEQ ID NO: | Sequence |
| --- | --- |
| 1 | TGCCTTGTAACGCGAA |
| 2 | TATGGCCGCGCAATTA |
| 3 | TTCGAGCGCGCAATTA |
| 4 | ATTGCGCCGAACGTAT |
| 5 | GTTGCACGCGCAATTA |
| 6 | TGCCATTGCGCGATAA |
| 7 | AAGGATCGCGCCTATT |
| 8 | GTTACGCGCGCAATTA |
| 9 | AGCATGTCGCGCATTA |
| 10 | TTCGCAACGGTCGAAT |
| 11 | ATTGCGCGCGAATTAC |
| 12 | TCTTAGCGGACGCAAT |
| 13 | ATCCATGGCGCGATTA |
| 14 | GTTCGCACGCGAATTA |
| 15 | CGATTGCGCGACATTA |
| 16 | TGATCGCGCTACGAAT |
| 17 | CGCATTCAATTGGCGA |
| 18 | AACGTTCGCGATTGAC |
| 19 | GCTTGACCGCGAATTA |
| 20 | ACTGCGCGATTCGTAA |
| 21 | TCCAATAATGCGCGGT |
| 22 | AGTCATCGACCGGATT |
| 23 | AGACTTCGCGCGATTA |
| 24 | CTGAGTCGCGCAATTA |
| 25 | TCGCTAACGGTCGAAT |
| 26 | TATGCGCGCGAATTAC |
| 27 | TATGCGCGCTACGAAT |
| 28 | AACTGCGCGATTCGTA |
| 29 | TGGACCGCGCATATTA |
| 30 | TATCACAATGCGCGGT |
| 31 | GTCACGCGCGAATTAT |
| 32 | GTCTAGCGCGCAATTA |
| 33 | TCTGCAACGGTCGAAT |
| 34 | CCAGTGCGCGAATTAT |
| 35 | ATCGTCACGCGATTAG |
| 36 | GCCAATCGACGTTAGT |
| 37 | TTAGCGCGCGAATTAC |
| 38 | TCGATCAGTTACGCGA |
| 39 | ACCTGAATACGCGGTT |
| 40 | TGCGGTCGAACCTAAT |

TABLE 1-continued

Sequences for inclusion in nucleic acid barcode molecules

| SEQ ID NO: | Sequence |
|---|---|
| 41 | TGAACGCGCTACTATG |
| 42 | TGGCTTAATCGCGACA |
| 43 | TAGGTCCGCGACATTA |
| 44 | CCTTGGCGAACGATTA |
| 45 | AAGTCCGCGCGATTAT |
| 46 | GACTGTCGCGCAATTA |
| 47 | TTAGGTCCGCTACGAA |
| 48 | TCTGTGAACCGTCGAA |
| 49 | GTCACAATACGCGGTT |
| 50 | GAGACTTCGCGCATTA |
| 51 | GAGCAATTCGCGCTAT |
| 52 | CGTTACGATTACGCGA |
| 53 | AGCACGTAATCGTTCG |
| 54 | GCGTTACCGAACGTAT |
| 55 | TTAACGACCGGTTACG |
| 56 | ATTGCGCGCGATACTA |
| 57 | CTGTTGACCGCGAATA |
| 58 | GCAAGATTCGCGCTAT |
| 59 | GGCCATCGCGAATTAT |
| 60 | ATGGACCGCGCTATTA |
| 61 | ACGCGATAATCGTTCG |
| 62 | TAGGCATTATCCGCGA |
| 63 | TCAGCTCGAACGGTTA |
| 64 | CATTCAATTGCGCGAG |
| 65 | GCTCAATTACGCGGAT |
| 66 | ACGGATCGCATCGTTA |
| 67 | CTGCAATTACGCGGAT |
| 68 | TGTCGATTACGCGAAC |
| 69 | ACCTAGGCGCGATTAT |
| 70 | CGCGTAGCGCATATTA |
| 71 | CAATCGTTACGCGGAT |
| 72 | TAACGCTTACGCGGAT |
| 73 | GCTAACGCGATTCGTA |
| 74 | ATTCCTAATGCGCGAG |
| 75 | TTCACTAATGCGCGAG |
| 76 | CAAGGATTCGCGCTAT |
| 77 | ACGATTCGACCGGTAT |

TABLE 1-continued

Sequences for inclusion in nucleic acid barcode molecules

| SEQ ID NO: | Sequence |
|---|---|
| 78 | GAGCAACTATTCGCGT |
| 79 | TACCTACGATTGCGAG |
| 80 | TAATCGACCGGTTACG |
| 81 | GTTCACAATACGCGGT |
| 82 | GCTAGCGCGCATATTA |
| 83 | ACTGACTTACGCGGAT |
| 84 | GCACGTTCGCGTAATA |
| 85 | AAGGTCCGCGCTATTA |
| 86 | CTAGTGAACGCGCTAT |
| 87 | GGCCATCGATTCGTAA |
| 88 | ACCTTGCGCGATAGTA |
| 89 | CTAGGTCCGCGAATTA |
| 90 | ATATCGACCGGTTACG |
| 91 | ATAGCTTATGCGCGAC |
| 92 | ACGTTAATCGGTACGC |
| 93 | CATCATCGATTGCGAG |
| 94 | GTAACTCGACCGGATT |
| 95 | TCGAACGCGTATTAGC |
| 96 | TAGTCGACCGATTACG |
| 97 | GATCACGCGATTCGTA |
| 98 | AGTTAGCGTTACGACC |
| 99 | GCTCAATAAGTCGCGT |
| 100 | CTTAGGCGCGAATTAC |
| 101 | TAGGTCACGTTACGAC |
| 102 | ATACCTTATGCGCGAG |
| 103 | GCACGATAGTTCGCTA |
| 104 | GTCATACAATTCGCGG |
| 105 | CGACTATTATGCGCGA |
| 106 | TAAGCCGCGTATTAGC |
| 107 | CGAATTCGACCGGTAT |
| 108 | CGTCAATAATCGCGTG |
| 109 | GGAACCTTAATCGCGT |
| 110 | GCTCAATAATCGCGTG |
| 111 | CCAATGCGCGTTAGTA |
| 112 | GAACTTCGACCGGTAT |
| 113 | CGCTTAATCGAACGGT |
| 114 | CCTTGAGTCGAACGAT |

TABLE 1-continued

Sequences for inclusion in nucleic acid barcode molecules

| SEQ ID NO: | Sequence |
| --- | --- |
| 115 | ATCGAGTAACCGTTCG |
| 116 | TACCGTAACGTAGTCG |
| 117 | GTTCTCATCGAACGGA |
| 118 | ATCTTGAATCGCGACG |
| 119 | AGACCTTAATCGCGTG |
| 120 | GACCAATATGTCGCGT |
| 121 | CGTAATCGACCGGTAT |
| 122 | GTACACTAAGTCGCGT |
| 123 | TAGTACCGATTGACCG |
| 124 | AGTCTAATCGGTACGC |
| 125 | GTACTGACCGATTACG |
| 126 | CCTTGAATCGAACGGT |
| 127 | TCGACTAATCGGTACG |
| 128 | GCGGATTACGCTACTA |
| 129 | CCTTAGTAGTACGCGA |
| 130 | CCTTAAGTTACGCGAG |
| 131 | GTAAGTACGCGCTATC |
| 132 | CTGTCGCGATCGATAA |
| 133 | GGACAATCGCTCGTTA |
| 134 | GTCCGTCGATCGATAA |
| 135 | GACTTACGACCGGTAT |
| 136 | CTGTTAATCGACCGGA |
| 137 | ATGCGGTAACCTATCG |
| 138 | AGATAGTTACGCGTCC |
| 139 | GAGTCCAACTATCGGT |
| 140 | TTACAGTACTAGCGGC |
| 141 | GACTAATACGCGTTCG |
| 142 | TGGTAACTATACCGGC |
| 143 | CGTACGTAACTATCGG |
| 144 | GACCTTAATCGGTACG |
| 145 | CATTACCGGATAGTCG |
| 146 | GATAGTTATCGCACCG |
| 147 | ACTAGTCGTACGATGC |
| 148 | GATCACTAATCGCGTG |
| 149 | GCGTTACGCTAATACG |
| 150 | CACGATCGTACGGTAT |
| 151 | TGTACGTACGATCCGA |
| 152 | CTAGACTAATCGCGTG |
| 153 | CATAGTCGTACGATGC |
| 154 | GTCGACTAACTATCGG |

Additional examples of capture and primer sequences that may be included in nucleic acid barcode molecules are included in Table 2 below:

TABLE 2

Sequences for inclusion in nucleic acid barcode molecules

| SEQ ID NO: | Sequence |
| --- | --- |
| 155 | /CCTTAGCCGCTAATAGGTGAGC |
| 156 | /TTGCTAGGACCGGCCTTAAAGC |
| 157 | /GAGGATTGCGCACCTTACTAGC |
| 158 | /CAACTTTAGCGGTCCAAGGTGC |
| 159 | /ACGCTAGTTTCGCGTACGAAGC |
| 160 | /ACGCTAGTTTCGCGTACGAAGC |
| 161 | /GAGGATTGCGCACCTTACTAGC |
| 162 | /TTGCTAGGACCGGCCTTAAAGC |
| 163 | /GACAATTGTCGGCTCGACTAGC |

In some cases, a barcode molecule (e.g., a nucleic acid barcode molecule) may comprise a sequence selected from the sequences included in Tables 1 and 2. In some cases, a barcode molecule may comprise a complement or reverse complement of a sequence selected from the sequences included in Tables 1 and 2. In some embodiments, a particular analyte of interest (e.g., nucleic acid, cell surface protein, CRISPR RNA or other perturbation agent) may comprise, may be coupled to, or otherwise associated with an oligonucleotide comprising a sequence that is at least partially complementary to a sequence on a barcode molecule (e.g., a sequence in Table 1 or 2).

Figure 9A:
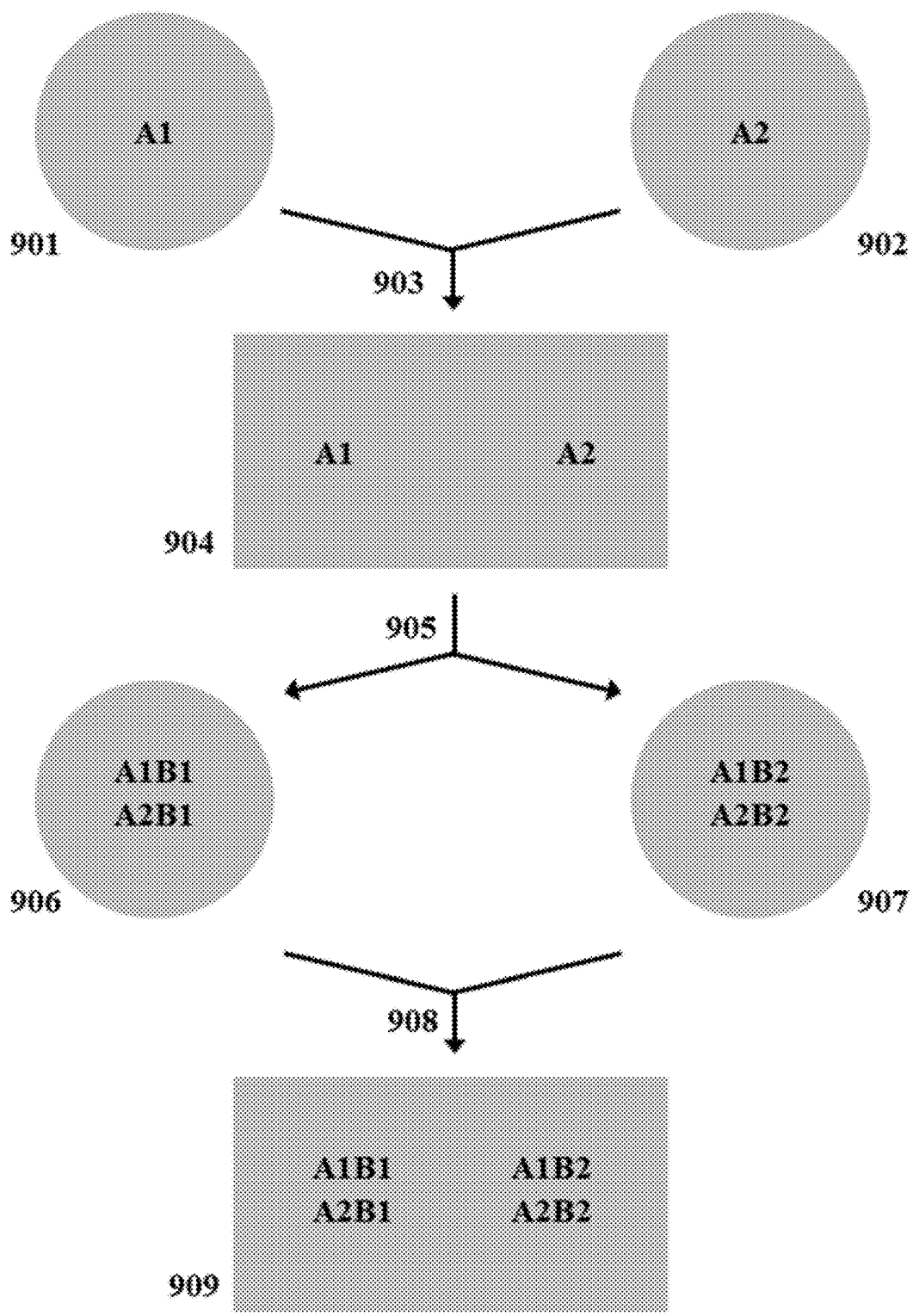
FIG. 9A schematically illustrates a combinatorial double ligation method.
Figure 9B:
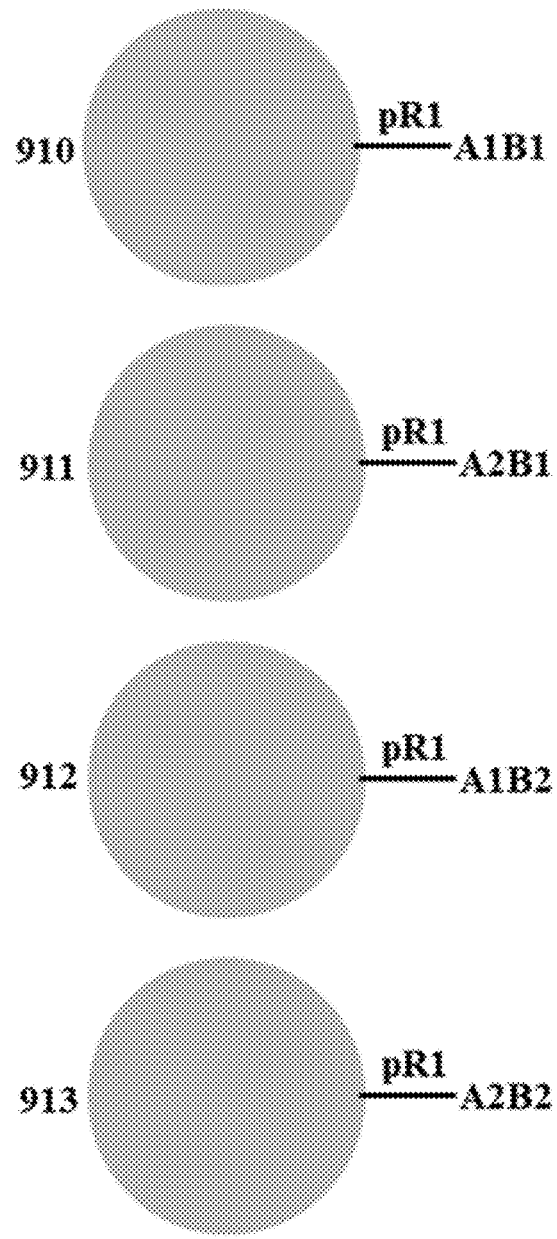
FIG. 9B shows the results of the combinatorial double ligation method.

Multiple ligation reactions used in the preparation of barcode molecules (e.g., nucleic acid barcode molecules) according to the methods provided herein may be performed in a combinatorial fashion. Combinatorial (e.g., split pool) approaches permit the generation of a high diversity of barcode molecules (e.g., barcoded beads) using a reduced number of molecules (e.g., nucleic acid molecules). A combinatorial scheme involves assembling multiple molecular segments or sequences (e.g., a nucleic acid molecule or a portion thereof) to provide a larger molecule (e.g., a molecule comprising two or more molecular segments or sequences). FIG. 9A provides an example of a simplified combinatorial double ligation scheme (e.g., a split pool scheme). Partition 901 includes a plurality of beads comprising a starter sequence and a first molecule A1. Partition 902 includes a plurality of beads comprising a starter sequence and a first molecule A2. First molecules A1 are ligated to the beads of partition 901, and first molecules A2 are ligated to the beads of partition 902. Subsequent to this first ligation step, in process 903 beads of partition 901 and beads of partition 902 are pooled in container 904. Container 904 includes a pooled mixture comprising beads functionalized with first molecule A1 and beads functionalized with first n molecule A2. The pooled mixture is then partitioned between partitions 906 and 907. Partitions 906 and 907 therefore each include beads functionalized with first molecule A1 and beads functionalized with first molecule A2. Partition 906 includes second molecules B1 and partition 907 includes second molecules B2. Second molecules B1 are ligated to the beads of partition 906 to generate beads functionalized with A1 and B1 and beads functionalized with A2 and B1, and second molecules B2 are ligated to the beads of partition 907 to generate beads functionalized with A1 and B2 and beads functionalized with A2 and B2. Subsequent to this second ligation step, in process 908 beads of partition 906 and beads of partition 907 are pooled in container 909. Container 909 includes a pooled mixture comprising beads functionalized with A1 and B1, A1 and B2, A2 and B1, and A2 and B2. The differentially functionalized beads 910, 911, 912, and 913 are shown in FIG. 9B. These beads may be divided amongst different partitions and used for analysis of different analytes. For example, a single bead of the collection of beads may be co-partitioned with a single biological particle (e.g., a cell) comprising an analyte and one or more reagents. A plurality of partitions may be similarly generated (e.g., as described herein) such that each partition includes a bead having attached thereto a differently functionalized barcode molecule.

In some cases, a combinatorial ligation method such as that described with reference to FIG. 9A may comprise immobilizing a plurality of beads to a plurality of supports (e.g., wells of a well plate). The first ligation step may involve providing a plurality of first molecules (e.g., first nucleic acid molecules) to each partition and promoting a ligation reaction. Rather than pooling the plurality of beads from each partition, excess material may be washed out of each partition and a plurality of second molecules (e.g., second nucleic acid molecules) washed into each partition for a second ligation reaction. Accordingly, the methods of the present disclosure may comprise moving beads between partitions or moving fluids between partitions.

The scheme presented in FIG. 9A represents a simplified version of a combinatorial double ligation method (e.g., double ligation split pool method). The complexity of the scheme may be enhanced by providing different versions of the second molecule (e.g., a first version comprising a first functional sequence and a second version comprising a second functional sequence) in the same or different concentration for ligation to the same first molecule of a given bead (e.g., as described herein). This method may involve concentration control construction. Complexity may also be enhanced by providing a bead comprising two or more different starter sequences and employing molecules comprising overhang sequences to direct the generation of particular barcode molecules and provide different barcode molecules attached to the same bead.

Figure 10:
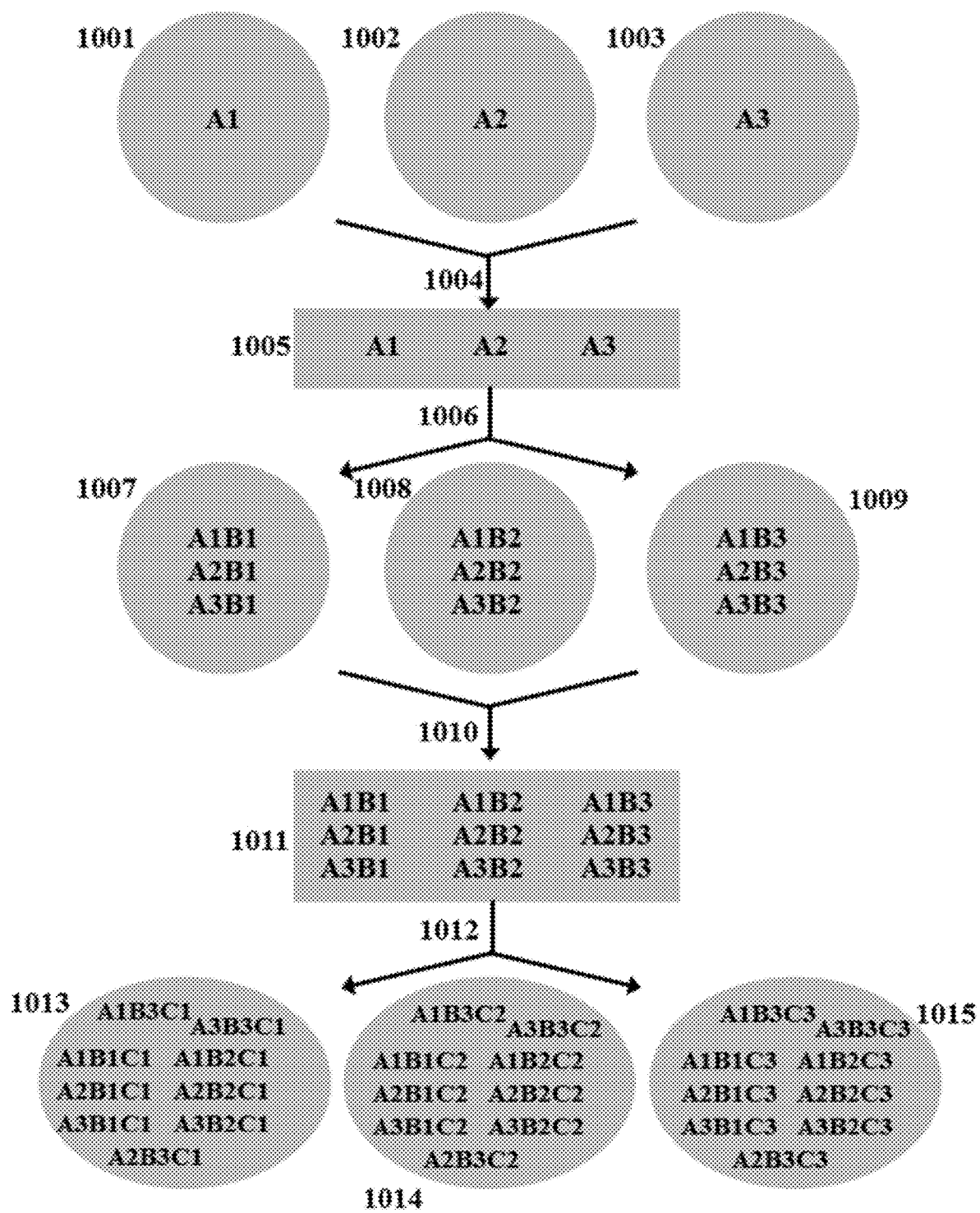
FIG. 10 schematically illustrates a combinatorial triple ligation method.

FIG. 10 provides an example of a simplified combinatorial triple ligation scheme (e.g., triple ligation split pool scheme). Partition 1001 includes a plurality of beads comprising a starter sequence and a first molecule A1. Partition 1002 includes a plurality of beads comprising a starter sequence and a first molecule A2. Partition 1003 includes a plurality of beads comprising a starter sequence and a first molecule A3. First molecules A1 are ligated to the beads of partition 1001, first molecules A2 are ligated to the beads of partition 1002, and first molecules A3 are ligated to the beads of partition 1003. Subsequent to this first ligation step, in process 1004 beads of partitions 1001, 1002, and 1003 are pooled in container 1005. Container 1005 includes a pooled mixture comprising beads functionalized with first molecule A1, beads functionalized with first molecule A2, and beads functionalized with first molecule A3. The pooled mixture is then partitioned in process 1006 between partitions 1007, 1008, and 1009. Partitions 1007, 1008, and 1009 therefore each include beads functionalized with first molecule A1, beads functionalized with first molecule A2, and beads functionalized with first molecule A3. Partition 1007 includes second molecules B1, partition 1008 includes second molecules B2, and partition 1009 includes second molecules B3. Second molecules B1 are ligated to the beads of partition 1007 to generate beads functionalized with A1 and B1, beads functionalized with A2 and B1, and beads functionalized with A3 and B1; second molecules B2 are ligated to the beads of partition 1008 to generate beads functionalized with A1 and B2, beads functionalized with A2 and B2, and beads functionalized with A3 and B2; and second molecules B3 are ligated to the beads of partition 1009 to generate beads functionalized with A1 and B3, beads functionalized with A2 and B3, and beads functionalized with A3 and B3. Subsequent to this second ligation step, in process 1010 beads of partitions 1007, 1008, and 1009 are pooled in container 1011. Container 1011 includes a pooled mixture comprising beads functionalized with A1 and B1, A1 and B2, A1 and B3, A2 and B1, A2 and B2, A2 and B3, A3 and B1, A3 and B2, and A3 and B3.

The pooled mixture is then partitioned in process 1012 between partitions 1013, 1014, and 1015. Partitions 1013, 1014, and 1015 therefore each include beads functionalized with A1 and B1, A1 and B2, A1 and B3, A2 and B1, A2 and B2, A2 and B3, A3 and B1, A3 and B2, and A3 and B3. Partition 1013 includes third molecules C1, partition 1014 includes third molecules C2, and partition 1015 includes third molecules C3. Third molecules C1 are ligated to the beads of partition 1013, third molecules C2 are ligated to the beads of partition 1014, and third molecules C3 are ligated to the beads of partition 1015. Subsequent to this third ligation step, beads of partitions 1013, 1014, and 1015 may be pooled and repartitioned for use in various processing and analysis applications (e.g., as described herein). The resultant pooled mixture comprises beads functionalized as follows: A1B1C1, A2B1C1, A3B1C1, A2B1C1, A2B2C1, A2B3C1, A3B1C1, A3B2C1, A3B3C1, A1B1C2, A2B1C2, A3B1C2, A2B1C2, A2B2C2, A2B3C2, A3B1C2, A3B2C2, A3B3C2, A1B1C3, A2B1C3, A3B1C3, A2B1C3, A2B2C3, A2B3C3, A3B1C3, A3B2C3, and A3B3C3. Accordingly, 9 different molecules (A1, A2, A3, B1, B2, B3, C1, C2, and C3) may be used to generate 27 different barcode molecules. As described elsewhere herein, the use of different starter sequences, overhangs, and controlled concentrations may further increase the number of different barcode molecules generated using the combinatorial (e.g., split pool) method.

Figure 22:
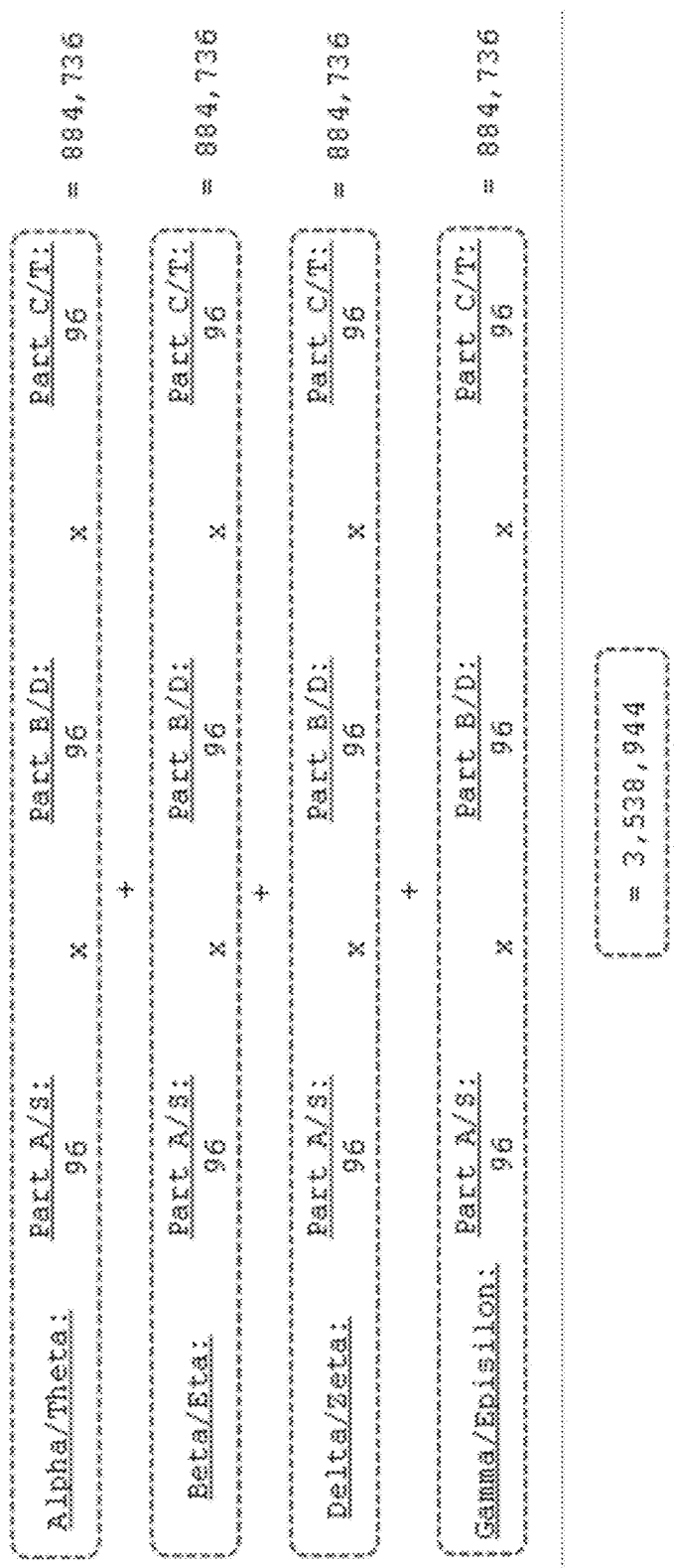
FIG. 22 shows a combinatorial scheme for a triple ligation method.

Double and triple ligation reactions may be carried out in a series of well plates. For example, ligation of first molecules (e.g., first nucleic acid molecules) may be performed within wells of a 96 well plates using, e.g., 96 different first molecules (e.g., as described herein). Each well may also include a plurality of beads and one or more reagents. The plurality of beads may comprise one or more different starter sequences attached thereto. The plate may then be subjected to appropriate reaction conditions (e.g., appropriate pressure, concentration, and temperature conditions with appropriate reagents) to promote ligation between first molecules and starter sequences of beads within each well. Subsequent to this first ligation reaction, the contents of each well may be pooled and mixed. The contents of the resultant pooled mixture may then be redistributed between a plurality of wells in a separate well plate. For example, beads in the pooled mixture may be partitioned among 96 wells of a second 96 well plate. Each well may include a different second molecule (e.g., as described herein) and one or more reagents. The plurality of beads in each well may include beads functionalized with each different first molecule. A second ligation reaction may be performed within each well to generate a plurality of beads comprising the same second molecule and a plurality of different first molecules within each well. The plurality of beads within each well may then be pooled to generate a second pooled mixture. If a third ligation reaction will be performed, the contents of the second pooled mixture may then be partitioned among 96 wells of a third 96 well plate. Each well may include a different third molecule (e.g., as described herein) and one or more reagents. The plurality of beads in each well may include beads functionalized with each different first molecule and each different second molecule. A third ligation reaction may be performed within each well to generate a plurality of beads comprising the same third molecule, a plurality of different first molecules, and a plurality of different second molecules within each well. The plurality of beads within each well may then be pooled to generate a third pooled mixture. Functionalized beads of the third pooled mixture may then be used in further processing or analysis applications (e.g., as described herein). FIG. 21 provides additional details of a triple ligation scheme employing four different plates at each stage of the ligation reaction. FIG. 22 demonstrates the capability of the scheme of FIG. 21 to produce a large number of differently functionalized beads. As shown in FIG. 22, each triple ligation scheme performed using three 96 well plates provides nearly one million beads comprising different barcode molecules. By exploiting different overhang combinations (e.g., alpha/theta, beta/eta, delta/zeta, and gamma/epsilon), the number of different beads comprising different barcode molecules may be enhanced fourfold.

In any of the methods described herein, a double-stranded nucleic acid barcode molecule attached to a bead may be denatured to provide a single-stranded nucleic acid barcode molecule attached to the bead. Denaturation may be achieved controlling, for example, temperature, pressure, and/or pH conditions and/or by employing a chemical or biological agent such as a detergent.

Figure 23:
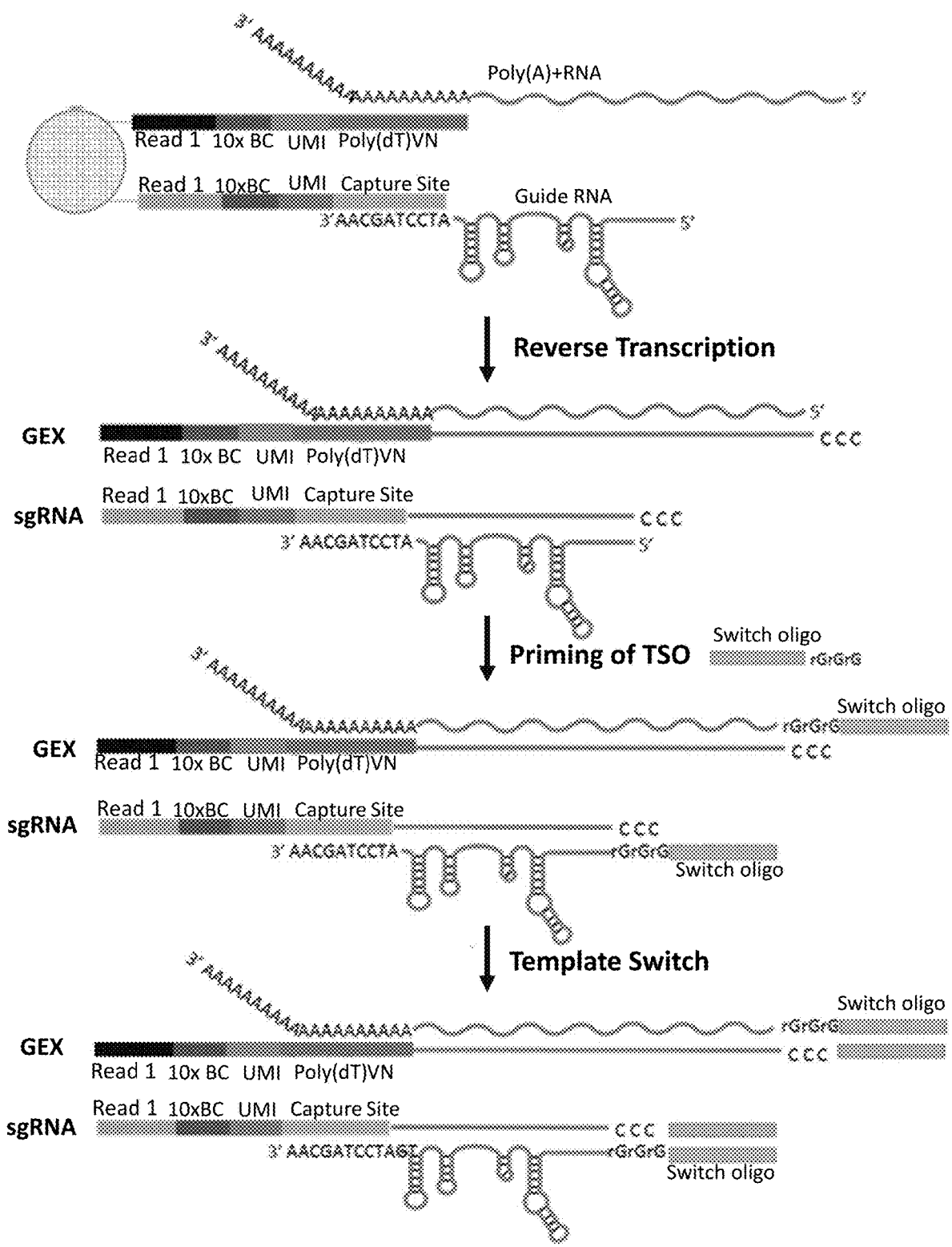
FIG. 23 shows an example of the use of nucleic acid barcode molecules generated by the presently disclosed methods.

In some cases, the methods described herein may be used to screen cells carrying mutations, e.g., mutations generated by gene editing such as CRISPR technology. For example, a bead comprising a first anchor oligonucleotide or nucleic acid molecule with a primer for CRISPR RNA (e.g., crRNA or guide RNA) or its complementary DNA and a second anchor oligonucleotide or nucleic acid molecule with a primer endogenous nucleic acid in the cell, e.g., total mRNA or a specific mRNA. The bead may be made into a partition with a cell transfected with CRISPR RNA or a plasmid expressing CRISPR RNA. In some cases, the expressed CRISPR RNA or the plasmid may have a barcode (CRISPR barcode) or a capture sequence. The primers (e.g., nucleic acid barcode molecules) on the bead may be used to amplify and sequence the CRISPR RNA (e.g., using a nucleic acid barcode molecule comprising a sequence complementary to the CRISPR capture sequence, see FIG. 23) and endogenous mRNA (e.g., using a nucleic acid barcode molecule comprising an oligo(dT) sequence), thus determining the mutations generated by in the cell. In some cases, the methods may be used to perform single cell RNA sequencing, e.g., as described in Dixit, et al., Perturb-Seq: Dissecting Molecular Circuits with Scalable Single-Cell RNA Profiling of Pooled Genetic Screens. Cell; Dec. 15, 2016; 167(7):1853-1866.e17, which is incorporated herein by reference in its entirety.

Figure 24:
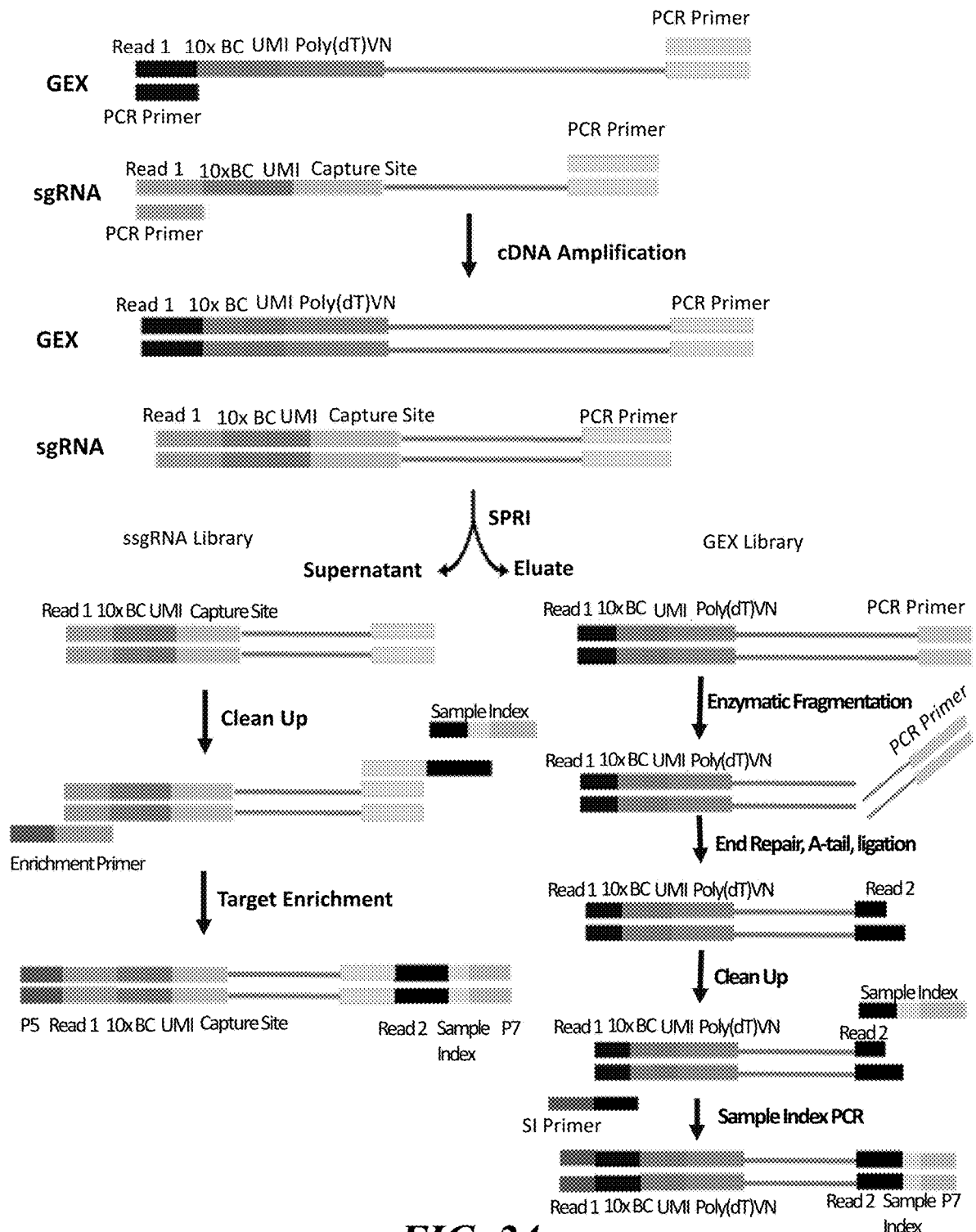
FIG. 24 shows an example of the use of nucleic acid barcode molecules generated by the presently disclosed methods.

As shown in FIG. 24 and described elsewhere herein, beads comprising different nucleic acid barcode molecules generated by the methods described herein may be used to analyze mRNA and DNA sequences simultaneously. For example, mRNA and DNA sequences from the same biological particle (e.g., cell) within a partition may be attached to nucleic acid barcode molecules with the same barcode sequence.

A support (e.g., a bead such as a gel bead) may comprise a plurality of oligonucleotides or barcode molecules (e.g., nucleic acid barcode molecules) attached thereto. The support may comprise at least 10,000 barcode molecules attached thereto. For example, the support may comprise at least 100,000, 1,000,000, or 10,000,000 barcode molecules attached thereto. In any of the methods described herein, one or more oligonucleotides or barcode molecules may be releasably attached to a support. A barcode molecule may be releasable from a support upon application of a stimulus. Such a stimulus may be selected from the group consisting of a thermal stimulus, a photo stimulus, and a chemical stimulus. For example, the stimulus may be a reducing agent such as dithiothreitol Application of a stimulus may result in one or more of (i) cleavage of a linkage between barcode molecules of the plurality of barcode molecules and the support, and (ii) degradation or dissolution of the support (e.g., bead) to release barcode molecules of the plurality of barcode molecules from the support. For a support comprising multiple different barcode molecules, different barcode molecules may be released from the bead upon application of different supports. For example, a first stimulus may be applied to release a first barcode molecule and may not release a second barcode molecule, and a second stimulus may be applied to release the second barcode molecule and may not release the first barcode molecule.

Different analytes capable of being analyzed by a support (e.g., a bead) comprising multiple different barcode molecules or a collection of such supports (e.g., beads) may be contained within or associated with a cell. A cell may be, for example, a human cell, an animal cell, or a plant cell. In some cases, the cell may be derived from a tissue or fluid, as described herein. The cell may be a prokaryotic cell or a eukaryotic cell. The cell may be a lymphocyte such as a B cell or T cell. Access to a plurality of molecules included in a cell may be provided by lysing or permeabilizing the cell. Lysing the cell may release an analyte contained therein from the cell. A cell may be lysed using a lysis agent such as a bioactive agent. A bioactive agent useful for lysing a cell may be, for example, an enzyme (e.g., as described herein). Alternatively, an ionic or non-ionic surfactant such as TritonX-100, Tween 20, sarcosyl, or sodium dodecyl sulfate may be used to lyse a cell. Cell lysis may also be achieved using a cellular disruption method such as an electroporation or a thermal, acoustic, or mechanical disruption method. Alternatively, a cell may be permeabilized to provide access to a plurality of nucleic acid molecules included therein. Permeabilization may involve partially or completely dissolving or disrupting a cell membrane or a portion thereof. Permeabilization may be achieved by, for example, contacting a cell membrane with an organic solvent or a detergent such as Triton X-100 or NP-40.

A biological particle (e.g., a cell) including an analyte may be partitioned with a bead comprising one or more nucleic acid barcode molecules within a partition such as a well or droplet, e.g., as described herein. One or more reagents may be co-partitioned with a cell and bead. For example, a cell may be co-partitioned with one or more reagents selected from the group consisting of lysis agents or buffers, permeabilizing agents, enzymes (e.g., enzymes capable of digesting one or more nucleic acid molecules, extending one or more nucleic acid molecules, reverse transcribing an RNA molecule, permeabilizing or lysing a cell, or carrying out other actions), fluorophores, oligonucleotides, primers, barcodes, nucleic acid barcode molecules (e.g., nucleic acid barcode molecules comprising one or more barcode sequences), buffers, deoxynucleotide triphosphates, detergents, reducing agents, chelating agents, oxidizing agents, nanoparticles, beads, and antibodies. In some cases, a cell and bead may be co-partitioned with one or more reagents selected from the group consisting of temperature-sensitive enzymes, pH-sensitive enzymes, light-sensitive enzymes, reverse transcriptases, proteases, ligase, polymerases, restriction enzymes, nucleases, protease inhibitors, exonucleases, and nuclease inhibitors. For example, a cell and a bead may be co-partitioned with a reverse transcriptase and nucleotide molecules. Partitioning a cell, a bead, and one or more reagents may comprise flowing a first phase comprising an aqueous fluid, the cell, the bead, and the one or more reagents and a second phase comprising a fluid that is immiscible with the aqueous fluid toward a junction. Upon interaction of the first and second phases, a discrete droplet of the first phase comprising the cell, bead, and the one or more reagents may be formed. In some cases, the partition may comprise a single cell and a single bead. The cell may be lysed or permeabilized within the partition (e.g., droplet) to provide access to the plurality of molecules of the cell. Accordingly, molecules originating from the same cell may be isolated and barcoded within the same partition with the same barcode.

Combinatorial (e.g., split pool) ligation approaches such as those provided herein may generate significant diversity of barcode molecules. However, in some cases, unwanted off-products may also be generated. This may be due to ligation steps having less than 100% efficiency, such as between 95-97% efficiency. Off-products may not include the full length barcode sequence as the desired products and/or may lack a functional sequence. The overall efficiency of a combinatorial process may decrease for processes involving more ligation steps (e.g., triple ligation may be less efficient and generate more off-products than double ligation). Because off-products may interfere with biochemical reactions of interest, it may be beneficial to remove off-products (e.g., partial ligation products) without having other adverse effects on desired products. Removing the off-products may comprise degrading the off-products. Degrading these components may be accomplished by, for example, the use of one or more exonucleases. Exonucleases (e.g., ExoI) are typically inhibited by phosphorothioate bonds in the phosphate backbone of a nucleic acid. By incorporating a phosphorothioate bond between the final 3' base of a barcode molecule and the base immediately preceding it, a molecule can be created that is resistant to 3'→5' exonuclease activity. This bond can be incorporated onto the final oligo that is ligated during a split pool ligation process. In this case, only molecules that are full length (e.g., desired products) can be protected from the exonuclease and partial ligation products (e.g., off-target products) may be digested by the exonuclease. This process may provide a population of molecules that include nearly 100% of the desired molecules (e.g., full length). Such a process may be particularly useful in a triple ligation approach where the initial efficiency may otherwise be undesirably low. This process may be used on any pool of molecules constructed in a combinatorial process where the final component (e.g., molecular segment or sequence) added includes a 3' phosphorothioate bond. The process may be performed within partitions (e.g., droplets or wells) and/or with molecules (e.g., barcode molecules) coupled to beads (e.g., gel beads) or a solid surface. Alternatively, the process may be performed with molecules (e.g., barcode molecules) in solution. A variety of exonucleases may be used in the process, including exonucleases unable to degrade phosphorothioate bonds. Other 3' modifications can be used to achieve the same effect including, for example, spacer molecules, biotin, and fluorophores. Blockers at the 3' end of a complete barcode molecule may also be employed. Such modifications may inhibit the ability of the molecule (e.g., barcode molecule) to particulate in a given reaction, however. Accordingly, a modification may be removed or reversed subsequent to an exonuclease digestion process, e.g., using an enzymatic or chemical mechanism.

The use of exonucleases such as Exonuclease I (ExoI) to "clean-up" combinatorial processes performed on supports (e.g., gel beads) permits digestion of partially ligated molecules, leaving only fully ligated barcode molecules coupled to the supports. Notably, exonucleases such as ExoI may be stored in solutions comprising one or more materials capable of degrading supports (e.g., gel beads). For example, a solution for storing ExoI may include dithiothreitol (DTT), which may degrade gel beads. Accordingly, an exonuclease may be purified before it is used according to the methods provided herein.

A method of improving efficiency of a combinatorial assembly process may comprise performing one or more ligation processes (e.g., as described herein), performing an additional ligation process using a molecular segment or sequence comprising a phosphorothioate moiety, and subjecting the resulting ligation products to conditions sufficient to remove or degrade products that do not comprise the molecular segment or sequence comprising the phosphorothioate moiety. These conditions may comprise combining the ligation products with an exonuclease such as ExoI. The exonuclease may be included in a buffered solution, such as a solution comprising Tris-HCl, $MgCl_2$, NaCl, Triton X-100, glycerol, and/or ATP. The conditions may comprise incubation at, e.g., about 37 degrees Celsius (° C.) or higher for several minutes. In an example, the ligation products may be incubated with the exonuclease at about 37° C. for about 1 hour and may then be subjected to approximately 15 minutes of incubation at a higher temperature such as about 65° C.

Figure 26:
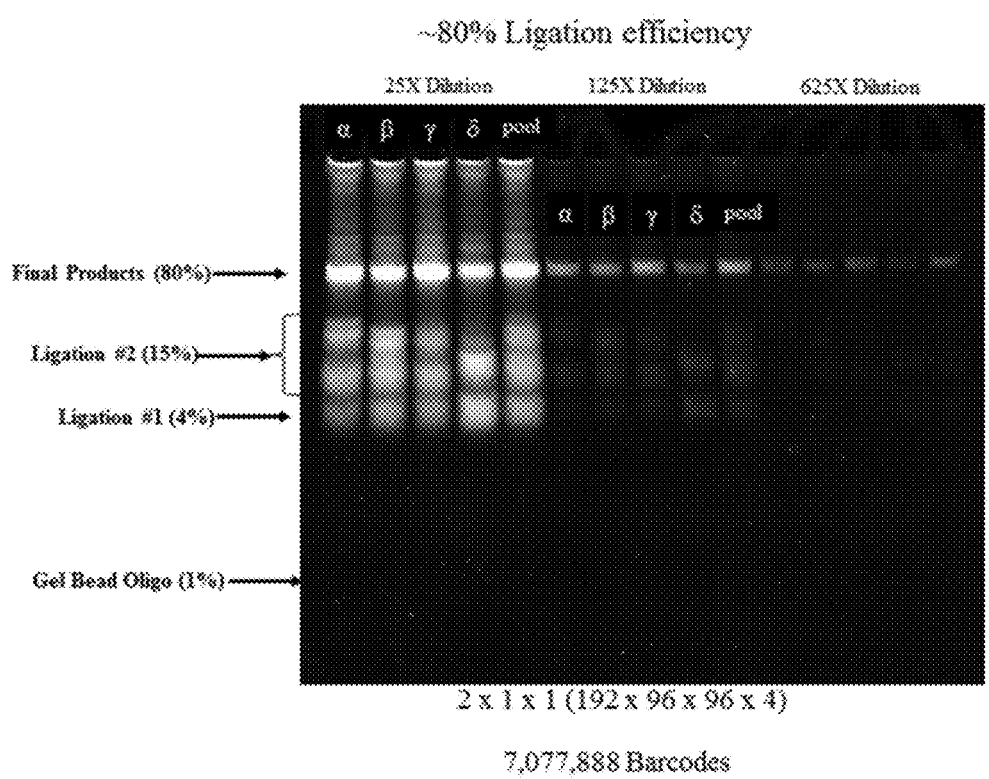
FIG. 26 shows the decrease in ligation efficiency throughout a triple ligation process.

FIG. 26 shows the decrease in ligation efficiency throughout a triple ligation process. The overall ligation efficiency is about 80%, wherein after the triple ligation process, about 80% are final products, with double ligation products remaining at about 15% and single ligation products remaining at about 4%.

Figure 27:
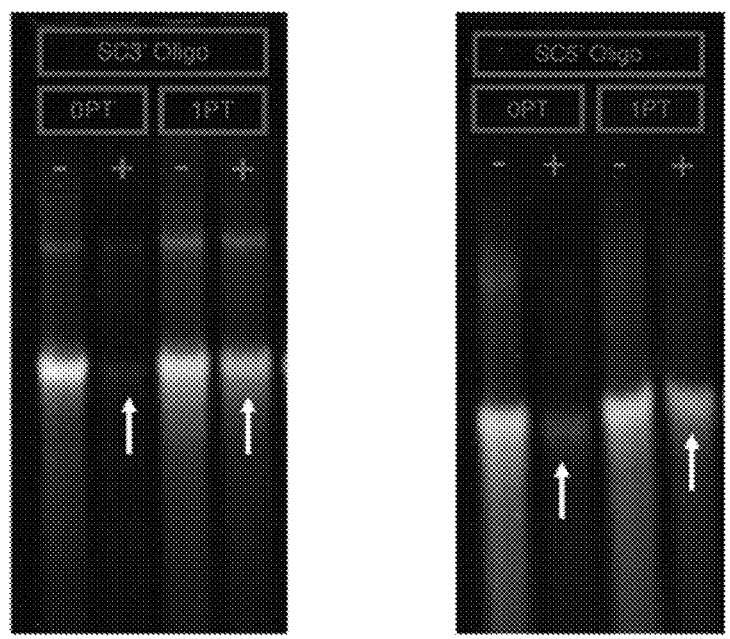
FIG. 27 shows an exonuclease treatment of barcode molecules coupled to gel beads.
Figure 28:
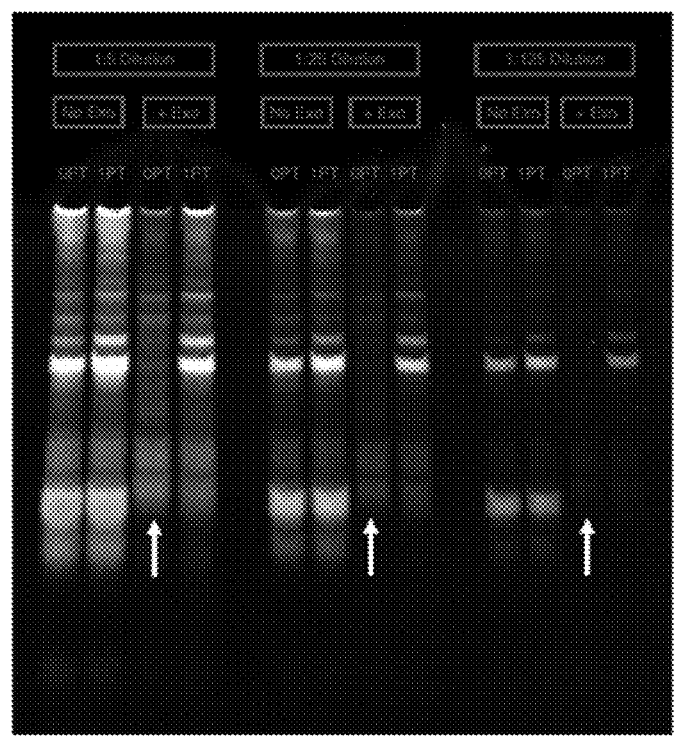
FIG. 28 shows an exonuclease treatment of barcode molecules coupled to gel beads.

FIG. 27 shows an ExoI treatment of barcode molecules coupled to gel beads. In each panel (having four lanes), the left two lanes show results of a reaction without phosphorothioate, and the right two lanes show results of a reaction with phosphorothioate. As shown in each of the panels, the use of phosphorothioate successfully inhibits ExoI activity. Similarly, FIG. 28 shows another ExoI treatment of barcode molecules coupled to gel beads. The figure illustrates three sets of results, a first set (left) of four lanes at 1.5 dilution, a second set (center) of four lanes at 1.25 dilution, and a third set (right) of four lanes at 1.125 dilution. In each set, the first two lanes shows results without ExoI treatment, and the latter two lanes shows results with ExoI treatment. Within each pair of lanes, the left lane shows results of a reaction without phosphorothioate and the right lane shows results of a reaction with phosphorothioate. As seen in each of the sets, phosphorothioate successfully inhibits ExoI activity, leaving the desired product about 50% intact. The exonuclease digests all DNA products that do not have a phosphorothioate at their respective 3' ends. Notably, ExoI purified to remove DTT was incubated with gel beads and minimal bead swelling was observed during the reaction process.

Figure 29A:
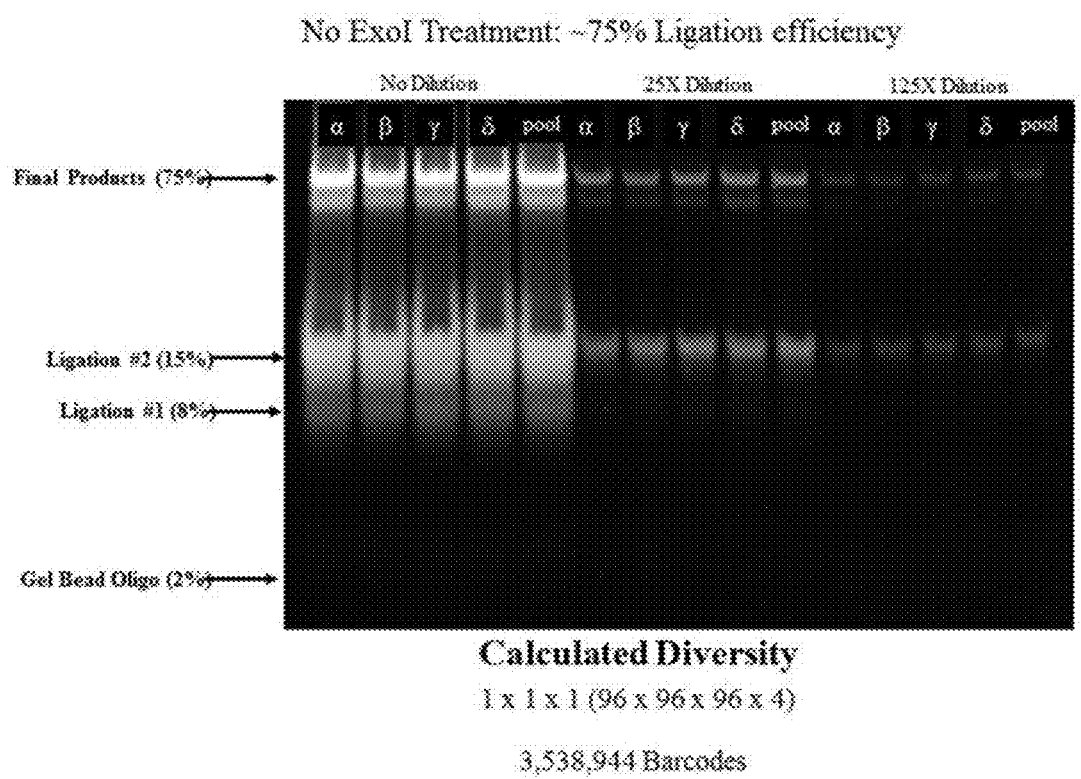
FIGS. 29A and 29B show a triple ligation process in which exonuclease treatment increases ligation efficiency.
Figure 29B:
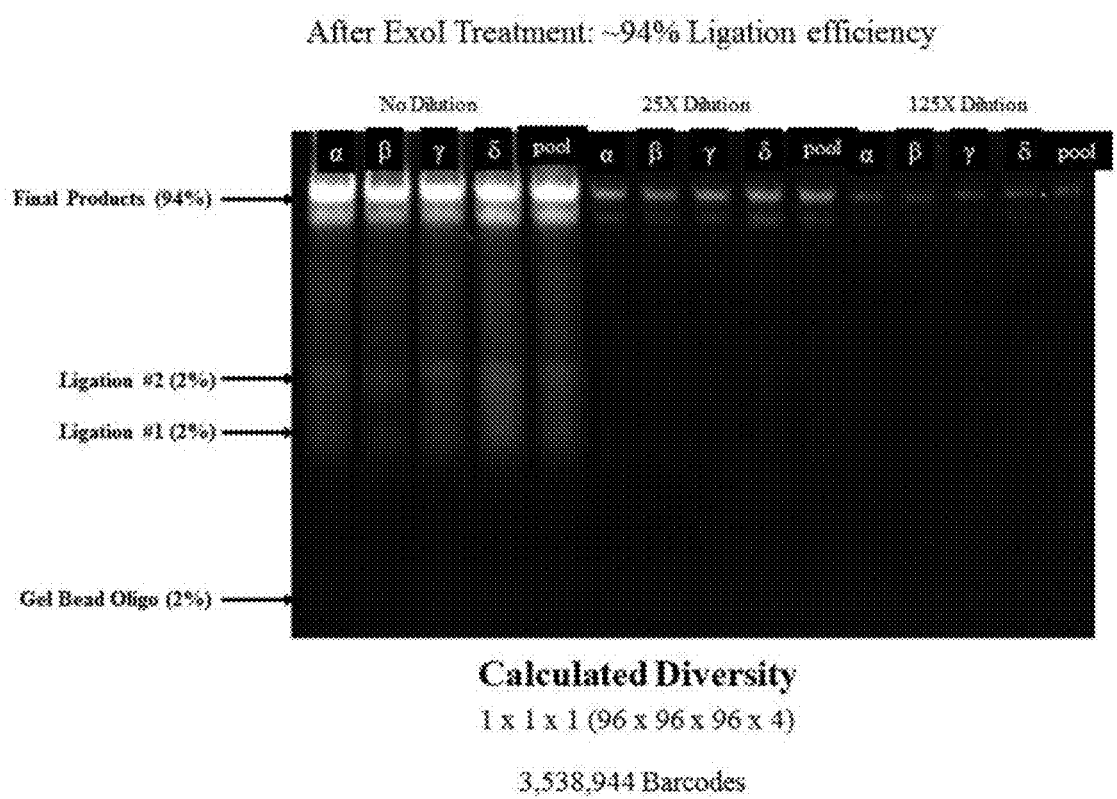
Figure 30A:
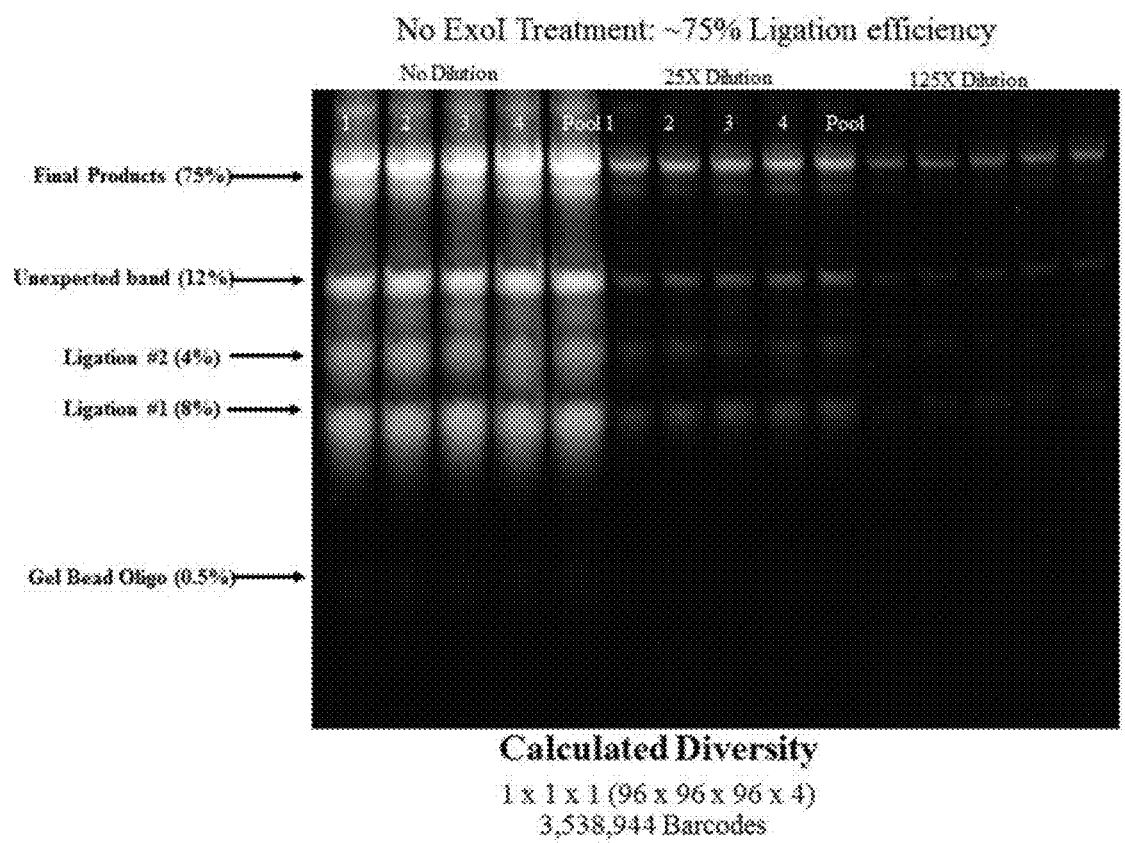
FIGS. 30A and 30B show a triple ligation process in which exonuclease treatment increases ligation efficiency.
Figure 30B:
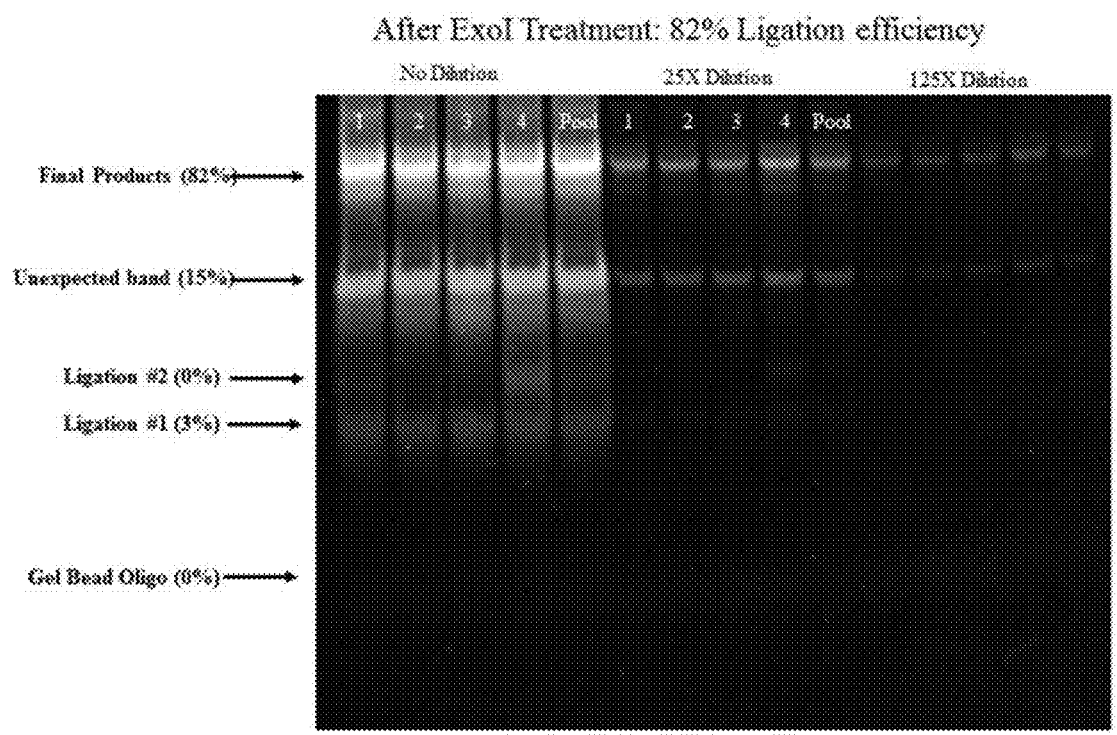
Figure 31:
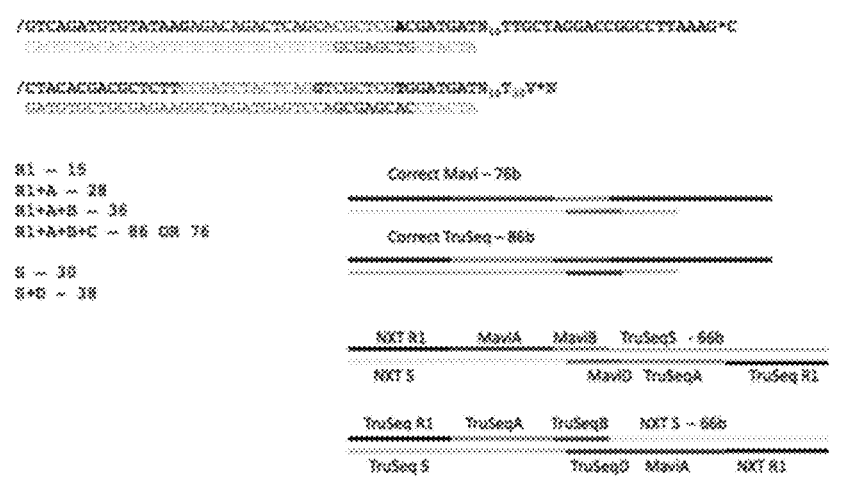

FIGS. 29A and 30A show a triple ligation process in which the overall ligation efficiency without exonuclease treatment is about 75%. As shown in FIG. 29B, the overall ligation efficiency increases to about 94% after incorporating an exonuclease treatment. FIG. 30B shows a process in which efficiency increases to about 82% after incorporating an exonuclease treatment. In this process, an unexpected band is observed which may include a phosphorothioate moiety and/or be a double-stranded product. FIG. 31 shows a scheme relating to these scenarios.

Figure 32:
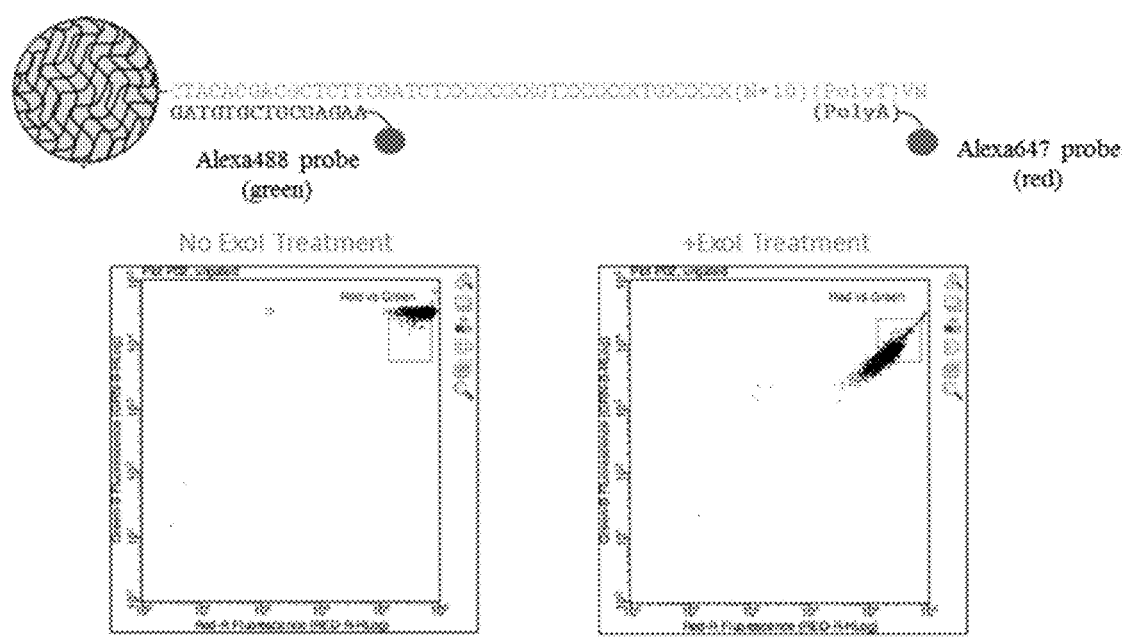
FIG. 32 shows a process in which fluorescent probes were used to examine the effects of exonuclease treatment.

FIG. 32 shows a process in which fluorescent probes were used to examine the effects of exonuclease treatment. The plot on the left shows a plot of green fluorescence (y-axis) vs red fluorescence (x-axis), without ExoI treatment. The plot on the right shows a plot of green fluorescence (y-axis) vs red fluorescence (x-axis), with ExoI treatment.

Figure 33A:
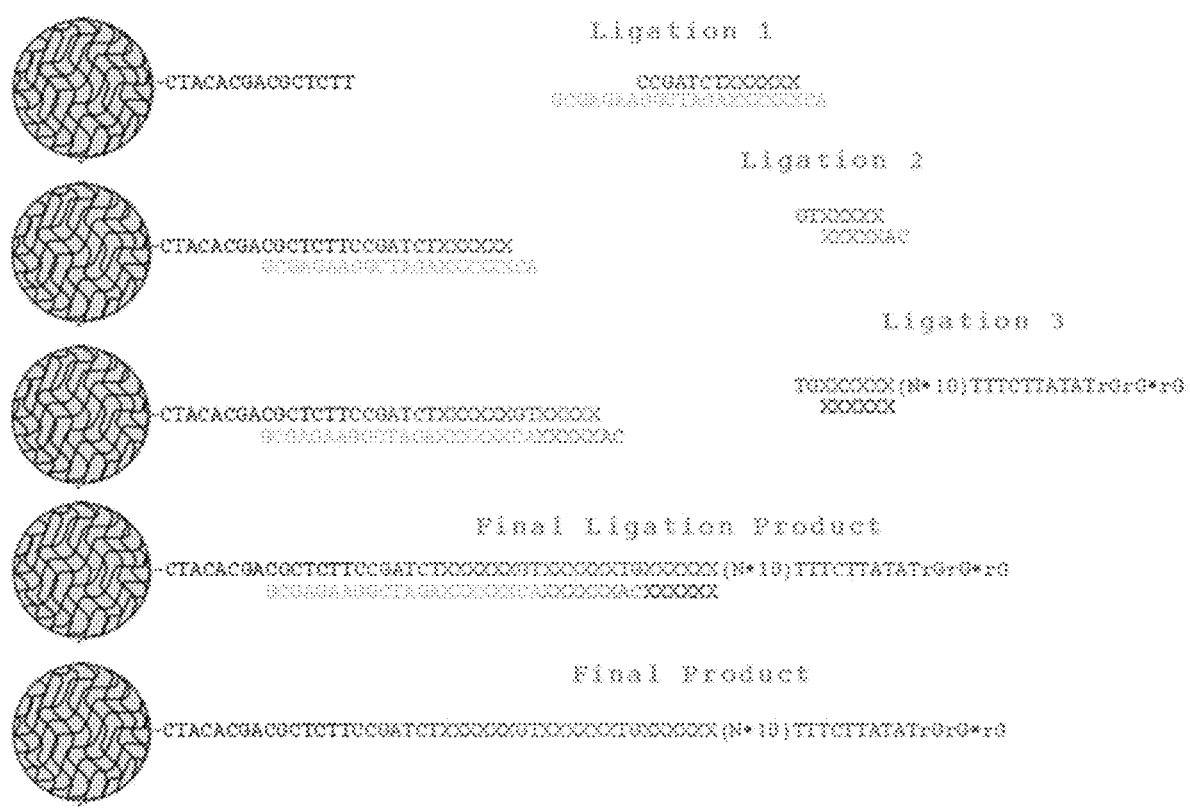
FIG. 33A shows a triple ligation process.
Figure 33B:
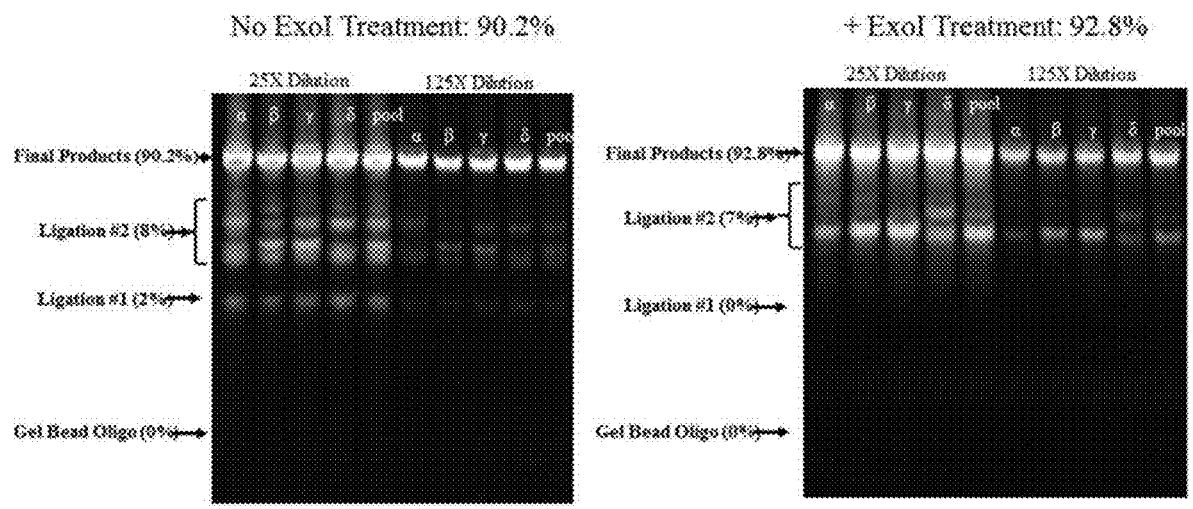
FIGS. 33B and 33C show comparisons between exonuclease treatment and lack of exonuclease treatment for the triple ligation process shown in FIG. 33A.
Figure 33C:
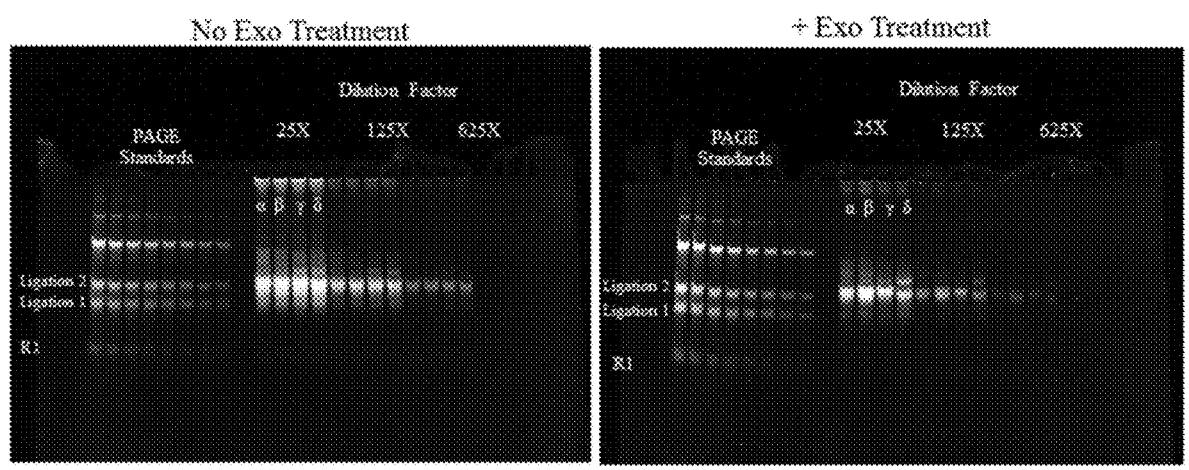

FIG. 33A shows a triple ligation process. FIG. 33B shows a comparison between exonuclease treatment and lack of exonuclease treatment for the triple ligation process shown in FIG. 33A. In this example, the efficiency of the ligation process increased from about 90% to about 93% upon addition of an exonuclease process. FIG. 33C shows a process in which urea and Z1 washes are performed. With and without exonuclease treatment, ligation 2 products are not digested. Accordingly, this gel rules out the possibility of off target phosphorothioate products. Hairpin formation may block the exonuclease activity.

Figure 34:
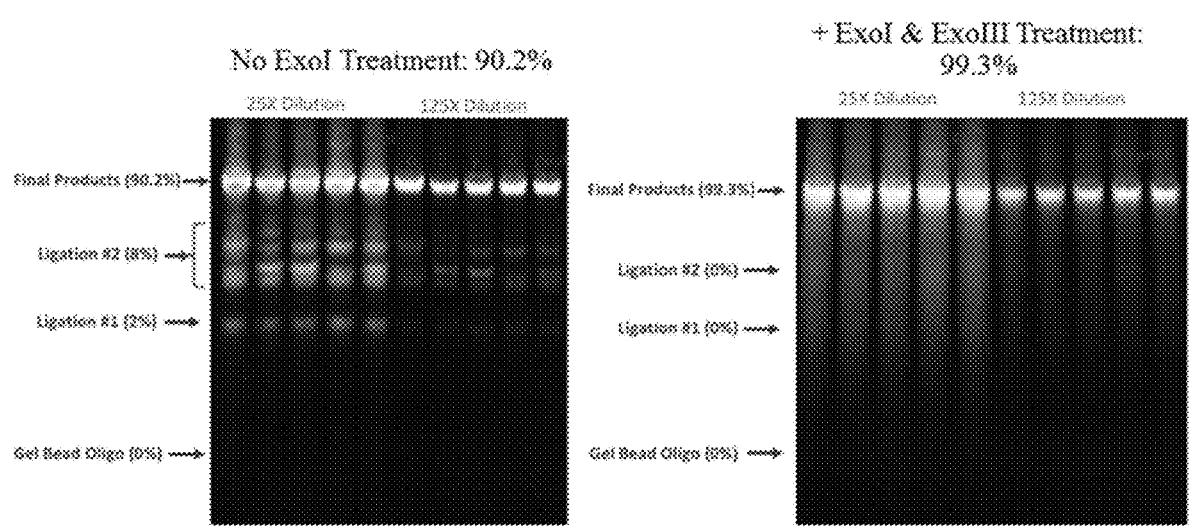
FIG. 34 shows a process involving both ExoI and ExoIII treatments.

ExoIII may be used in addition to or instead of other exonucleases such as ExoI. ExoIII digests double-stranded DNA and is blocked by phosphorothioate bonds. As it may be provided in a solution comprising DTT, hydrogen peroxide may be added to an ExoIII solution to oxidize DTT and prevent unwanted digestion of gel beads. FIG. 34 shows a process involving both ExoI and ExoIII treatments. Gel bead size was unaffected by the exonucleases and hydrogen peroxide.

Figure 35:
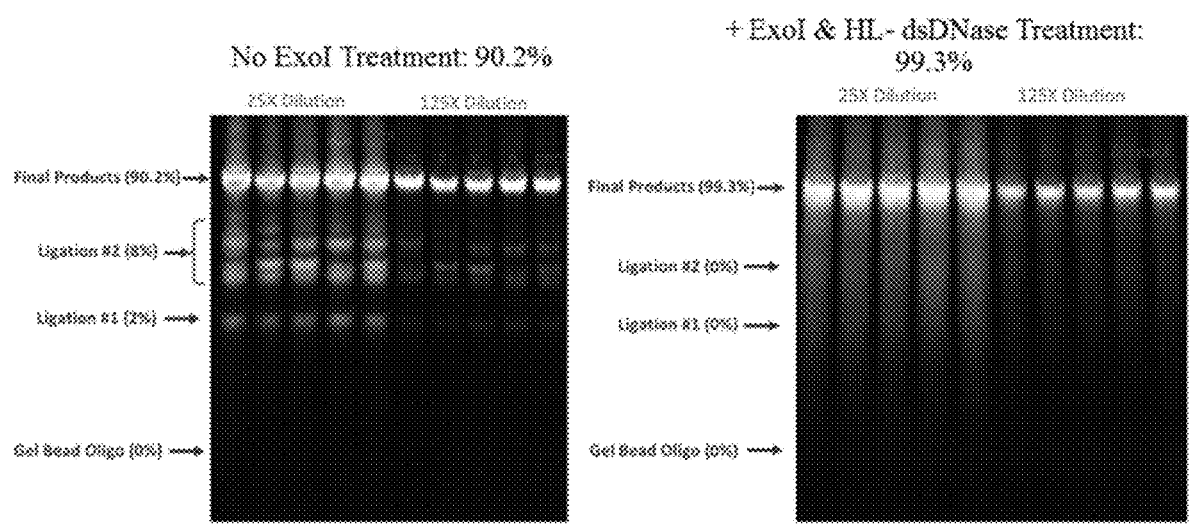
FIG. 35 shows a process involving both ExoI and HL-dsDNase treatment.
Figure 36:
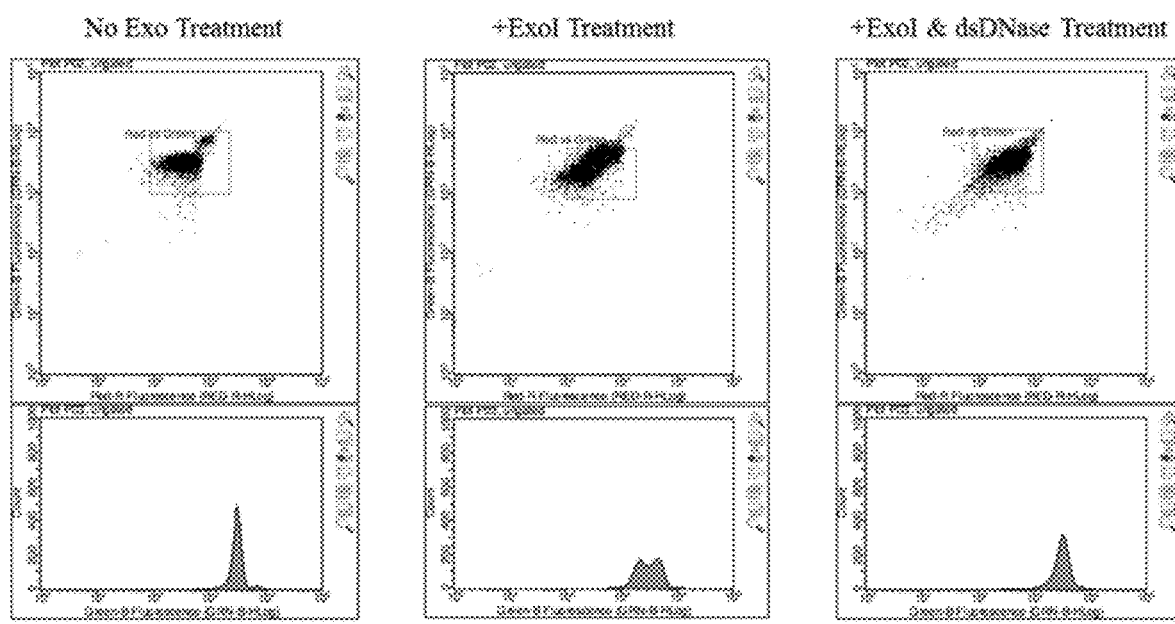
FIG. 36 shows comparisons of processes involving no exonuclease treatment, ExoI treatment, and ExoI and dsDNase treatment in which green and red probes are utilized as in FIG. 32.

Heat-labile dsDNase (arcticzymes) may also be used as alternatives to ExoIIII. Such enzymes do not include DTT and thus do not necessitate the addition of hydrogen peroxide. The enzymes may also be deactivated at lower temperatures than ExoIII. FIG. 35 shows a process involving both ExoI and HL-dsDNase treatment. FIG. 36 shows comparisons of processes involving no exonuclease treatment, ExoI treatment, and ExoI and dsDNase treatment in which green and red probes are utilized as in FIG. 32. The combination of ExoI and HL-dsDNase may fully digest all partially ligated products while leaving about 50% of the desired product intact. This combination allows generation of functionalized gel beads with >99% desired barcode molecules and <1% off-target products without affecting the size of the gel beads (no swelling observed).

The present disclosure also provides kits comprising a plurality of barcode molecules (e.g., nucleic acid barcode molecules). A kit may comprise a plurality of supports (e.g., beads, such as gel beads) and a plurality of barcode molecules coupled to the plurality of supports. The plurality of barcode molecules may comprise (i) a first set of barcode molecules coupled to a support of the plurality of supports and (ii) a second set of barcode molecules coupled to the same support. First barcode molecules of the first set of barcode molecules may be different than second barcode molecules of the second set of barcode molecules. First barcode molecules of the first set of barcode molecules may be configured to interact with different target molecules than second barcode molecules of the second set of barcode molecules. First barcode molecules of the first set of barcode molecules and second barcode molecules of the second set of barcode molecules may comprise barcode sequences that are different from barcode sequences of barcode molecules coupled to other supports of the plurality of supports.

First barcode molecules and second barcode molecules may comprise barcode sequences (e.g., as described herein). The barcode sequences of first barcode molecules and second barcode molecules attached to the same support may be identical.

The plurality of supports may be a plurality of beads (e.g., as described herein), such that barcode molecules (e.g., first barcode molecules of the first set of barcode molecules and the second barcode molecules of the second set of barcode molecules) are coupled to a bead of the plurality of beads. At least a subset of the barcode molecules coupled to a bead may be coupled to an interior of the bead. Alternatively or in addition, barcode molecules may be coupled to a surface (e.g., an interior or exterior surface) of a bead. Barcode molecules may be releasably coupled to a bead, e.g., via chemical cross-linkers (e.g., as described herein). Beads may be gel beads. Beads may be dissolvable or disruptable (e.g., upon application of an appropriate stimulus).

Barcode molecules (e.g., first barcode molecules or said second barcode molecules) coupled to a support (e.g., bead) may be configured to interact with various target molecules. For example, some or all barcode molecules coupled to a given support (e.g., bead) may be configured to interact with DNA molecules. Alternatively or in addition, some or all barcode molecules coupled to a given support (e.g., bead) may be configured to interact with RNA molecules (e.g., mRNA molecules). For example, barcode molecules may comprise a barcode sequence comprising nucleotides (e.g., nucleic acid sequences) that may be configured to interact with one or more nucleic acid molecules (e.g., DNA and RNA molecules). Barcode molecules (e.g., some or all barcode molecules coupled to a given support) may also be configured to interact with amino acids, polypeptides or proteins. For example, barcode molecules may comprise a barcode sequence comprising amino acids that may be configured to interact with one or more amino acids, polypeptides, or proteins.

Different barcode molecules coupled to a support (e.g., bead) may have the same and/or different components (e.g., as described herein). For example, different barcode molecules coupled to the same support may comprise the same or different barcode sequences, starter sequences, functional sequences, or other sequences. In an example, first barcode molecules and second barcode molecules coupled tot the same support (e.g., bead) may comprise a unique identifier that is different than unique identifiers of other barcode molecules coupled to the support. The barcode sequences and/or other sequences of the barcode molecules may be identical. First and second barcode molecules coupled to the same support may have both identical and different barcode sequences. For example, first barcode molecules may have first and second barcode sequences and second barcode molecules may have third and fourth barcode sequences, where the first and third barcode sequences are the same but the second and fourth barcode sequences are different. Different barcode molecules coupled to the same support may have different functional sequences. For example, first barcode molecules coupled to a support may have a first sequence for use with a first assay and second barcode molecules coupled to the same support may have a second sequence for use with a second assay. The first assay may comprise, for example, analysis of first target molecules (e.g., DNA molecules) and the second assay may comprise analysis of second target molecules (e.g., RNA molecules).

Multiple different barcode molecules may be coupled to the same support. For example, two different barcode molecule populations may be coupled to the same support. In another example, three or more different barcode molecule populations may be coupled to the same support. Multiple thousands of barcode molecules may be coupled to the same support. For example, a support (e.g., bead) may comprise at least 100,000 barcode molecules. Different barcode molecules may be present on a support in equal or different portions. For example, a greater number of first barcode molecules may be coupled to the support than second barcode molecules.

The present disclosure also provides a method for processing a plurality of analytes using a plurality of supports comprising a plurality of barcode molecules (e.g., as described herein). The method may comprise providing a plurality of barcode molecules coupled to a plurality of supports (e.g., beads, such as gel beads, as described herein). The plurality of barcode molecules may comprise first and second barcode molecules coupled to the same support. The first and second barcode molecules may be different. The support may be partitioned into a partition (e.g., a droplet or well), such that the partition comprises the support comprising the plurality of barcode molecules as well as a plurality of analytes. The plurality of analytes may comprise, for example, nucleic acid molecules (e.g., DNA and RNA molecules), amino acids, polypeptides, and/or proteins. The plurality of analytes may derive from the same source. For example, the plurality of analytes may be included in or derived from the same biological particle (e.g., cell). The biological particle may be lysed or permeabilized to provide access to the plurality of analytes. Subsequent to partitioning, a first barcode molecule of the first barcode molecules coupled to the support and a first analyte (e.g., a DNA molecule) of the plurality of analytes may be used to generate a first barcoded analyte. A second barcode molecule of the second barcode molecules coupled to the support and a second analyte (e.g., an RNA molecule) of the plurality of analytes may be used to generate a second barcoded analyte. The first and second barcoded analytes, or derivatives thereof, may be recovered from the partition. The first and second barcoded analytes, or derivatives thereof, may then be subjected to subsequent processing and analysis, such as nucleic acid sequencing. A derivative of a barcoded analyte may include one or more functional sequences in addition to those of the barcoded analyte, such as one or more sequencing adapters or primers or other functional sequences. In an example, the first and second barcoded analytes are generated and are subsequently functionalized with sequencing adapters suitable for performing a nucleic acid assay (e.g., nucleic acid sequencing). In another example, a derivative of a barcoded analyte may comprise a portion of the barcoded analyte. For example, a portion of the barcoded analyte may be separated from the barcoded analyte and, optionally, another molecular segment or functional sequence may be added to the barcoded analyte.

Barcode molecules (e.g., first barcode molecules or said second barcode molecules) coupled to a support (e.g., bead) may be configured to interact with various analytes. For example, some or all barcode molecules coupled to a given support (e.g., bead) may be configured to interact with DNA molecules. Alternatively or in addition, some or all barcode molecules coupled to a given support (e.g., bead) may be configured to interact with RNA molecules (e.g., mRNA molecules). For example, barcode molecules may comprise a barcode sequence comprising nucleotides (e.g., nucleic acid sequences) that may be configured to interact with one or more nucleic acid molecules (e.g., DNA and RNA molecules). Barcode molecules configured to interact with DNA molecules may comprise a functional sequence (e.g., a capture sequence, such as a random N-mer) configured to interact with DNA molecules. Barcode molecules configured to interact with RNA molecules may comprise a functional sequence (e.g., a poly(T) sequence) configured to interact with RNA molecules (e.g., mRNA molecules). Barcode molecules (e.g., some or all barcode molecules coupled to a given support) may also be configured to interact with amino acids, polypeptides or proteins. For example, barcode molecules may comprise a barcode sequence comprising amino acids that may be configured to interact with one or more amino acids, polypeptides, or proteins.

Different barcode molecules (e.g., first and second barcode molecules) coupled to the same support (e.g., bead) may comprise barcode sequences that are different from barcode sequences of barcode molecules coupled to other supports of a plurality of supports (e.g., as described herein). First barcode molecules and second barcode molecules may comprise barcode sequences (e.g., nucleic acid sequences that may be configured to interact with nucleic acid molecules or amino acid sequences that may be configured to interact with amino acids, polypeptides, or proteins). Barcode sequences of different barcode molecules coupled to the same bead may be identical. In some cases, barcode sequences of different barcode molecules may be both the same and different (e.g., first barcode molecules may comprise first and second barcode sequences and second barcode molecules coupled to the same bead may comprise third and fourth barcode sequences, where the first and third barcode sequences are the same and the second and fourth barcode sequences are different). In an example, each barcode molecule coupled to a given support (e.g., each first barcode molecule and each second barcode molecule) may have a different unique identifier (e.g., unique molecular identifier). Different barcode molecules coupled to the same support may be coupled to the same bead, such as the same gel bead. The barcode molecules may be releasably coupled to the bead, e.g., via chemical cross-linkers. The bead may be dissolvable or disruptable.

Multiple different barcode molecules may be coupled to the same support (e.g., bead). For example, two different barcode molecule populations may be coupled to the same support. In another example, three or more different barcode molecule populations may be coupled to the same support. Multiple thousands of barcode molecules may be coupled to the same support. For example, a support (e.g., bead) may comprise at least 100,000 barcode molecules. Different barcode molecules may be present on a support in equal or different portions. For example, a greater number of first barcode molecules may be coupled to the support than second barcode molecules. Barcode molecules of other supports of the plurality of supports may comprise different barcode sequences.

Generating barcoded analytes may comprise performing one or more nucleic acid extension reactions. A nucleic acid extension reaction may comprise annealing an analyte (e.g., a DNA or RNA molecule) to a barcode molecule of a plurality of barcode molecules coupled to a support. For example, the analyte may hybridize to a functional sequence of the barcode molecule. An extension reaction (e.g., primer extension reaction) may then take place (e.g., using a polymerase molecule such as a DNA polymerase molecule). The hybridization and extension reactions may be isothermal or may occur at one or more elevated temperatures. The extension product may then be separated from the barcode molecule. The extension product (e.g., barcoded analyte) may comprise one or more barcode sequences of the barcode molecule or complements thereof. The barcode molecule or sequences thereof may be coupled to the support (e.g., bead) throughout the extension reaction, or the barcode molecule or a sequence thereof may be released from the support during or after the extension reaction. In an example, the first and second barcode molecule or sequences thereof may be released from the support prior to the nucleic acid extension reaction (e.g., upon application of an appropriate stimulus, as described herein). The first and/or second barcoded analytes may be coupled to the bead. The first and/or second barcoded analytes may be in solution in the partition (e.g., droplet or well) subsequent to their generation. For example, the first and/or second barcoded analytes may be generated in solution. Alternatively, the first and/or second barcoded analytes may be generated using barcode molecules that are coupled to support and subsequently released from the support (e.g., by denaturing the extension products (barcoded analytes) from the barcode molecules coupled to the support and/or by releasing the first and/or second barcode molecules used to generate the first and second barcoded analytes or sequences thereof from the support).

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for at most a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
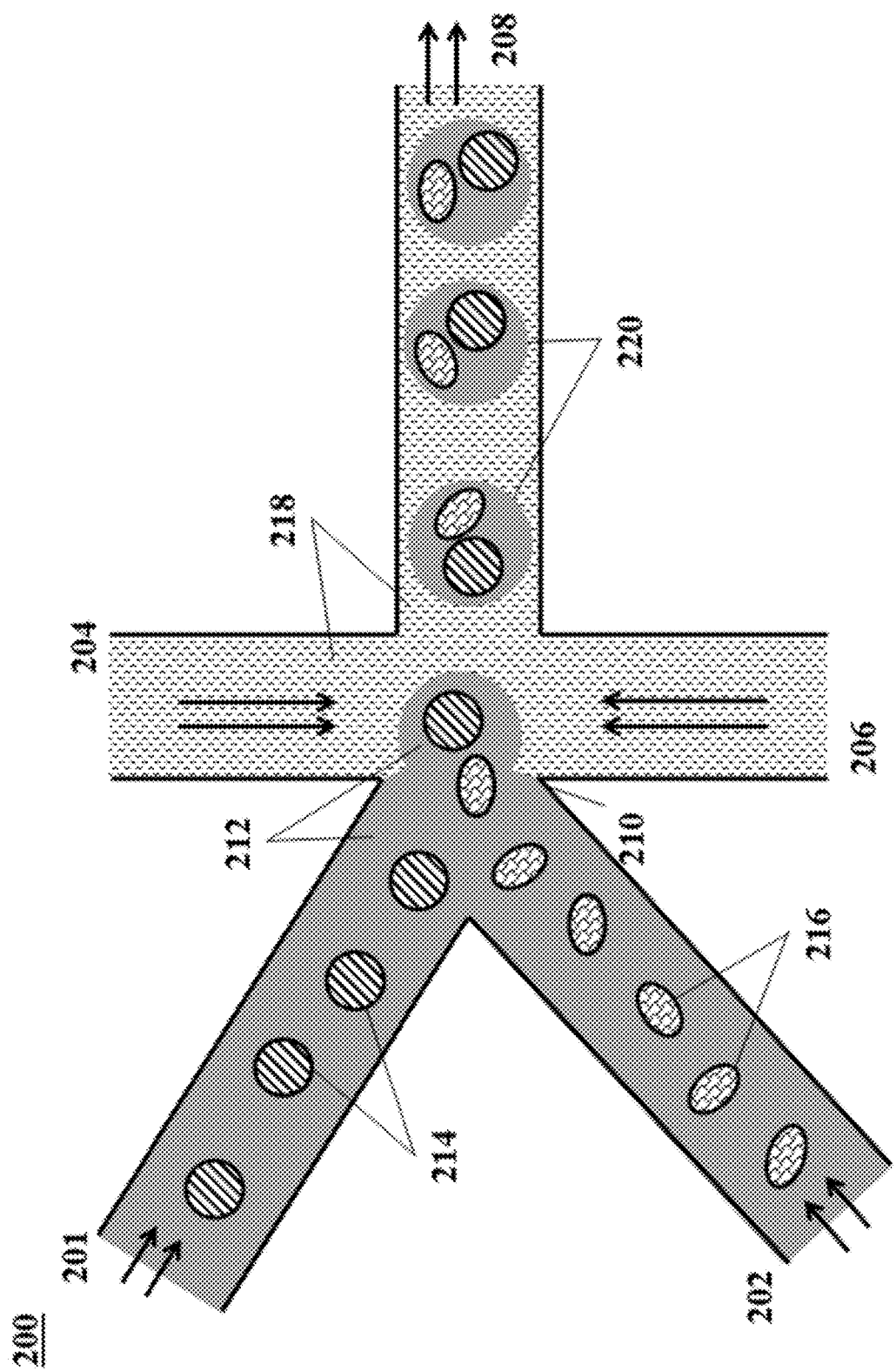
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions.

For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer ($\mu m$), 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or greater. In some cases, a bead may have a diameter of less than about 10 nm, 100 nm, 500 nm, 1 $\mu m$, 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or less. In some cases, a bead may have a diameter in the range of about 40-75 $\mu m$, 30-75 $\mu m$, 20-75 $\mu m$, 40-85 $\mu m$, 40-95 $\mu m$, 20-100 $\mu m$, 10-100 $\mu m$, 1-100 $\mu m$, 20-250 $\mu m$, or 20-500 $\mu m$.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
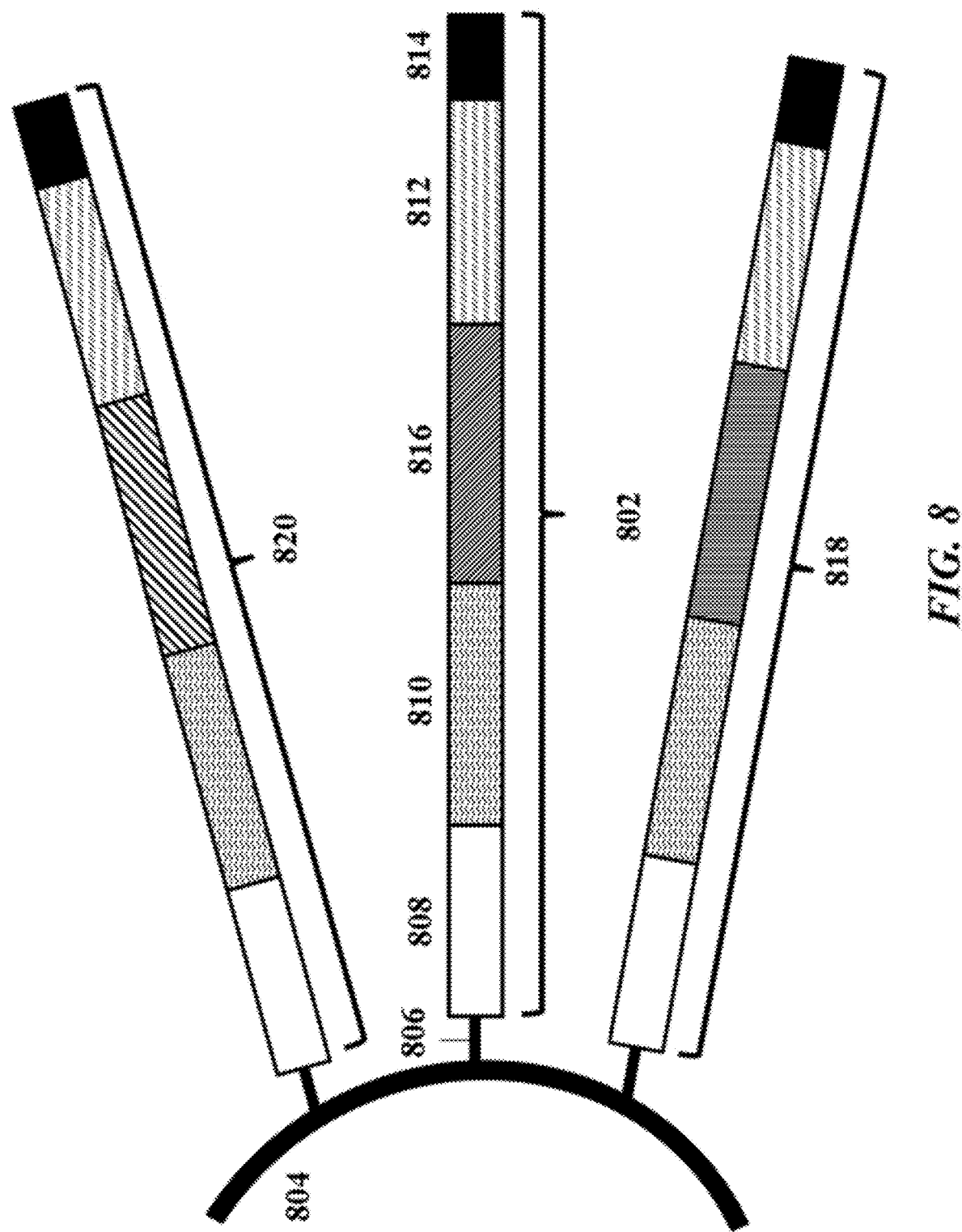
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of an mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that at most a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about $\frac{1}{10}$th, less than about $\frac{1}{50}$th, or even less than about $\frac{1}{100}$th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
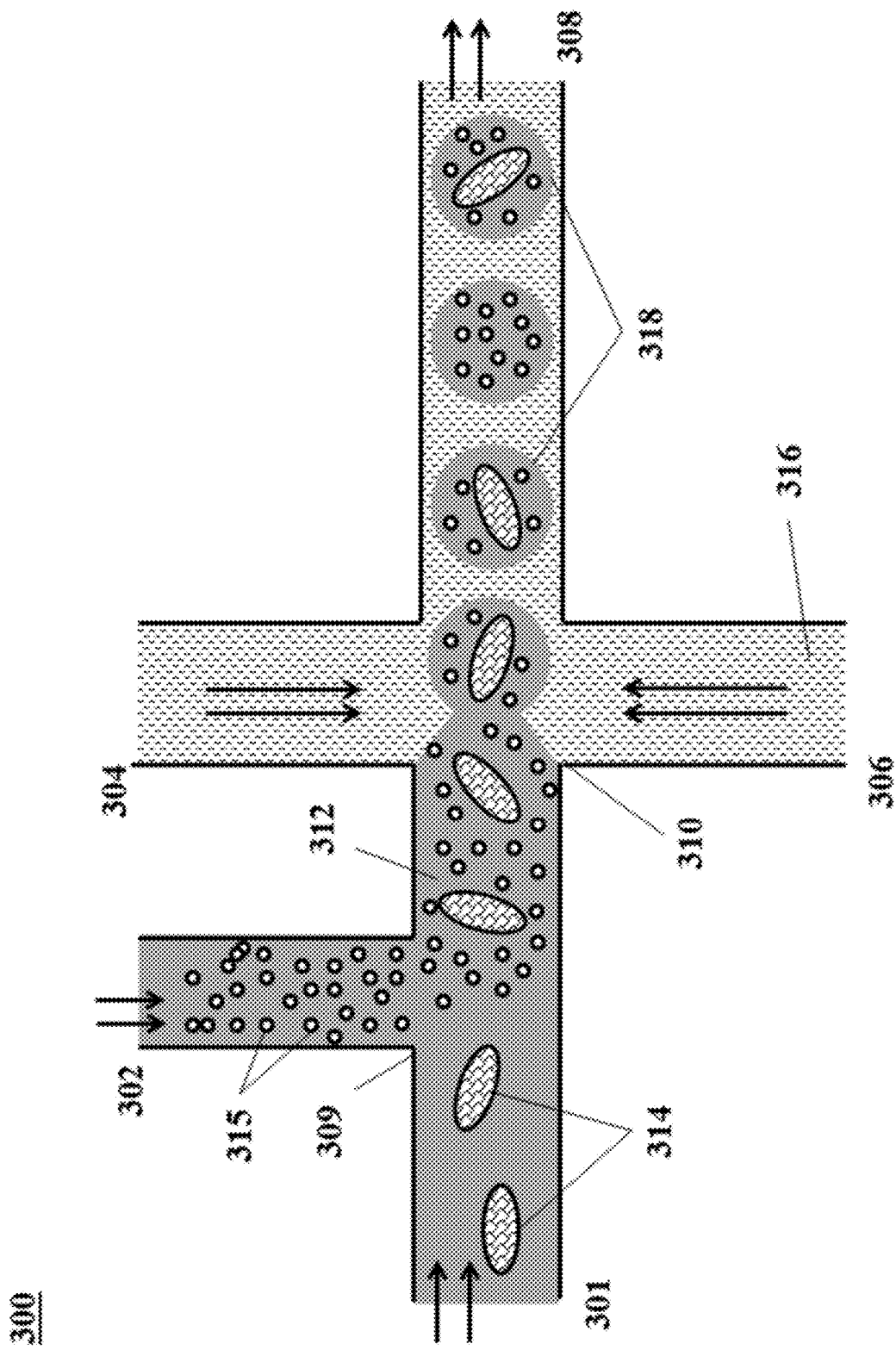
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the biological particles to cause the release of the biological particles' contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as described elsewhere herein, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
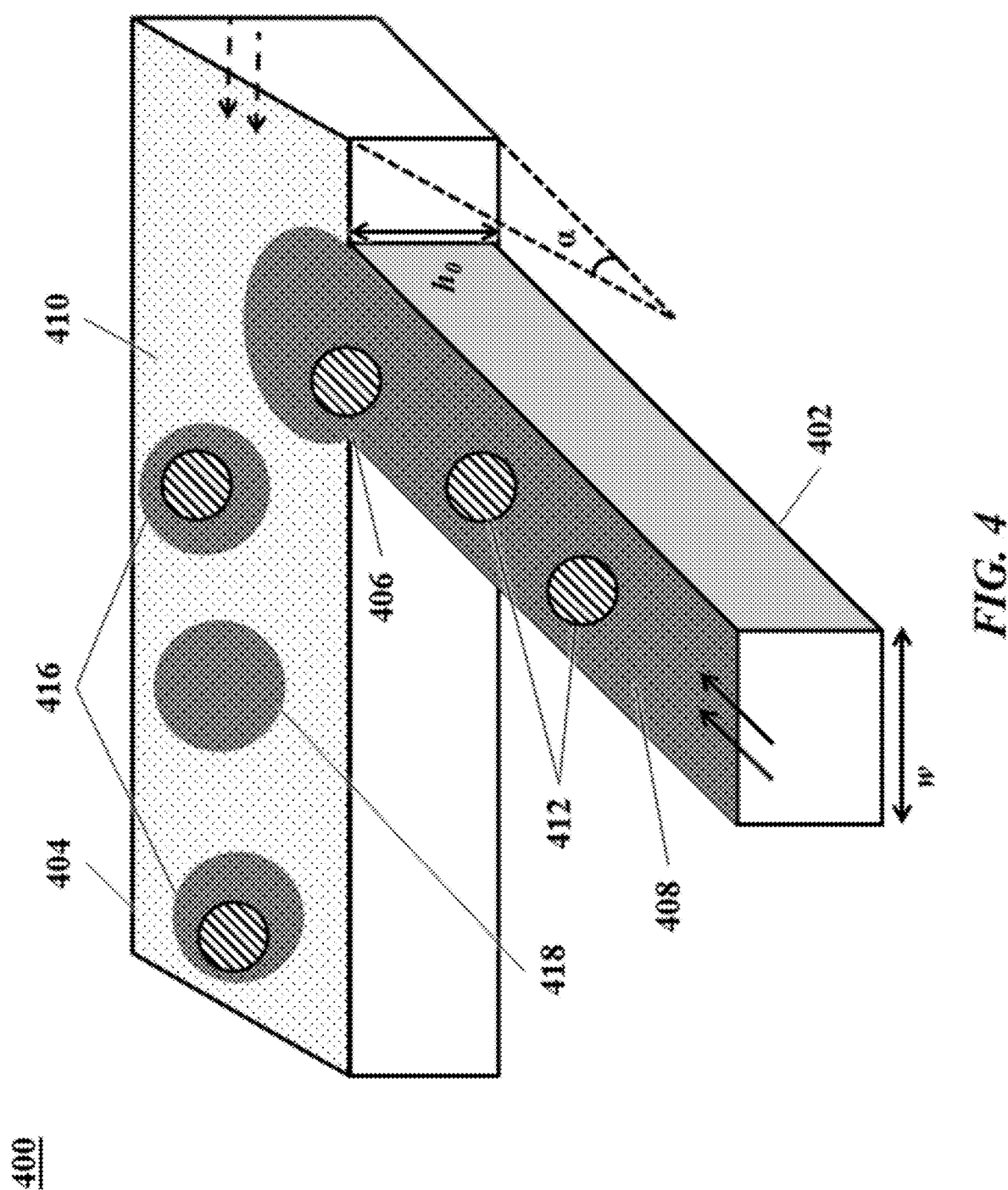
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, $\alpha$, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, $\alpha$. The expansion angle, $\alpha$, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 µm, h=21 µm, and $\alpha$=3°, the predicted droplet size is 121 µm. In another example, for a channel structure with w=25 µm, h=25 µm, and $\alpha$=5°, the predicted droplet size is 123 µm. In another example, for a channel structure with w=28 µm, h=28 µm, and $\alpha$=7°, the predicted droplet size is 124 µm.

In some instances, the expansion angle, $\alpha$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 830, 820, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (µm) to about 500 µm. In some instances, the width, w, can be between a range of from about 10 µm to about 200 µm. Alternatively, the width can be less than about 10 µm. Alternatively, the width can be greater than about 500 µm. In some instances, the flow rate of the aqueous fluid 408 entering the junction 406 can be between about 0.04 microliters (µL)/minute (min) and about 40 µL/min. In some instances, the flow rate of the aqueous fluid 408 entering the junction 406 can be between about 0.01 microliters (µL)/minute (min) and about 100 µL/min. Alternatively, the flow rate of the aqueous fluid 408 entering the junction 406 can be less than about 0.01 µL/min. Alternatively, the flow rate of the aqueous fluid 408 entering the junction 406 can be greater than about 40 µL/min, such as 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
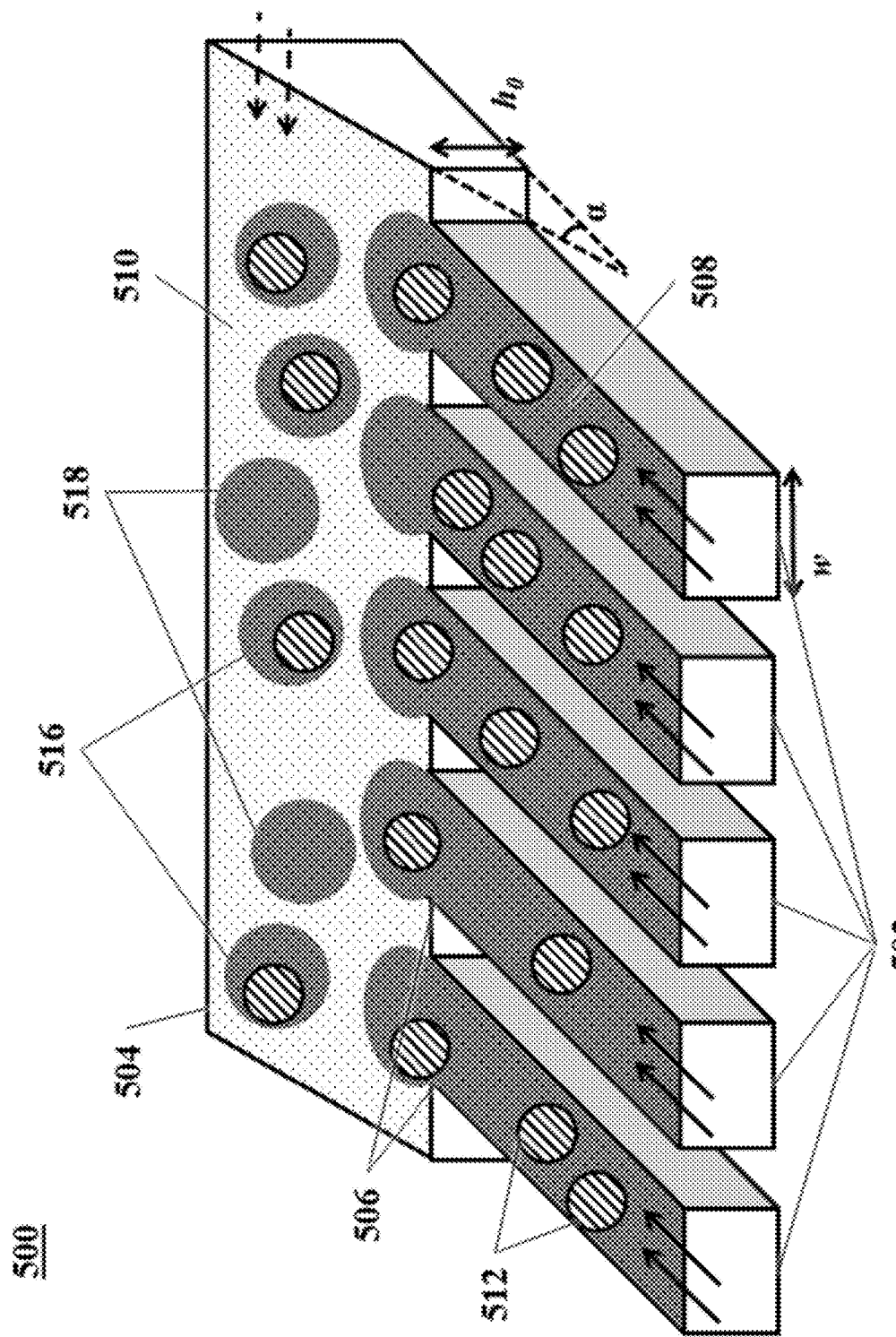
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
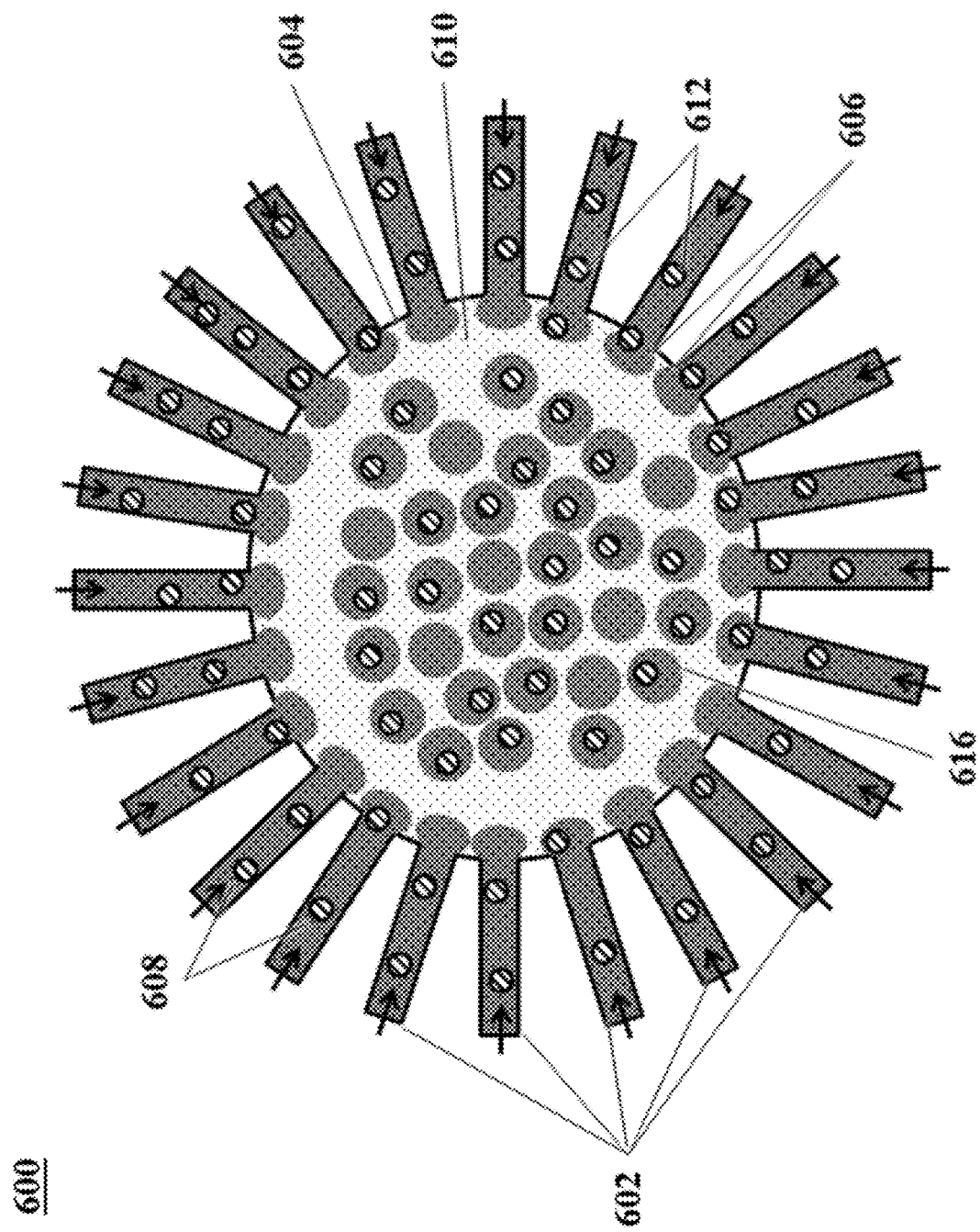
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, $\alpha$ (not shown in FIG. 6) at or near each channel junction. Each channel segment of the plurality of channel segments 602 may have a width, w, and a height, $h_0$, at or near the channel junction. The geometric parameters, w, $h_0$, and $\alpha$, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figure 7A:
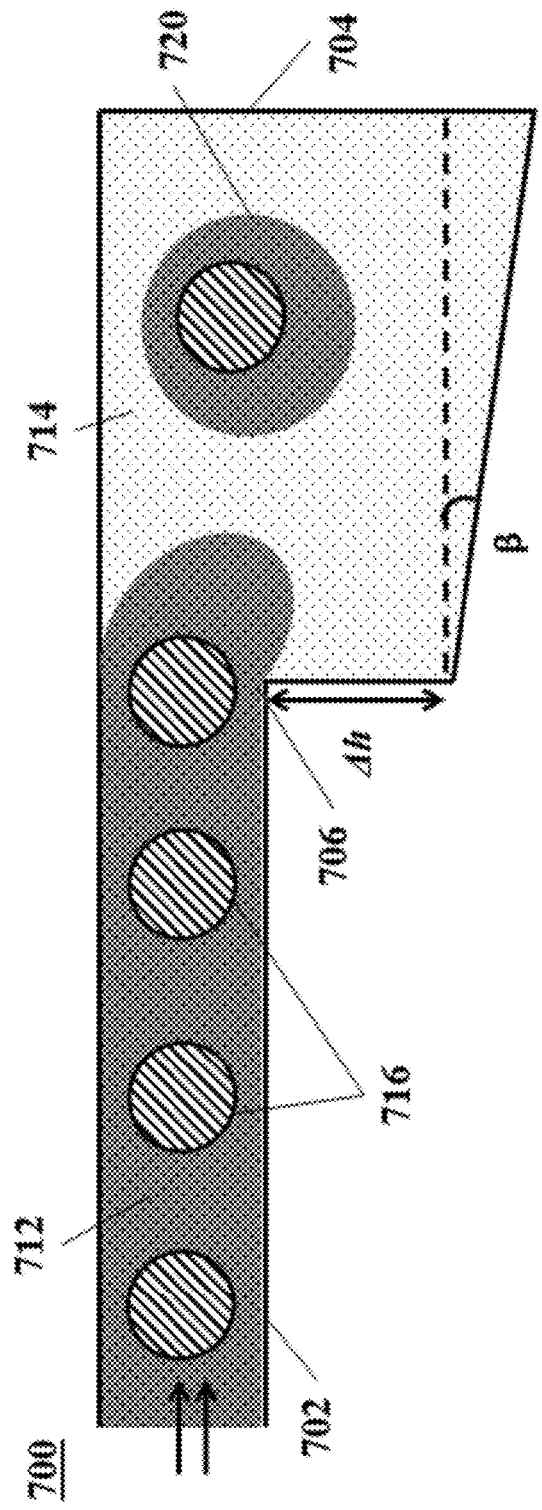
FIG. 7A shows a cross-section view of another example of a microfluidic channel structure with a geometric feature for controlled partitioning.
Figure 7B:
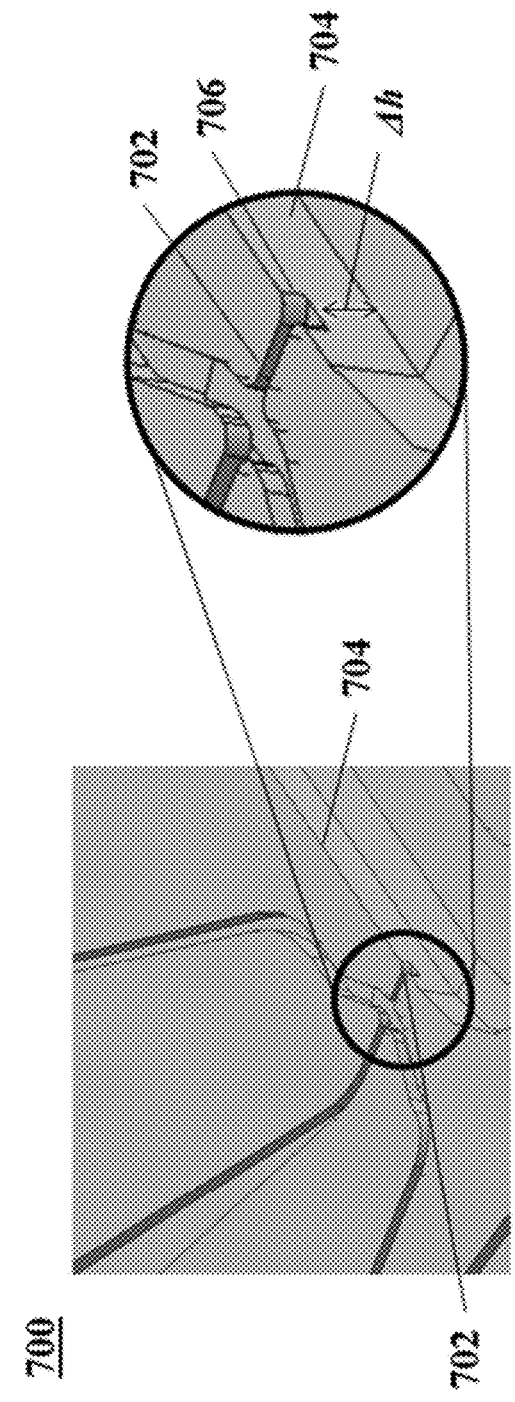
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., $\Delta h$, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of $\Delta h$. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, $\beta$, at or near the junction 706. The height difference, $\Delta h$, and/or expansion angle, $\beta$, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, $\Delta h$, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 μL/min. Alternatively, the flow rate of the aqueous fluid 712 entering the junction 706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, $\Delta h$, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, $\beta 8$), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 25:
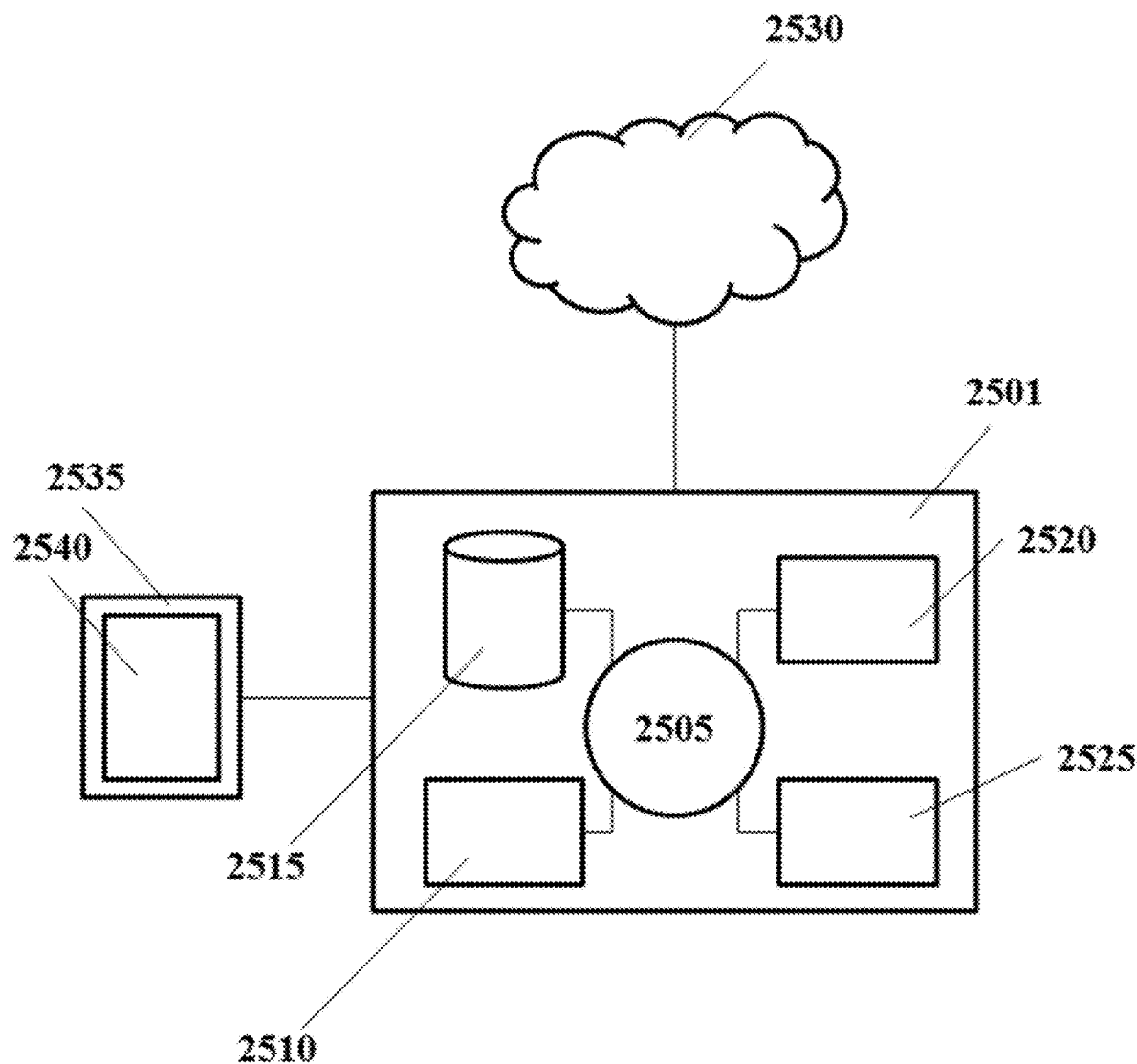
FIG. 25 shows a computer system that is programmed or otherwise configured to implement methods provided herein.

The present disclosure provides computer systems that are programmed to implement methods of the disclosure. FIG. 25 shows a computer system 2501 that is programmed or otherwise configured to, for example, (i) control a microfluidics system (e.g., fluid flow), (ii) sort occupied droplets from unoccupied droplets, (iii) polymerize droplets, (iv) perform sequencing applications, or (v) generate and maintain a library of barcode molecules. The computer system 2501 can regulate various aspects of the present disclosure, such as, for example, fluid flow rates in one or more channels in a microfluidic structure, polymerization application units, etc. The computer system 2501 can be an electronic device of a user or a computer system that is remotely located with respect to the electronic device. The electronic device can be a mobile electronic device.

The computer system 2501 includes a central processing unit (CPU, also "processor" and "computer processor" herein) 2505, which can be a single core or multi core processor, or a plurality of processors for parallel processing. The computer system 2501 also includes memory or memory location 2510 (e.g., random-access memory, read-only memory, flash memory), electronic storage unit 2515 (e.g., hard disk), communication interface 2520 (e.g., network adapter) for communicating with one or more other systems, and peripheral devices 2525, such as cache, other memory, data storage and/or electronic display adapters. The memory 2510, storage unit 2515, interface 2520 and peripheral devices 2525 are in communication with the CPU 2505 through a communication bus (solid lines), such as a motherboard. The storage unit 2515 can be a data storage unit (or data repository) for storing data. The computer system 2501 can be operatively coupled to a computer network ("network") 2530 with the aid of the communication interface 2520. The network 2530 can be the Internet, an internet and/or extranet, or an intranet and/or extranet that is in communication with the Internet. The network 2530 in some cases is a telecommunication and/or data network. The network 2530 can include one or more computer servers, which can enable distributed computing, such as cloud computing. The network 2530, in some cases with the aid of the computer system 2501, can implement a peer-to-peer network, which may enable devices coupled to the computer system 2501 to behave as a client or a server.

The CPU 2505 can execute a sequence of machine-readable instructions, which can be embodied in a program or software. The instructions may be stored in a memory location, such as the memory 2510. The instructions can be directed to the CPU 2505, which can subsequently program or otherwise configure the CPU 2505 to implement methods of the present disclosure. Examples of operations performed by the CPU 2505 can include fetch, decode, execute, and writeback.

The CPU 2505 can be part of a circuit, such as an integrated circuit. One or more other components of the system 2501 can be included in the circuit. In some cases, the circuit is an application specific integrated circuit (ASIC).

The storage unit 2515 can store files, such as drivers, libraries and saved programs. The storage unit 2515 can store user data, e.g., user preferences and user programs. The computer system 2501 in some cases can include one or more additional data storage units that are external to the computer system 2501, such as located on a remote server that is in communication with the computer system 2501 through an intranet or the Internet.

The computer system 2501 can communicate with one or more remote computer systems through the network 2530. For instance, the computer system 2501 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2501 via the network 2530.

Methods as described herein can be implemented by way of machine (e.g., computer processor) executable code stored on an electronic storage location of the computer system 2501, such as, for example, on the memory 2510 or electronic storage unit 2515. The machine executable or machine readable code can be provided in the form of software. During use, the code can be executed by the processor 2505. In some cases, the code can be retrieved from the storage unit 2515 and stored on the memory 2510 for ready access by the processor 2505. In some situations, the electronic storage unit 2515 can be precluded, and machine-executable instructions are stored on memory 2510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2501 can include or be in communication with an electronic display 2535 that comprises a user interface (UI) 2540 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 2505. The algorithm can, for example, perform sequencing, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) form a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for generating nucleic acid barcode molecules, comprising:
   (a) providing a plurality of nucleic acid molecules coupled to a support;
   (b) coupling one or more additional nucleic acid molecules to nucleic acid molecules of the plurality of nucleic acid molecules coupled to the support, thereby assembling a plurality of nucleic acid barcode molecules coupled to the support, wherein the plurality of nucleic acid barcode molecules comprises a plurality of target products and a plurality of off-target products; and
   (c) digesting off-target products of the plurality of off-target products with an exonuclease, wherein target products of the plurality of target products comprise an exonuclease-resistant bond, and wherein fewer than 50% of the target products comprising the exonuclease-resistant bond are digested with the exonuclease.

2. The method of claim 1, wherein the exonuclease comprises an Exo1 exonuclease, an ExoIII nuclease, a heat-labile DNAse, or a combination thereof.

3. The method of claim 1, wherein a subset of the plurality of nucleic acid molecules is free of an exonuclease-resistant bond.

4. The method of claim 1, wherein the exonuclease-resistant bond is a phosphorothioate bond.

5. The method of claim 1, wherein the exonuclease-resistant bond is disposed between a final 3' base of the one or more additional nucleic acid molecules and a base immediately preceding the final 3' base of the one or more additional nucleic acid molecules.

6. The method of claim 1, wherein a subset of the nucleic acid barcode molecules is free of an exonuclease-resistant bond.

7. The method of claim 1, wherein (c) is performed in an absence of a reducing agent.

8. The method of claim 1, wherein (c) is performed in an absence of dithiothreitol (DTT).

9. The method of claim 1, wherein (c) is performed at a temperature from about 37 degrees Celsius to about 65 degrees Celsius.

10. The method of claim 9, wherein (c) is performed at the temperature for about 15 minutes to about 1 hour.

11. The method of claim 1, wherein the support is a bead.

12. The method of claim 11, wherein the bead is a gel bead.

13. The method of claim 11, wherein, in (c), the digesting does not digest the bead.

14. The method of claim 1, wherein a nucleic acid molecule of the plurality of nucleic acid molecules comprises a barcode sequence and an additional nucleic acid molecule of the one or more additional nucleic acid molecules comprises an additional barcode sequence.

15. The method of claim 14, wherein the barcode sequence is different from the additional barcode sequence.

16. The method of claim 1, wherein the plurality of nucleic acid molecules is coupled to the support via a labile moiety.

17. The method of claim 1, wherein (b) further comprises coupling a plurality of additional nucleic acid molecules to a nucleic acid molecule of the plurality of nucleic acid molecules coupled to the support, thereby assembling a nucleic acid barcode molecule of the plurality of nucleic acid barcode molecules coupled to the support.

18. The method of claim 1, wherein, in (b), coupling the one or more additional nucleic acid molecules to the nucleic acid molecules of the plurality of nucleic acid molecules coupled to the support couples a capture sequence to the nucleic acid molecules.

* * * * *